(12) United States Patent
Li et al.

(10) Patent No.: US 11,512,111 B2
(45) Date of Patent: Nov. 29, 2022

(54) YEATS INHIBITORS AND METHODS OF USE THEREOF

(71) Applicant: The University of Hong Kong, Pokfulam (HK)

(72) Inventors: Xiang David Li, Tsing Yi (HK); Xin Li, Kowloon (HK)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 16/767,434

(22) PCT Filed: Nov. 26, 2018

(86) PCT No.: PCT/CN2018/117418
§ 371 (c)(1),
(2) Date: May 27, 2020

(87) PCT Pub. No.: WO2019/101195
PCT Pub. Date: May 31, 2019

(65) Prior Publication Data
US 2021/0277061 A1 Sep. 9, 2021

Related U.S. Application Data

(60) Provisional application No. 62/590,690, filed on Nov. 27, 2017.

(51) Int. Cl.
| | | |
|---|---|---|
| *C07K 7/08* | (2006.01) | |
| *A61P 35/04* | (2006.01) | |
| *C07K 7/50* | (2006.01) | |
| *A61K 38/00* | (2006.01) | |

(52) U.S. Cl.
CPC ............... *C07K 7/08* (2013.01); *A61P 35/04* (2018.01); *C07K 7/50* (2013.01); *A61K 38/00* (2013.01)

(58) Field of Classification Search
CPC .. C07K 7/08; C07K 7/50; A61P 35/04; A61K 38/00
See application file for complete search history.

(56) References Cited

U.S. PATENT DOCUMENTS

| | | | | |
|---|---|---|---|---|
| 2003/0078374 A1* | 4/2003 | Roberts | .................... | C07K 7/06 702/19 |
| 2003/0103899 A1* | 6/2003 | Cyr | ...................... | A61K 51/121 424/1.69 |
| 2006/0025337 A1* | 2/2006 | Sinclair | .................. | A61P 25/28 514/17.8 |
| 2007/0254831 A1* | 11/2007 | Mezo | ........................ | A61P 3/10 435/7.1 |
| 2010/0303728 A1* | 12/2010 | Wendt | .................. | G01N 33/542 424/9.6 |
| 2011/0230639 A1* | 9/2011 | Mezo | ...................... | A61P 37/06 530/324 |
| 2014/0004050 A1* | 1/2014 | Rajadas | ............... | A61K 49/006 424/9.6 |
| 2015/0038403 A1* | 2/2015 | Geysen | ................ | C07K 14/505 530/321 |
| 2016/0115202 A1* | 4/2016 | Pei | ....................... | C07K 5/0817 530/321 |

OTHER PUBLICATIONS

Andrews et al., 2016, The Taf14 YEATS domain is a reader of histone crotonylation, Nat Chem Biol, 12(6): 396-398.*
Li et al., 2016, Molecular Coupling of Histone Crotonylation and Active Transcription by AF9 YEATS Domain, Mol Cell, 62(2): 181-193.*
Andrews, et al., "The Taf14 YEATS domain is a reader of histone crotonylation", Nat. Chem. Biol., 12(6):396-398 (2016).
Benner, "Expanding the genetic lexicon: incorporating non-standard amino acids into proteins by ribosome-based synthesis", TIB Tech, 12:158 163 (1994).
Cahill, et al., "Site-specific mutagenesis with unnatural amino acids", TIBS, 14(10):400 403 (1989).
Erb, et al., "Transcription control by the ENL YEATS domain in acute leukemia", Nature, 543:270-274(2017).
Ibba, "Strategies for in vitro and in vivo translation with non-natural amino acids", Biotechnology & Genetic Engineering Reviews, 13:197 216 (1995).
Ibba, et al., "Towards engineering proteins by site-directed incorporation in vivo of non-natural amino acids", Bio/technology, 12:678 682 (1994).
Jacques, et al., "Enantiomers, Racemates, and Resolutions," Wiley Interscience, (1981).
Li, et al., "Molecular Coupling of Histone Crotonylation and Active Transcription by AF9 YEATS Domain", Molecular Cell, 62:181-193 (2016).
Li, et al., "AF9 YEATS Domain Links Histone Acetylation to DOT1L-Mediated H3K79 Methylation", Cell, 159:558-571 (2014).
Pi Interaction, 5 pages, retrieved from https://en.wikipedia.org/w/index.php?title=Pi_interaction&oldid=747083242 (2016).
Pi-Stacking Interactions: Origin and Modulation, SED Group Meeting (2011).

(Continued)

*Primary Examiner* — Amber D Steele
(74) *Attorney, Agent, or Firm* — Pabst Patent Group LLP

(57) ABSTRACT

Disclosed herein are compositions and methods suitable for treating acute leukemia by inhibiting π π π stacking in the YEATS protein domain. YEATS protein domains are typically found in a variety of chromatin modification molecular complexes. Cancer cells are characterized by aberrant epigenetic landscapes and often exploit chromatin machinery to activate oncogenic gene expression programs. Quantitative analysis of the inhibitory activity of YEATS domain inhibitors by use of a fluorescence-based assay revealed that several of the tested inhibitors achieved 50% inhibition at the submicro/nanomolar level. As such, provided is the use of small molecule inhibitors that target the ENL YEATS domain to selectively kill leukemic MLL-r cells.

21 Claims, 33 Drawing Sheets
Specification includes a Sequence Listing.

(56) References Cited

OTHER PUBLICATIONS

Stacking (Chemistry), 8 pages, retrieved from https://en.wikipedia.org/w/index.php?title=Stacking_chemistry)&oldid=778922795 (2017).

Thorson, et al., "A Biosynthetic Approach for the Incorporation of Unnatural Amino Acids into Proteins", Methods in Molec. Biol., 77:43 73 (1991).

Wan, et al., "ENL links histone acetylation to oncogenic gene expression in acute myeloid leukemia", Nature, 543:265-269 (2017).

Zhang, et al., "Structural Insights into Histone Crotonyl-Lysine Recognition by the AF9 YEATS Domain", Structure, 24:1606-1612 (2016).

Zhao, et al., "YEATS2 is a selective histone crotonylation reader", Cell Research, 26:629-632 (2016).

Zoller, "New recombinant DNA methodology for protein engineering", Current Opinion in Biotechnology, 3:348 354 (1992).

\* cited by examiner

SEQUENCE LISTING

<160> NUMBER OF SEQ ID NOS: 49

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (10)..(10)
<223> OTHER INFORMATION: Amide modification on the C-terminus

<400> SEQUENCE: 1

Lys Gln Thr Ala Arg Lys Ser Thr Gly Gly
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: Amide modification on the C-terminus

<400> SEQUENCE: 2

Gln Thr Ala Arg Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(6)
<223> OTHER INFORMATION: Amide modification on the C-terminus

<400> SEQUENCE: 3

Lys Gln Thr Ala Arg Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Carboxybenzyl modification on the N-terminus
<220> FEATURE:
<221> NAME/KEY: MISC_FEATURE
<222> LOCATION: (5)..(5)
<223> OTHER INFORMATION: Amide modification on the C-terminus

<400> SEQUENCE: 4

Gln Thr Ala Arg Lys
1               5

<210> SEQ ID NO 5
<211> LENGTH: 6
<212> TYPE: PRT
<213> ORGANISM: Artificial Sequence

```
<220> FEATURE:
<223> OTHER INFORMATION: Synthetic Peptide

<400> SEQUENCE: 5

Lys Gln Thr Ala Arg Lys
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 6

Lys Gln Thr Ala Arg Lys Ser Thr Gly Gly
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = T, A or S
<222> LOCATION: (3)..(3)

<400> SEQUENCE: 7

Lys Gln Xaa Ala Arg Lys
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = T, A or S
<222> LOCATION: (3)..(3)

<400> SEQUENCE: 8

Lys Gln Xaa Ala Arg Lys Ser Thr Gly Gly
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = A, L or W
<222> LOCATION: (4)..(4)

<400> SEQUENCE: 9

Lys Gln Thr Xaa Arg Lys
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = A, L or W
<222> LOCATION: (4)..(4)
```

```
<400> SEQUENCE: 10

Lys Gln Thr Xaa Arg Lys Ser Thr Gly Gly
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = T, A, or S
<222> LOCATION: (3)..(3)
<220> FEATURE:
<221> NAME/KEY: Xaa = A, L or W
<222> LOCATION: (4)..(4)

<400> SEQUENCE: 11

Lys Gln Xaa Xaa Arg Lys
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa = T, A, or S
<222> LOCATION: (3)..(3)
<220> FEATURE:
<221> NAME/KEY: Xaa = A, L or W
<222> LOCATION: (4)..(4)

<400> SEQUENCE: 12

Lys Gln Xaa Xaa Arg Lys Ser Thr Gly Gly
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 13

Lys Gln Ala Ala Arg Lys
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 14

Lys Gln Ala Ala Arg Lys Ser Thr Gly Gly
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 15
```

```
Lys Gln Ser Ala Arg Lys
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 16

Lys Gln Ser Ala Arg Lys Ser Thr Gly Gly
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 17

Lys Gln Thr Trp Arg Lys
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 18

Lys Gln Thr Trp Arg Lys Ser Thr Gly Gly
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 19

Lys Gln Thr Leu Arg Lys
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 20

Lys Gln Thr Leu Arg Lys Ser Thr Gly Gly
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
```

```
<223> OTHER INFORMATION: Carboxybenzyl modification at N-terminus
<220> FEATURE:
<221> NAME/KEY: Xaa = R, K, Cit, or Q
<222> LOCATION: (4)..(4)
<220> FEATURE:
<221> NAME/KEY: MISC_FEATURE
<222> LOCATION: (5)..(5)
<223> OTHER INFORMATION: Amide modification at C-terminus

<400> SEQUENCE: 21

Gln Thr Ala Xaa Lys
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Carboxybenzyl modification at N-terminus
<220> FEATURE:
<221> NAME/KEY: Xaa = A, G, L, F, W, beta-Ala, or GABA
<222> LOCATION: (3)..(3)
<220> FEATURE:
<221> NAME/KEY: MISC_FEATURE
<222> LOCATION: (5)..(5)
<223> OTHER INFORMATION: Amide modification at C-terminus

<400> SEQUENCE: 22

Gln Thr Xaa Arg Lys
1               5

<210> SEQ ID NO 23
<211> LENGTH: 10
<212> TYPE: PRT
<213> ORGANISM: Artificial Sequence
<220> FEATURE:
<223> OTHER INFORMATION: Synthetic Peptide-based Inhibitor of the YEATS
      domain
<220> FEATURE:
<221> NAME/KEY: MISC_FEATURE
<222> LOCATION: (6)..(6)
<223> OTHER INFORMATION: Modified crotonyl group bonded to a
      trifluoromethyl group
<220> FEATURE:
<221> NAME/KEY: MISC_FEATURE
<222> LOCATION: (10)..(10)
<223> OTHER INFORMATION: Amide modification at the C-terminus

<400> SEQUENCE: 23

Lys Gln Thr Ala Arg Lys Ser Thr Gly Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide-based inhibitor of the YEATS
      domain
<220> FEATURE:
<221> NAME/KEY: MISC_FEATURE
<222> LOCATION: (6)..(6)
<223> OTHER INFORMATION: Modified crotonyl group bonded to a carbocyclic
      aromatic ring
<220> FEATURE:
<221> NAME/KEY: MISC_FEATURE
<222> LOCATION: (10)..(10)
<223> OTHER INFORMATION: Amide modification at C-terminus
```

```
<400> SEQUENCE: 24

Lys Gln Thr Ala Arg Lys Ser Thr Gly Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide-based inhibitor of the YEATS
      domain
<220> FEATURE:
<221> NAME/KEY: MISC_FEATURE
<222> LOCATION: (6)..(6)
<223> OTHER INFORMATION: modified crotonyl group with a pyridine
      carbonyl side chain
<220> FEATURE:
<221> NAME/KEY: MISC_FEATURE
<222> LOCATION: (10)..(10)
<223> OTHER INFORMATION: Amide modification at C-terminus

<400> SEQUENCE: 25

Lys Gln Thr Ala Arg Lys Ser Thr Gly Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic Peptide-based inhibitor of the YEATS
      domain
<220> FEATURE:
<221> NAME/KEY: MISC_FEATURE
<222> LOCATION: (6)..(6)
<223> OTHER INFORMATION: Modified crotonyl group bonded to a
      2-pyrimidinecarbonyl side chain
<220> FEATURE:
<221> NAME/KEY: MISC_FEATURE
<222> LOCATION: (10)..(10)
<223> OTHER INFORMATION: Amide modification at C-terminus

<400> SEQUENCE: 26

Lys Gln Thr Ala Arg Lys Ser Thr Gly Gly
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Peptide-based inhibitor of the YEATS
      domain
<220> FEATURE:
<221> NAME/KEY: MISC_FEATURE
<222> LOCATION: (6)..(6)
<223> OTHER INFORMATION: Modified crotonyl group bonded to
      2-furancarbonyl or 3-furancarbonyl side chain
<220> FEATURE:
<221> NAME/KEY: MISC_FEATURE
<222> LOCATION: (10)..(10)
<223> OTHER INFORMATION: Amide modification at C-terminus

<400> SEQUENCE: 27

Lys Gln Thr Ala Arg Lys Ser Thr Gly Gly
1               5                   10

<210> SEQ ID NO 28
<211> LENGTH: 10
<212> TYPE: PRT
<213> ORGANISM: Artificial Sequence
```

```
<220> FEATURE:
<223> OTHER INFORMATION: Synthetic peptide-based inhibitor of the YEATS
      domain
<220> FEATURE:
<221> NAME/KEY: MISC_FEATURE
<222> LOCATION: (6)..(6)
<223> OTHER INFORMATION: Modified crotonyl group with a
      2-thiophenecarbonyl or 3-thiophenecarbonyl side chain
<220> FEATURE:
<221> NAME/KEY: MISC_FEATURE
<222> LOCATION: (10)..(10)
<223> OTHER INFORMATION: Amide modification at C-terminus

<400> SEQUENCE: 28

Lys Gln Thr Ala Arg Lys Ser Thr Gly Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic peptide-based inhibitor of the YEATS
      domain
<220> FEATURE:
<221> NAME/KEY: MISC_FEATURE
<222> LOCATION: (6)..(6)
<223> OTHER INFORMATION: Modified crotonyl group bonded to a C5
      heterocyclic aromatic ring with nitrogen at position 1
<220> FEATURE:
<221> NAME/KEY: MISC_FEATURE
<222> LOCATION: (10)..(10)
<223> OTHER INFORMATION: Amide modification at C-terminus

<400> SEQUENCE: 29

Lys Gln Thr Ala Arg Lys Ser Thr Gly Gly
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic peptide-based inhibitor of the YEATS
      domain
<220> FEATURE:
<221> NAME/KEY: MISC_FEATURE
<222> LOCATION: (6)..(6)
<223> OTHER INFORMATION: Modified crotonyl group bonded to a
      5-oxazolecarbonyl or 4-oxazolecarbonyl side chain
<220> FEATURE:
<221> NAME/KEY: MISC_FEATURE
<222> LOCATION: (10)..(10)
<223> OTHER INFORMATION: Amide modification at C-terminus

<400> SEQUENCE: 30

Lys Gln Thr Ala Arg Lys Ser Thr Gly Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide-based inhibitor of the YEATS
      domain
<220> FEATURE:
<221> NAME/KEY: MISC_FEATURE
<222> LOCATION: (6)..(6)
<223> OTHER INFORMATION: Modified crotonyl group with attached
      isobenzofuran or benzothiophene-2-carbonyl side chain
<220> FEATURE:
<221> NAME/KEY: MISC_FEATURE
```

```
<222> LOCATION: (10)..(10)
<223> OTHER INFORMATION: Amide modification at C-terminus

<400> SEQUENCE: 31

Lys Gln Thr Ala Arg Lys Ser Thr Gly Gly
1               5                   10

<210> SEQ ID NO 32
<211> LENGTH: 4
<212> TYPE: PRT
<213> ORGANISM: Artificial Sequence
<220> FEATURE:
<223> OTHER INFORMATION: Synthetic peptide-based inhibitor of the YEATS
      domain
<220> FEATURE:
<221> NAME/KEY: MISC_FEATURE
<222> LOCATION: (2)..(2)
<223> OTHER INFORMATION: Modified crotonyl group with furancarbonyl side
      chain
<220> FEATURE:
<221> NAME/KEY: MISC_FEATURE
<222> LOCATION: (4)..(4)
<223> OTHER INFORMATION: Amide group at C-terminus

<400> SEQUENCE: 32

Arg Lys Ser Thr
1

<210> SEQ ID NO 33
<211> LENGTH: 5
<212> TYPE: PRT
<213> ORGANISM: Artificial Sequence
<220> FEATURE:
<223> OTHER INFORMATION: Synthetic Peptide-based inhibitor of the YEATS
      domain
<220> FEATURE:
<221> NAME/KEY: MISC_FEATURE
<222> LOCATION: (3)..(3)
<223> OTHER INFORMATION: Modified crotonyl group with furancarbonyl side
      chain
<220> FEATURE:
<221> NAME/KEY: MISC_FEATURE
<222> LOCATION: (5)..(5)
<223> OTHER INFORMATION: Amide modification at C-terminus

<400> SEQUENCE: 33

Ala Arg Lys Ser Thr
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic peptide-based inhibitor of the YEATS
      domain
<220> FEATURE:
<221> NAME/KEY: MISC_FEATURE
<222> LOCATION: (6)..(6)
<223> OTHER INFORMATION: Modified crotonyl group with furancarbonyl side
      chain
<220> FEATURE:
<221> NAME/KEY: MISC_FEATURE
<222> LOCATION: (6)..(6)
<223> OTHER INFORMATION: Amide group at C-terminus

<400> SEQUENCE: 34

Lys Gln Thr Ala Arg Lys
1               5

<210> SEQ ID NO 35
```

```
<211> LENGTH: 5
<212> TYPE: PRT
<213> ORGANISM: Artificial Sequence
<220> FEATURE:
<223> OTHER INFORMATION: Synthetic peptide-based inhibitor of YEATS
      domain
<220> FEATURE:
<221> NAME/KEY: MISC_FEATURE
<222> LOCATION: (1)..(1)
<223> OTHER INFORMATION: Carbobenzyl modification at N-terminus
<220> FEATURE:
<221> NAME/KEY: MISC_FEATURE
<222> LOCATION: (5)..(5)
<223> OTHER INFORMATION: Amide modification at C-terminus
<220> FEATURE:
<221> NAME/KEY: MISC_FEATURE
<222> LOCATION: (5)..(5)
<223> OTHER INFORMATION: Modified crotonyl group with attached
      furancarbonyl side chain

<400> SEQUENCE: 35

Gln Thr Ala Arg Lys
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Peptide-based inhibitor of YEATS
      domain
<220> FEATURE:
<221> NAME/KEY: MISC_FEATURE
<222> LOCATION: (1)..(1)
<223> OTHER INFORMATION: Carbobenzyl modification at N-terminus
<220> FEATURE:
<221> NAME/KEY: MISC_FEATURE
<222> LOCATION: (5)..(5)
<223> OTHER INFORMATION: Modified crotonyl group with attached
      5-oxazolecarbonyl side chain
<220> FEATURE:
<221> NAME/KEY: MISC_FEATURE
<222> LOCATION: (5)..(5)
<223> OTHER INFORMATION: Amide modification at C-terminus

<400> SEQUENCE: 36

Gln Thr Ala Arg Lys
1               5

<210> SEQ ID NO 37
<211> LENGTH: 11
<212> TYPE: PRT
<213> ORGANISM: Artificial Sequence
<220> FEATURE:
<223> OTHER INFORMATION: Synthetic Peptide-based inhibitor of YEATS
      domain
<220> FEATURE:
<221> NAME/KEY: MISC_FEATURE
<222> LOCATION: (6)..(6)
<223> OTHER INFORMATION: Modified crotonyl group with attached
      5-oxazolecarbonyl side chain
<220> FEATURE:
<221> NAME/KEY: MISC_FEATURE
<222> LOCATION: (11)..(11)
<223> OTHER INFORMATION: Amide modification at C-terminus

<400> SEQUENCE: 37

Thr Lys Ala Ala Arg Lys Ser Ala Pro Ala Thr
1               5                   10

<210> SEQ ID NO 38
<211> LENGTH: 10
<212> TYPE: PRT
```

```
<213> ORGANISM: Artificial Sequence
<220> FEATURE:
<223> OTHER INFORMATION: Synthetic Peptide-based inhibitor of YEATS
      domain
<220> FEATURE:
<221> NAME/KEY: MISC_FEATURE
<222> LOCATION: (5)..(5)
<223> OTHER INFORMATION: Modified crotonyl group with attached
      5-oxazolecarbonyl side chain
<220> FEATURE:
<221> NAME/KEY: MISC_FEATURE
<222> LOCATION: (10)..(10)
<223> OTHER INFORMATION: Amide modification at C-terminus

<400> SEQUENCE: 38

Lys Ala Ala Arg Lys Ser Ala Pro Ala Thr
1               5                   10

<210> SEQ ID NO 39
<211> LENGTH: 5
<212> TYPE: PRT
<213> ORGANISM: Artificial Sequence
<220> FEATURE:
<223> OTHER INFORMATION: Synthetic Peptide-based inhibitor of YEATS
      domain
<220> FEATURE:
<221> NAME/KEY: MISC_FEATURE
<222> LOCATION: (1)..(1)
<223> OTHER INFORMATION: Acetyl modification at N-terminus
<220> FEATURE:
<221> NAME/KEY: MISC_FEATURE
<222> LOCATION: (5)..(5)
<223> OTHER INFORMATION: Modified crotonyl group with attached
      furancarbonyl side chain
<220> FEATURE:
<221> NAME/KEY: MISC_FEATURE
<222> LOCATION: (5)..(5)
<223> OTHER INFORMATION: Amide modification at C-terminus

<400> SEQUENCE: 39

Lys Ala Ala Arg Lys
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Peptide-based inhibitor of YEATS
      domain
<220> FEATURE:
<221> NAME/KEY: MISC_FEATURE
<222> LOCATION: (1)..(1)
<223> OTHER INFORMATION: Carbobenzyl modification at N-terminus
<220> FEATURE:
<221> NAME/KEY: MISC_FEATURE
<222> LOCATION: (5)..(5)
<223> OTHER INFORMATION: Modified crotonyl group with attached
      furancarbonyl side chain
<220> FEATURE:
<221> NAME/KEY: MISC_FEATURE
<222> LOCATION: (5)..(5)
<223> OTHER INFORMATION: Carboxyl modification at C-terminus

<400> SEQUENCE: 40

Gln Thr Ala Arg Lys
1               5

<210> SEQ ID NO 41
<211> LENGTH: 5
<212> TYPE: PRT
<213> ORGANISM: Artificial Sequence
<220> FEATURE:
```

```
<223> OTHER INFORMATION: Synthetic Peptide-based inhibitor of YEATS
      domain
<220> FEATURE:
<221> NAME/KEY: MISC_FEATURE
<222> LOCATION: (1)..(1)
<223> OTHER INFORMATION: Carbobenzyl modification at N-terminus
<220> FEATURE:
<221> NAME/KEY: MISC_FEATURE
<222> LOCATION: (4)..(4)
<223> OTHER INFORMATION: X = K or Q
<220> FEATURE:
<221> NAME/KEY: MISC_FEATURE
<222> LOCATION: (5)..(5)
<223> OTHER INFORMATION: Modified crotonyl group with attached
      furancarbonyl side chain
<220> FEATURE:
<221> NAME/KEY: MISC_FEATURE
<222> LOCATION: (5)..(5)
<223> OTHER INFORMATION: Amide modification at C-terminus

<400> SEQUENCE: 41

Gln Thr Ala Xaa Lys
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Peptide-based inhibitor of YEATS
      domain
<220> FEATURE:
<221> NAME/KEY: MISC_FEATURE
<222> LOCATION: (1)..(1)
<223> OTHER INFORMATION: Carbobenzyl modification at N-terminus
<220> FEATURE:
<221> NAME/KEY: MISC_FEATURE
<222> LOCATION: (3)..(3)
<223> OTHER INFORMATION: X = Substitution for A; either G, L, F, W,
      Beta-Alanine or GABA
<220> FEATURE:
<221> NAME/KEY: MISC_FEATURE
<222> LOCATION: (5)..(5)
<223> OTHER INFORMATION: Modified crotonyl group with attached
      furancarbonyl side chain
<220> FEATURE:
<221> NAME/KEY: MISC_FEATURE
<222> LOCATION: (5)..(5)
<223> OTHER INFORMATION: Amide modification at C-terminus

<400> SEQUENCE: 42

Gln Thr Xaa Arg Lys
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Peptide-based inhibitor of YEATS
      domain
<220> FEATURE:
<221> NAME/KEY: MISC_FEATURE
<222> LOCATION: (1)..(1)
<223> OTHER INFORMATION: Carbobenzyl modification at N-terminus
<220> FEATURE:
<221> NAME/KEY: MISC_FEATURE
<222> LOCATION: (2)..(2)
<223> OTHER INFORMATION: X = V, A, L, S, or HoF
<220> FEATURE:
<221> NAME/KEY: MISC_FEATURE
<222> LOCATION: (5)..(5)
<223> OTHER INFORMATION: Modified crotonyl group with attached
      furancarbonyl side chain
<220> FEATURE:
```

```
<221> NAME/KEY: MISC_FEATURE
<222> LOCATION: (5)..(5)
<223> OTHER INFORMATION: Amide modification at C-terminus

<400> SEQUENCE: 43

Gln Xaa Ala Arg Lys
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Peptide-based inhibitor of YEATS
      domain
<220> FEATURE:
<221> NAME/KEY: MISC_FEATURE
<222> LOCATION: (1)..(1)
<223> OTHER INFORMATION: Carbobenzyl modification at N-terminus
<220> FEATURE:
<221> NAME/KEY: MISC_FEATURE
<222> LOCATION: (1)..(1)
<223> OTHER INFORMATION: X = E, A, N or Beta-Q
<220> FEATURE:
<221> NAME/KEY: MISC_FEATURE
<222> LOCATION: (5)..(5)
<223> OTHER INFORMATION: Modified crotonyl group with attached
      furancarbonyl side chain
<220> FEATURE:
<221> NAME/KEY: MISC_FEATURE
<222> LOCATION: (5)..(5)
<223> OTHER INFORMATION: Amide modification at C-terminus

<400> SEQUENCE: 44

Xaa Thr Ala Arg Lys
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Peptide-based inhibitor of YEATS
      domain
<220> FEATURE:
<221> NAME/KEY: MISC_FEATURE
<222> LOCATION: (1)..(1)
<223> OTHER INFORMATION: Carbobenzyl modification at N-terminus
<220> FEATURE:
<221> NAME/KEY: MISC_FEATURE
<222> LOCATION: (1)..(1)
<223> OTHER INFORMATION: E(OCH2Ph), D(OCH2Ph), E(NHPh) or D(NHPh) side
      chain at N-terminus
<220> FEATURE:
<221> NAME/KEY: MISC_FEATURE
<222> LOCATION: (5)..(5)
<223> OTHER INFORMATION: Modified crotonyl group with attached
      furancarbonyl side chain
<220> FEATURE:
<221> NAME/KEY: MISC_FEATURE
<222> LOCATION: (5)..(5)
<223> OTHER INFORMATION: Amide modification at C-terminus

<400> SEQUENCE: 45

Glu Thr Ala Arg Lys
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide-based inhibitor of the YEATS
```

```
                            domain
<220> FEATURE:
<221> NAME/KEY: MISC_FEATURE
<222> LOCATION: (1)..(1)
<223> OTHER INFORMATION: Extended aromatic ring structure at N-terminus
<220> FEATURE:
<221> NAME/KEY: MISC_FEATURE
<222> LOCATION: (5)..(5)
<223> OTHER INFORMATION: Modified crotonyl group with attached
      furancarbonyl side chain
<220> FEATURE:
<221> NAME/KEY: MISC_FEATURE
<222> LOCATION: (5)..(5)
<223> OTHER INFORMATION: Amide modification at C-terminus

<400> SEQUENCE: 46

Gln Thr Ala Arg Lys
1               5

<210> SEQ ID NO 47
<211> LENGTH: 4
<212> TYPE: PRT
<213> ORGANISM: Artificial Sequence
<220> FEATURE:
<223> OTHER INFORMATION: Synthetic competitor of the YEATS domain
<220> FEATURE:
<221> NAME/KEY: MISC_FEATURE
<222> LOCATION: (1)..(1)
<223> OTHER INFORMATION: Extended aromatic ring structure at N-terminus
<220> FEATURE:
<221> NAME/KEY: MISC_FEATURE
<222> LOCATION: (4)..(4)
<223> OTHER INFORMATION: Modified crotonyl group with attached
      furancarbonyl side chain
<220> FEATURE:
<221> NAME/KEY: MISC_FEATURE
<222> LOCATION: (4)..(4)
<223> OTHER INFORMATION: Amide modification at the C-terminus

<400> SEQUENCE: 47

Thr Ala Arg Lys
1

<210> SEQ ID NO 48
<211> LENGTH: 10
<212> TYPE: PRT
<213> ORGANISM: Artificial Sequence
<220> FEATURE:
<223> OTHER INFORMATION: Positive control - H3K9cr
<220> FEATURE:
<221> NAME/KEY: MISC_FEATURE
<222> LOCATION: (6)..(6)
<223> OTHER INFORMATION: Crotonyl side chain
<220> FEATURE:
<221> NAME/KEY: MISC_FEATURE
<222> LOCATION: (10)..(10)
<223> OTHER INFORMATION: Amide modification at C-terminus

<400> SEQUENCE: 48

Lys Gln Thr Ala Arg Lys Ser Thr Gly Gly
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic inhibitor of YEATS domain - Negative
      control XL-17
<220> FEATURE:
<221> NAME/KEY: MISC_FEATURE
<222> LOCATION: (6)..(6)
<223> OTHER INFORMATION: Modified crotonyl group with attached
```

```
      cyclopentanecarbonyl side chain
<220> FEATURE:
<221> NAME/KEY: MISC_FEATURE
<222> LOCATION: (10)..(10)
<223> OTHER INFORMATION: Amide modification at C-terminus

<400> SEQUENCE: 49

Lys Gln Thr Ala Arg Lys Ser Thr Gly Gly
1               5                   10
```

YEATS INHIBITORS AND METHODS OF USE THEREOF

CROSS-REFERENCE TO RELATED APPLICATIONS

This application is a National Phase application under 35 U.S.C. 371 of International Application No. PCT/CN2018/117418, filed Nov. 26, 2018, which claims priority to and benefit of U.S. Provisional Application No. 62/590,690, filed Nov. 27, 2017, and which are hereby incorporated herein by reference in their entirety.

FIELD OF THE INVENTION

The disclosed invention is generally in the field of functionalized oligomers and specifically in the area of functionalized peptides and peptide inhibitors.

REFERENCE TO SEQUENCE LISTING

The Sequence Listing submitted Aug. 18, 2022, as a text file named "UHK_00706_371_ST25.txt," created on Jul. 7, 2022, and having a size of 18,748 bytes is hereby incorporated by reference pursuant to 37 C.F.R. § 1.52(e)(5).

BACKGROUND OF THE INVENTION

Leukemia is a group of cancers that usually begin in the bone marrow and result in high numbers of abnormal, not fully developed white blood cells. Leukemias and lymphomas both belong to a broader group of tumors that affect the blood, bone marrow, and lymphoid system, known as tumors of the hematopoietic and lymphoid tissues. Acute leukemia is characterized by a rapid increase in the number of immature blood cells. The crowding that results from such cells makes the bone marrow unable to produce healthy blood cells. Acute leukemia requires immediate treatment because of the rapid progression and accumulation of the malignant cells, which then spill over into the bloodstream and spread to other organs of the body. Acute forms of leukemia are the most common forms of leukemia in children. Chronic leukemia is characterized by the excessive buildup of relatively mature, but still abnormal, white blood cells. Typically taking months or years to progress, the cells are produced at a much higher rate than normal, resulting in many abnormal white blood cells. Whereas acute leukemia must be treated immediately, chronic forms are sometimes monitored for some time before treatment to ensure maximum effectiveness of therapy. Chronic leukemia mostly occurs in older people, but can occur in any age group.

There are four main types of leukemia; acute lymphoblastic leukemia (ALL), acute myeloid leukemia (AML), chronic lymphocytic leukemia (CLL), and chronic myeloid leukemia (CML); as well as a number of less common types.

ALL is the most common type of leukemia in young children. However, it can also affect adults, especially those 65 and older. Subtypes of ALL include precursor B acute lymphoblastic leukemia, precursor T acute lymphoblastic leukemia, Burkitt's leukemia, and acute biphenotypic leukemia. AML occurs more commonly in adults than in children, and more commonly in men than women. Subtypes of AML include acute promyelocytic leukemia, acute myeloblastic leukemia, and acute megakaryoblastic leukemia. CLL most often affects adults over the age of 55, with two-thirds of affected individuals being men. Although it sometimes occurs in younger adults, it almost never affects children. One subtype of CLL is B-cell prolymphocytic leukemia, a more aggressive disease. CML also occurs mainly in adults, with only a very small number of children being affected. One subtype of CLL is chronic myelomonocytic leukemia.

Symptoms associated with most leukemias are due to a lack of normal blood cells, and may include bleeding and bruising problems, exhaustion, fever, and an increased risk of infections. Diagnosis is typically made by blood tests or bone marrow biopsy. Although the exact cause of leukemia is unknown, both inherited and environmental (non-inherited) factors are believed to be involved. Different kinds of leukemia are believed to have different causes. Risk factors include smoking, ionizing radiation, some chemicals (such as benzene), prior chemotherapy, and Down syndrome. People with a family history of leukemia are also at higher risk.

Treatment may involve some combination of chemotherapy, radiation therapy, targeted therapy, and bone marrow transplant, in addition to supportive care and palliative care as needed. Certain types of leukemia may be managed with watchful waiting. The success of treatment depends on the type of leukemia and the age of the person. Outcomes have improved in the developed world, with the average five-year survival rate being 57% in the United States. In children under 15, the five-year survival rate is greater than 60 to 85%, depending on the type of leukemia. In children with acute leukemia who are cancer-free after five years, the cancer is unlikely to return. As of 2015, leukemia was present in 2.3 million people and caused 353,500 deaths worldwide. It is the most common type of cancer in children, with three quarters of leukemia cases in children being of the acute lymphoblastic type. However, about 90% of all leukemias are diagnosed in adults, with AML and CLL being most common in adults. Leukemia occurs more commonly in the developed world.

Mixed lineage leukemia (MLL) is a very aggressive acute blood cancer that occurs predominantly in pediatric patients. In contrast to other types of childhood acute leukemias, MLL presents with a poor prognosis and despite the availability of advanced treatment methods, cure rates have been low over the past years. Available therapies for this well-characterized disease remain inadequate, prompting the need to identify new targets for therapeutic intervention.

It is an object of the invention to provide improved compositions for treating acute leukemia.

It is a further object of the invention to provide improved compositions which inhibit π-π-π stacking in the YEATS protein domain.

It is a further object of the invention to provide improved methods for treating acute leukemia.

BRIEF SUMMARY OF THE INVENTION

Disclosed herein are compositions and methods suitable for treating acute leukemia by inhibiting π-π-π stacking in the YEATS protein domain. YEATS protein domains are typically found in a variety of chromatin modification molecular complexes. The non-covalent interactions between aromatic rings in these domains are typically referred to as π stacking (or pi-stacking) interactions. The YEATS domains specifically recognize the lysine crotonylation marks on histones, accommodating the crotonyl group by forming π-π-π stacking using two conserved aromatic ring-containing amino acid residues.

Cancer cells are characterized by aberrant epigenetic landscapes and often exploit chromatin machinery to activate oncogenic gene expression programs. Mixed lineage leukemia (MLL) in particular is characterized by the presence of MLL fusion proteins that are the result of chromosomal translocations or rearrangements (MLL-r) affecting the MLL gene at 11q23.

Some leukemias involve abnormal hybrid proteins formed by the fusion of part of the protein MLL with a portion of a second protein. This second protein is often part of the super elongation complex (SEC) or the DOT1L-containing complex (DotCom), both of which modulate gene-transcription programs in MLL-rearranged leukemia. A protein called ENL associates with both complexes, and, in cells in which one copy of the complex is fused to MLL, interacts with both the fused and non-fused complexes. ENL contains a YEATS domain that binds to specific acetyl groups (Ac) on the protein histone H3—part of a histone complex around which DNA is packaged. The ENL YEATS domain helps to stabilize the association of SEC and Dot-Com with DNA, promoting leukemia-driving programs of gene expression (Erb et al. *Nature* 543:270-274 (2017); Wan et al. *Nature* 543:265-269 (2017)). Disrupting the interaction between the YEATS domain and histone acetylation via structure-based mutagenesis has previously been shown to reduce the recruitment of RNA polymerase II to ENL-target genes, leading to the suppression of oncogenic gene expression programs.

Quantitative analysis of the inhibitory activity of YEATS domain inhibitors by use of a fluorescence-based assay revealed that several of the tested inhibitors achieved 50% inhibition at the submicro/nanomolar level. As such, the present invention discloses the use of small molecule inhibitors that target π-π-π stacking interactions in the ENL YEATS domain to selectively kill leukemic MLL-r cells.

Disclosed are compositions and methods for treating a subject having acute leukemia. Generally, the compositions include linear or circular oligomers that include a base oligomer and a side chain. The side chain is generally designed or selected to include a conjugated/delocalized group. The oligomers generally can interact with a YEATS protein domain via the conjugated/delocalized group. It is believed that this interaction interferes with or inhibits π-π-π stacking interactions in the YEATS protein domain and that this has the desired YEATS inhibitory effect.

In preferred forms, the base oligomer is a peptide or peptide analog. Generally, the oligomer can be made up of bivalent linking units where the linking units are joined together via an appropriate linkage. The linkages can be, for example, amide, ester, thioester, thioamide, imidate, imide, sulfonate, or sulfonamide linkages. Different linkages in the oligomer can be the same or different, and can be made up of any combination of linkages. Preferred linkages are amide linkages. The linking units can be linked head-to-tail, head-to-head, tail-to-tail. Different linking units in the oligomer can be linked in the same orientation or in different orientations in any order. Preferred linking orientation is head-to-tail orientation. Different linking units in the oligomer can the same or different, and can be made up of any combination of linking units. Preferred linking units are α-amino acids.

In some forms, the composition includes a compound, or a pharmaceutically acceptable salt thereof, that comprises a base oligomer and a side chain. In some forms, the compound can be defined according to Formula (I):

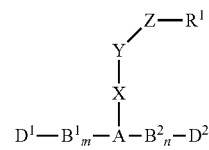

Formula (I)

where A can be $CR^2$ or N; where each instance of $B^1$ and $B^2$ can be an independently selected bivalent linking unit, where the linking units can be connected by amide, ester, thioester, thioamide, imidate, imide, sulfonate, or sulfonamide linkage; where the linking units can be linked in a head-to-tail manner; where $D^1$ can be H or unsubstituted or substituted hydrocarbyl, carbocyclyl or heterocyclyl; where $D^2$ can be H, $NH_2$, $NHR^{15}$, $NR^{16}R^{17}$, OH, $OR^{18}$, or unsubstituted or substituted hydrocarbyl, carbocyclyl or heterocyclyl; where X can be unsubstituted or substituted $C_{1-10}$ alkyl, $C_{1-10}$ alkenyl, $C_{1-10}$ alkynyl, C1-10 carbocyclyl, C1-10 heteroalkyl, C1-10 heteroalkenyl, C1-10 heteroalkynyl, or $C_{1-10}$ heterocyclyl; where Y can be $NR^3$, O, or S; where Z can be —CO—, —CS—, —$CNR^4$—, —SO—, or —$SO_2$—; where $R^{15}$, $R^{16}$, $R^{17}$, and $R^{18}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; where $R^2$, $R^3$, and $R^4$ can be independently H or $C_{1-10}$ hydrocarbyl, $C_{1-10}$ carbocyclyl, or $C_{1-10}$ heterocyclyl; where $R^1$ can be a conjugated/delocalized group. In some forms, the conjugated/delocalized group can be an unsubstituted or substituted, heterocyclic or carbocyclic, aromatic ring (such as monocyclic, bicyclic, tricyclic, tetracyclic) or unsubstituted or substituted alkenyl or alkynyl group, wherein the conjugated/delocalized group includes p-orbitals which allow for pi-electrons to become delocalized; and where m and n are each independently integers from 0 to 10. In some forms, at least one of m or n is not 0. In some forms, both of m or n are 0. In some forms, substituted hydrocarbyl can include acetyl.

In some forms, A can be $CR^2$ or N. In some forms, $R^2$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic. In some forms, A can be $CR^2$ and $R^2$ can be H.

In some forms, $B^1$ can be —NH—, —O—, —S—, or —$(CH_2)_p$—, where p is an integer from 1 to 6, for example 1, 2, 3, 4, 5, and 6. In some forms, the terminal $B^2$ can be —C(=O)—, —C(=NH)—, —C(=S)—, —S(=O)$_2$—, or -(representing a terminal bond on $B^2$). In some forms, $D^2$ can be H, $NH_2$, $NHR^{15}$, $NR^{16}R^{17}$, OH, $OR^{18}$, or unsubstituted or substituted hydrocarbyl, carbocyclyl or heterocyclyl, where $R^{15}$, $R^{16}$, $R^{17}$, and $R^{18}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic.

In some forms, the bivalent unit can be

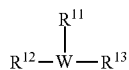

where W can be $CR^2$, $R^{11}$ can be a side chain, and $R^{12}$ and $R^{13}$ can be components of linkages such as amide linkages, ester linkages, thioester linkages, thioamine linkages, imidate linkages, imide linkages, sulfonate linkages, and sulfonamide linkages. Different bivalent units can be linked with the same or different types of linkages, with linked $R^{12}$ and $R^{13}$ groups being compatible components of the desired linkage. In some forms, $R^{12}$ can be $-C(=O)-R^{19}$, $-C(=NH)-R^{19}$, $-C(=S)-R^{19}$, or $-S(=O)_2-R^{19}$. In some forms, $R^{19}$ can be $N(R^{14})-$, $O-$, $S-$, or $N(R^{14})-C(=O)-$, where $R^{14}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic.

In some forms, $R^{11}$ can be made up in part of an existing or normal side chain of a monomer of the oligomer. Thus, for example, in a composition where the linear base oligomer is a peptide, one of the side chains of an amino acid in the peptide can comprise part of $R^{11}$ or can be replaced by $R^{11}$. In general, a composition of this form includes at least one $R^{11}$ terminating in $R^1$ (with $R^1$ as defined herein). In some forms, composition of this form includes at least one $R^{11}$ defined according to the following structure:

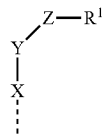

where the dashed line denotes the linkage point of the above structure and where $R^1$ can be a conjugated/delocalized group and X, Y, and Z are as defined herein.

In some forms, the bivalent units are all independently any α-amino acid. In some forms, the bivalent units are each an α-amino acid independently selected from the group consisting of Lys, Gln, Thr, Ala, Arg, Ser, Leu, Trp, and Gly.

In some forms, $D^1$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, $D^1$ can be H. In some forms, $D^1$ can be carboxybenzyl (Cbz). In some forms, $D^1$ can be acetyl. In some forms, $D^1$ can be benzenecarbonyl. In some forms, $D^1$ can be benzenemethylcarbonyl. In some forms, $D^1$ can be benzeneethylcarbonyl. In some forms, $D^1$ can be benzenepropylcarbonyl. In some forms, $D^1$ can be naphthalenemethylcarbonyl. In some forms, $D^1$ can be naphthaleneethylcarbonyl.

In some forms, $D^2$ can be H, $-NH_2$, $-NHR^{15}$, $-NR^{16}R^{17}$, $-OH$, $-OR^{18}$, or unsubstituted or substituted hydrocarbyl, carbocyclyl or heterocyclyl, where $R^{15}$, $R^{16}$, $R^{17}$, and $R^{18}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic. In some forms, $D^2$ can be H or $-NH_2$. In some forms, $D^2$ can be an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, $D^2$ can be H. In some forms, $D^2$ can be $-NH_2$. In some forms, $D^2$ can be OH or $OR^{18}$. In some forms, $D^2$ can be OH.

In some forms, X can be unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl. In some forms, X can be an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, X can be $-(CH_2)_p-$, where p is an integer from 1 to 6. In some forms, X can be $-(CH_2)_p-$, where p is an integer from 2 to 5. In some forms, X can be $-(CH_2)_p-$, where p is 3 or 4. In some forms, X can be $-(CH_2)_p-$, where p is 4.

In some forms, Y can be $-NR^3$, $-O-$, or $-S-$. In some forms, $R^3$ can be H or $C_{1-10}$ hydrocarbyl, $C_{1-10}$ carbocyclyl, or $C_{1-10}$ heterocyclyl. In some forms, $R^3$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms Y can be $NR^3$, and $R^3$ can be H.

In some forms, Z can be $-CO-$, $-CS-$, $-CNR^4-$, $-SO-$, or $-SO_2-$. In some forms, Z can be $-CO-$. In some forms, $R^4$ can be H or $C_{1-10}$ hydrocarbyl, $C_{1-10}$ carbocyclyl, or $C_{1-10}$ heterocyclyl. In some forms, $R^4$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group.

In some forms, the conjugated/delocalized group can be an unsubstituted or substituted, heterocyclic or carbocyclic, aromatic ring or unsubstituted or substituted alkenyl or alkynyl, wherein the conjugated/delocalized group includes p-orbitals which allow for pi-electrons to become delocalized. In some forms, the conjugated/delocalized group can be unsubstituted or substituted aromatic rings. In some forms, the conjugated/delocalized group can be unsubstituted or substituted aromatic monocyclic, bicyclic, tricyclic, or tetracyclic rings. In some forms, the conjugated/delocalized group can be unsubstituted or substituted alkenyl or alkynyl.

In some forms, $R^1$ can be an unsubstituted or substituted heterocyclic or carbocyclic, aromatic ring or unsubstituted or substituted alkenyl or alkynyl, wherein the conjugated/delocalized group includes p-orbitals which allow for pi-electrons to become delocalized. In some forms, $R^1$ can be unsubstituted or substituted aromatic rings. In some forms, $R^1$ can be unsubstituted or substituted aromatic monocyclic, bicyclic, tricyclic, or tetracyclic rings. In some forms, $R^1$ can be unsubstituted or substituted alkenyl or alkynyl. In some forms, $R^1$ can be:

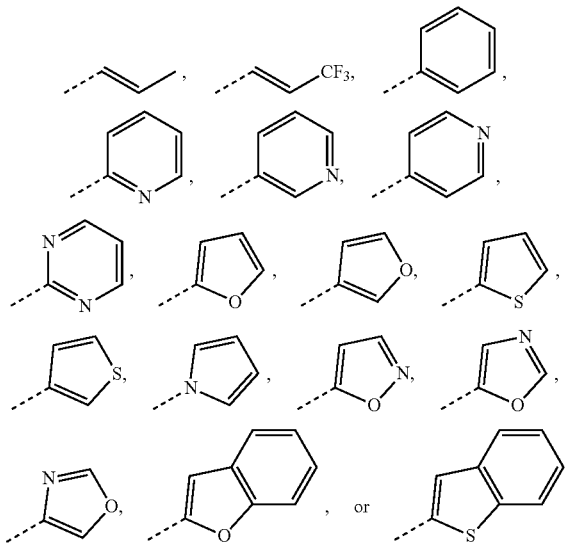

where the dashed lines denote the linkage point of the above structures.

In some forms, $R^1$ can be unsubstituted $C_6$ carbocyclic aromatic ring, such as an aryl group. In some forms, $R^1$ can be unsubstituted $C_6$ heterocyclic aromatic ring. In some forms, the unsubstituted $C_6$ heterocyclic aromatic ring can have nitrogen at any one of positions 2, 3, 4, 5, or 6. In some forms, the unsubstituted $C_6$ heterocyclic aromatic ring can have nitrogen at position 2. In some forms, the unsubstituted $C_6$ heterocyclic aromatic ring can have nitrogen at position 3. In some forms, the unsubstituted $C_6$ heterocyclic aromatic ring can have nitrogen at position 4.

In some forms, the unsubstituted $C_6$ heterocyclic aromatic ring can have nitrogen at any two of positions 2, 3, 4, 5, or 6. In some forms, the unsubstituted $C_6$ heterocyclic aromatic ring can have nitrogen at positions 2 and 5.

In some forms, $R^1$ can be unsubstituted $C_5$ carbocyclic aromatic ring. In some forms, $R^1$ can be unsubstituted $C_5$ heterocyclic aromatic ring. In some forms, the unsubstituted $C_5$ heterocyclic aromatic ring can have nitrogen at any one of positions 2, 3, 4, 5, or 1. In some forms, the unsubstituted $C_5$ heterocyclic aromatic ring can have nitrogen at any two of positions 2, 3, 4, 5, or 1. In some forms, the unsubstituted $C_5$ heterocyclic aromatic ring can have oxygen at any one of positions 2, 3, 4, 5, or 1. In some forms, the unsubstituted $C_5$ heterocyclic aromatic ring can have oxygen at position 2. In some forms, the unsubstituted $C_5$ heterocyclic aromatic ring can have oxygen at position 3.

In some forms, the unsubstituted $C_5$ heterocyclic aromatic ring can have sulfur at any one of positions 2, 3, 4, 5, or 1. In some forms, the unsubstituted $C_5$ heterocyclic aromatic ring can have sulfur at position 2. In some forms, the unsubstituted $C_5$ heterocyclic aromatic ring can have sulfur at position 3.

In some forms, the unsubstituted $C_5$ heterocyclic aromatic ring can have nitrogen or oxygen at any one of positions 2, 3, 4, 5, or 1. In some forms, the unsubstituted $C_5$ heterocyclic aromatic ring can have nitrogen or oxygen at position 1.

In some forms, the unsubstituted $C_5$ heterocyclic aromatic ring can have nitrogen or oxygen independently at any two of positions 2, 3, 4, 5, or 1. In some forms, the unsubstituted $C_5$ heterocyclic aromatic ring can have oxygen at any one of positions 2, 3, 4, 5, or 1 and nitrogen at any one of positions 2, 3, 4, or 1 not occupied by oxygen. In some forms, the unsubstituted $C_5$ heterocyclic aromatic ring can have oxygen at position 2 and nitrogen at position 3. In some forms, the unsubstituted $C_5$ heterocyclic aromatic ring can have oxygen at position 2 and nitrogen at position 4. In some forms, the unsubstituted $C_5$ heterocyclic aromatic ring can have oxygen at position 3 and nitrogen at position 5.

In some forms, the unsubstituted $C_5$ heterocyclic aromatic ring can have nitrogen at any one of positions 2, 3, 4, 5, or 1 and oxygen at any one of positions 2, 3, 4, or 1 not occupied by nitrogen.

In some forms, $R^1$ can be unsubstituted $C_9$ bicyclic carbocyclic aromatic ring. In some forms, $R^1$ can be unsubstituted $C_9$ bicyclic heterocyclic aromatic ring. In some forms, the unsubstituted $C_9$ bicyclic heterocyclic aromatic ring can have nitrogen at any one of positions 1, 2, 3, 4, 5, 6, 7, 8, or 9. In some forms, the unsubstituted $C_9$ bicyclic heterocyclic aromatic ring can have nitrogen at any two of positions 1, 2, 3, 4, 5, 6, 7, 8, or 9.

In some forms, the unsubstituted $C_9$ bicyclic heterocyclic aromatic ring can have oxygen at any one of positions 2, 3, 4, 5, 7, 8, or 9. In some forms, the unsubstituted $C_9$ bicyclic heterocyclic aromatic ring can have oxygen at position 7.

In some forms, the unsubstituted $C_9$ bicyclic heterocyclic aromatic ring can have sulfur at any one of positions 2, 3, 4, 5, 7, 8, or 9. In some forms, the unsubstituted $C_9$ bicyclic heterocyclic aromatic ring can have sulfur at position 7.

In some forms, the unsubstituted $C_9$ bicyclic heterocyclic aromatic ring can have nitrogen at any one of positions 1, 2, 3, 4, 5, 6, 7, 8, or 9 or oxygen at any one of positions 2, 3, 4, 5, 7, 8, or 9. In some forms, the unsubstituted $C_9$ bicyclic heterocyclic aromatic ring can have nitrogen or oxygen independently at any two of positions 1, 2, 3, 4, 5, 6, 7, 8, or 9. In some forms, the unsubstituted $C_9$ bicyclic heterocyclic aromatic ring can have oxygen at any one of positions 2, 3, 4, 5, 7, 8, or 9 and nitrogen at any one of positions 1, 2, 3, 4, 6, 7, 8, or 9 not occupied by oxygen. In some forms, the unsubstituted $C_9$ bicyclic heterocyclic aromatic ring can have nitrogen at any one of positions 1, 2, 3, 4, 5, 6, 7, 8, or 9 and oxygen at any one of positions 2, 3, 4, 7, 8, or 9 not occupied by nitrogen.

In some forms, m is an integer from 0 to 10. In some forms, m can be 0, 1, 2, 3, 4, 5, 6, 7, 8, 9, or 10. In some forms, n is an integer from 0 to 10. In some forms, n can be 0, 1, 2, 3, 4, 5, 6, 7, 8, 9, or 10. In some forms, m+n can be an integer from 0 to 20. In some forms, m+n can be 0, 1, 2, 3, 4, 5, 6, 7, 8, 9, 10, 11, 12, 13, 14, 15, 16, 17, 18, 19, or 20.

In some forms, the compound can be defined according to Formula (II):

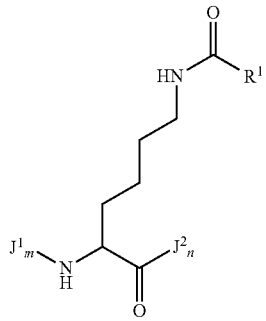

Formula (II)

where each instance of $J^1$ and $J^2$ is independently any α-amino acid; where $R^1$ is a conjugated/delocalized group, comprising an unsubstituted or substituted, heterocyclic or carbocyclic, aromatic ring (monocyclic, bicyclic, tricyclic, tetracyclic), or unsubstituted or substituted alkenyl or alkynyl, wherein the conjugated/delocalized group includes p-orbitals which allow for pi-electrons to become delocalized; and where m and n are each independently integers from 0 to 10. In some forms, at least one of m or n is not 0. In some forms, both of m or n are 0.

In some forms, the compound can be defined according to Formula (III):

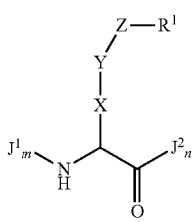

Formula (III)

where each instance of $J^1$ and $J^2$ is independently any α-amino acid; where X is an unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl; where Y is $NR^3$, O, or S; where Z is —CO—, —CS—, —$CNR^4$—, —SO—, and —$SO_2$—; where $R^3$ and $R^4$ are independently H or $C_{1-10}$ hydrocarbyl, $C_{1-10}$ carbocyclyl or $C_{1-10}$ heterocyclyl; where $R^1$ is a conjugated/delocalized group, such as an unsubstituted or substituted, heterocyclic or carbocyclic, aromatic ring (monocyclic, bicyclic, tricyclic, tetracyclic), unsubstituted or substituted alkenyl or alkynyl, wherein the conjugated/delocalized group includes overlapping p-orbitals which allow for pi-electrons to become delocalized; and where m and n are each independently integers from 0 to 10. In some forms, at least one of m or n is not 0. In some forms, both of m or n are 0.

In some forms, the compound can be defined according to Formula (IV):

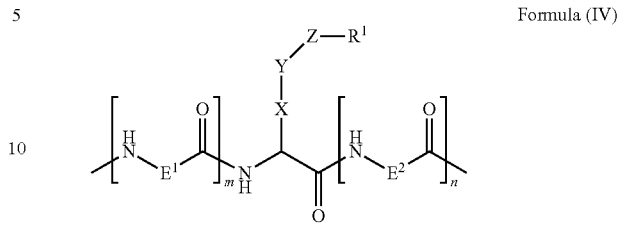

Formula (IV)

where each instance of $E^1$ and $E^2$ is independently an unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl, or O, S, or $NR^5$; where X is an unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl; where Y is $NR^3$, O, or S; where Z is —CO—, —CS—, —$CNR^4$—, —SO—, or —$SO_2$—; where $R^3$, $R^4$, and $R^5$ are independently a H, $C_{1-10}$ hydrocarbyl, $C_{1-10}$ carbocyclyl or $C_{1-10}$ heterocyclyl; where $R^1$ is a conjugated/delocalized group, such as an unsubstituted or substituted, heterocyclic or carbocyclic, aromatic ring (monocyclic, bicyclic, tricyclic, tetracyclic) or unsubstituted or substituted alkenyl or alkynyl, wherein the conjugated/delocalized group includes p-orbitals which allow for pi-electrons to become delocalized; and where m and n are each independently integers from 0 to 10. In some forms, at least one of m or n is not 0. In some forms, both of m or n are 0.

In some forms of the compound, at least two of the instances of $B^1$ linking units can comprise side chains, where two of the side chains of the $B^1$ linking units can be covalently coupled to each other forming a circular oligomer.

In some forms of the compound, at least two of the instances of $B^2$ linking units can comprise side chains, where two of the side chains of the $B^2$ linking units can be covalently coupled to each other forming a circular oligomer.

In some forms of the compound, at least one of the instances of $B^1$ linking units and at least one of the instances of $B^2$ linking units can comprise side chains, where two of the side chains of the $B^1$ and $B^2$ linking units can be covalently coupled to each other forming a circular oligomer.

In some forms of the compound, at least two of the instances of $J^1$ amino acids can comprise side chains, where two of the side chains of the $J^1$ amino acids can be covalently coupled to each other forming a circular oligomer.

In some forms of the compound, at least two of the instances of $J^2$ amino acids can comprise side chains, where two of the side chains of the $J^2$ amino acids can be covalently coupled to each other forming a circular oligomer.

In some forms of the compound, at least one of the instances of $J^1$ amino acids and at least one of the instances of $J^2$ amino acids can comprise side chains, where two of the side chains of the $J^1$ and $J^2$ amino acids can be covalently coupled to each other forming a circular oligomer.

In some forms of the compound, at least two of the instances of $E^1$ can comprise side chains, where two of the side chains of the $E^1$ can be covalently coupled to each other forming a circular oligomer.

In some forms of the compound, at least two of the instances of $E^2$ can comprise side chains, where two of the side chains of the $E^2$ can be covalently coupled to each other forming a circular oligomer.

In some forms of the compound, at least one of the instances of $E^1$ and at least one of the instances of $E^2$ can comprise side chains, where two of the side chains of the $E^1$ and $E^2$ can be covalently coupled to each other forming a circular oligomer.

In some forms, the compound can be defined according to Formula (V):

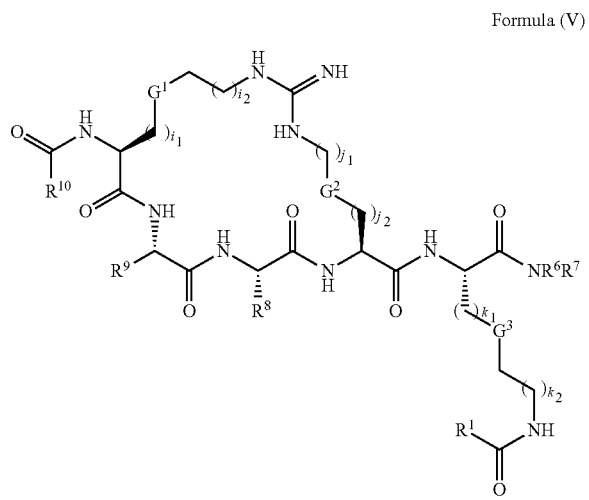

Formula (V)

where $R^1$ is a conjugated/delocalized group, comprising an unsubstituted or substituted, heterocyclic or carbocyclic, aromatic ring (monocyclic, bicyclic, tricyclic, tetracyclic) or unsubstituted or substituted alkenyl or alkynyl, wherein the conjugated/delocalized group includes overlapping p-orbitals which allow for pi-electrons to become delocalized; where $R^6$, $R^7$, $R^8$, $R^9$, and $R^{10}$ are independently H or $C_{1-10}$ hydrocarbyl, $C_{1-10}$ carbocyclyl or $C_{1-10}$ heterocyclyl; where each of $G^1$, $G^2$, and $G^3$ is an unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, $C_{1-10}$ heterocyclyl, or $C_{5-9}$ heteroaryl; and where $i_1, i_2, j_1, j_2, k_1, k_2$ are each independently integers from 0 to 10.

In some forms, $R^8$ and $R^9$ are the side chains of an amino acid, which can be independently selected from the side chains of the amino acids Lys, Gln, Thr, Ala, Arg, Ser, Leu, Trp, and Gly.

In some forms, $R^{10}$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, $R^{10}$ can be H. In some forms, $R^{10}$ can be carboxybenzyl (Cbz). In some forms, $R^{10}$ can be acetyl. In some forms, $R^{10}$ can be benzenecarbonyl. In some forms, $R^{10}$ can be benzenemethylcarbonyl. In some forms, $R^{10}$ can be benzeneethylcarbonyl. In some forms, $R^{10}$ can be benzenepropylcarbonyl. In some forms, $R^{10}$ can be naphthalenemethylcarbonyl. In some forms, $R^{10}$ can be naphthaleneethylcarbonyl.

In some forms, $i_1$ is an integer from 0 to 10. In some forms, $i_1$ can be 0, 1, 2, 3, 4, 5, 6, 7, 8, 9, or 10. In some forms, $i_2$ is an integer from 0 to 10. In some forms, $i_2$ can be 0, 1, 2, 3, 4, 5, 6, 7, 8, 9, or 10. In some forms, $j_1$ is an integer from 0 to 10. In some forms, $j_1$ can be 0, 1, 2, 3, 4, 5, 6, 7, 8, 9, or 10. In some forms, $j_2$ is an integer from 0 to 10. In some forms, $j_2$ can be 0, 1, 2, 3, 4, 5, 6, 7, 8, 9, or 10. In some forms, $k_1$ is an integer from 0 to 10. In some forms, $k_i$ can be 0, 1, 2, 3, 4, 5, 6, 7, 8, 9, or 10. In some forms, $k_2$ is an integer from 0 to 10. In some forms, $k_2$ can be 0, 1, 2, 3, 4, 5, 6, 7, 8, 9, or 10.

In some forms, the compound inhibits π-π-π stacking interactions. In some forms, the compound selectively targets the YEATS protein domain and π-π-π stacking interactions therein.

Also disclosed are pharmaceutical compositions comprising an effective amount of any of the disclosed compounds. In some forms, the composition can further comprise one or more pharmaceutically acceptable carriers or excipients. In some forms, the composition selectively inhibits π-π-π stacking interactions. In some forms, the composition selectively targets the YEATS protein domain. In some forms, the composition is effective for treating cancer. In some forms, the cancer is acute leukemia.

Also disclosed are methods for treating cancer, the method comprising administering any of the disclosed compositions to a subject in need thereof. In some forms, the subject has acute leukemia.

Disclosed are compositions and methods for treating a subject having acute leukemia. In some forms, the composition is an inhibitor compound, which includes a linear base oligomer, such as a peptide, and a side chain according to Formula (I):

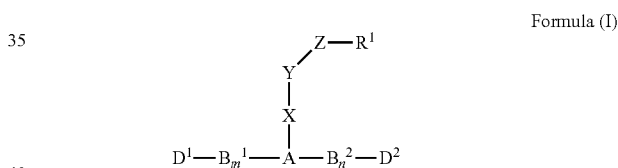

Formula (I)

where A is N or $CR^2$; each of $B^1$ and $B^2$ are independently bivalent linking groups that connect each unit by ester, amide, thioester, thioamide, imidate, imide, sulfonate, sulfonamide linkage in a head-to-tail manner; $D^1$ can be H or unsubstituted or substituted hydrocarbyl, carbocyclyl or heterocyclyl; $D^2$ can be H, $NH_2$, $NHR^{15}$, $NR^{16}R^{17}$, OH, $OR^{18}$, or unsubstituted or substituted hydrocarbyl, carbocyclyl or heterocyclyl; X is an unsubstituted or substituted $C_{1-10}$ alkyl, $C_{1-10}$ alkenyl, $C_{1-10}$ alkynyl, $C_{1-10}$ carbocyclyl or $C_{1-10}$ heteroalkyl, $C_{1-10}$ heteroalkenyl, $C_{1-10}$ heteroalkynyl, or $C_{1-10}$ heterocyclyl; Y is O, S or $NR^3$; Z is —CO—, —CS—, —$CNR^4$—, —SO—, and —$SO_2$—; $R^{15}$, $R^{16}$, $R^{17}$, and $R^{18}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; $R^2$, $R^3$, and $R^4$ are independently a H, $C_{1-10}$ hydrocarbyl, $C_{1-10}$ carbocyclyl or $C_{1-10}$ heterocyclyl; $R^1$ is a conjugated/delocalized group, including unsubstituted or substituted aromatic rings (monocyclic, bicyclic, tricyclic, tetracyclic), unsubstituted or substituted alkenyl or alkynyl, wherein the conjugated/delocalized group includes overlapping p-orbitals which allow for pi-electrons to become delocalized; and m and n are integers from 0 to 10. In some forms, at least one of m or n is not 0. In some forms, both of m or n are 0. The side chain can be made up in part of an existing or normal side chain of a monomer of the oligomer. Thus, for example, in a composition where the linear base oligomer is a peptide, one of the side chains of an amino acid in the peptide can comprise part of the side chain or can be replaced by the side chain.

In some forms, $B^1$ can be —NH—, —O—, —S—, or —$(CH_2)_p$—, where p is an integer from 1 to 6, for example 1, 2, 3, 4, 5, and 6. In some forms, the terminal $B^2$ can be —C(=O)—, —C(=NH)—, —C(=S)—, —S(=O)$_2$—, or -(representing a terminal bond on $B^2$). In some forms, $D^2$ can be H, $NH_2$, $NHR^{15}$, $NR^{16}R^{17}$, OH, $OR^{18}$, or unsubstituted or substituted hydrocarbyl, carbocyclyl or heterocyclyl, where $R^{15}$, $R^{16}$, $R^{17}$, and $R^{18}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic.

In other forms, the composition is an inhibitor compound, which includes a linear base peptide and a side chain according to Formula (II):

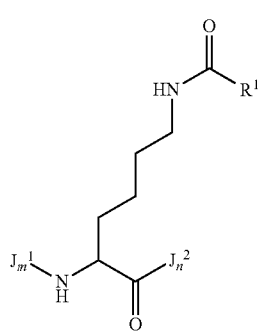

Formula (II)

where each of $J^1$ and $J^2$ are independently any α-amino acids; R is a conjugated/delocalized group, comprising unsubstituted or substituted aromatic rings (monocyclic, bicyclic, tricyclic, tetracyclic), unsubstituted or substituted alkenyl or alkynyl, wherein the conjugated/delocalized group includes overlapping p-orbitals which allow for pi-electrons to become delocalized; and m and n are integers from 0 to 10. In some forms, at least one of m or n is not 0. In some forms, both of m or n are 0.

In other forms, the composition is an inhibitor compound, which includes a linear base peptide and a side chain according to Formula (III):

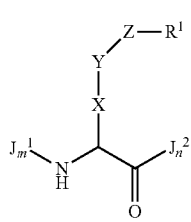

Formula (III)

where each of $J^1$ and $J^2$ are independently any α-amino acid; X is an unsubstituted or substituted $C_{1-10}$ alkyl, $C_{1-10}$ alkenyl, $C_{1-10}$ alkynyl, $C_{1-10}$ carbocyclyl or $C_{1-10}$ heteroalkyl, $C_{1-10}$ heteroalkenyl, $C_{1-10}$ heteroalkynyl, or $C_{1-10}$ heterocyclyl; Y is O, S or $NR^2$; Z is —CO—, —CS—, —$CNR^3$—, —SO—, and —$SO_2$—; $R^2$, $R^3$ are independently a H, $C_{1-10}$ hydrocarbyl, $C_{1-10}$ carbocyclyl or $C_{1-10}$ heterocyclyl; $R^1$ is a conjugated/delocalized group, including unsubstituted or substituted aromatic rings (monocyclic, bicyclic, tricyclic, tetracyclic), unsubstituted or substituted alkenyl or alkynyl, wherein the conjugated/delocalized group includes overlapping p-orbitals which allow for pi-electrons to become delocalized; and m and n are integers from 0 to 10. In some forms, at least one of m or n is not 0. In some forms, both of m or n are 0.

In other forms, the composition is an inhibitor compound, which includes a linear base peptide and a side chain according to Formula (IV):

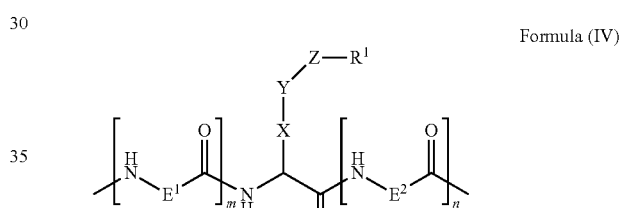

Formula (IV)

where each of $E^1$ and $E^2$ is independently a 0, S, $NR^2$, unsubstituted or substituted $C_{1-10}$ $C_{1-10}$ alkyl, $C_{1-10}$ alkenyl, $C_{1-10}$ alkynyl, $C_{1-10}$ carbocyclyl or $C_{1-10}$ heteroalkyl, $C_{1-10}$ heteroalkenyl, $C_{1-10}$ heteroalkynyl, or $C_{1-10}$ heterocyclyl; X is an unsubstituted or substituted $C_{1-10}$ alkyl, $C_{1-10}$ alkenyl, $C_{1-10}$ alkynyl, $C_{1-10}$ carbocyclyl or $C_{1-10}$ heteroalkyl, $C_{1-10}$ heteroalkenyl, $C_{1-10}$ heteroalkynyl, or $C_{1-10}$ heterocyclyl; Y is O, S or $NR^3$; Z is —CO—, —CS—, —$CNR^4$—, —SO—, or —$SO_2$—; $R^2$, $R^3$, and $R^4$ are independently a H, $C_{1-10}$ hydrocarbyl, $C_{1-10}$ carbocyclyl or $C_{1-10}$ heterocyclyl; $R^1$ is a conjugated/delocalized group, including unsubstituted or substituted aromatic rings (monocyclic, bicyclic, tricyclic, tetracyclic), unsubstituted or substituted alkenyl or alkynyl, wherein the conjugated/delocalized group includes overlapping p-orbitals which allow for pi-electrons to become delocalized; and m and n are integers from 0 to 10. In some forms, at least one of m or n is not 0. In some forms, both of m or n are 0.

In alternative forms, the composition is an inhibitor compound, which includes a cyclic peptide and is defined according to Formula (V):

Formula (V)

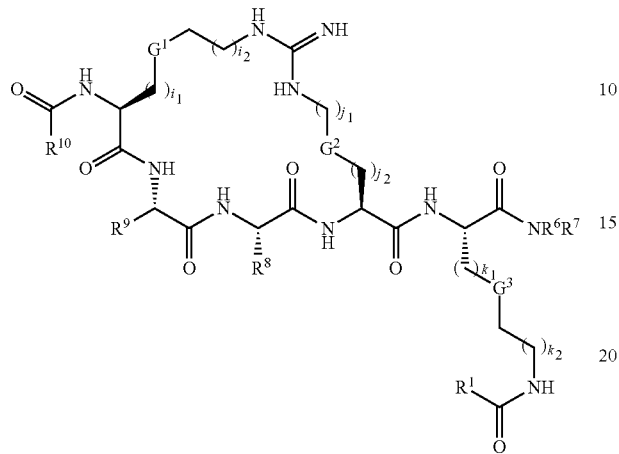

where $R^1$ is a conjugated/delocalized group, comprising unsubstituted or substituted aromatic rings (monocyclic, bicyclic, tricyclic, tetracyclic), unsubstituted or substituted alkenyl or alkynyl, wherein the conjugated/delocalized group includes overlapping p-orbitals which allow for pi-electrons to become delocalized; $R^6$, $R^7$, $R^8$, $R^9$, and $R^{10}$ are independently a H, $C_{1-10}$ hydrocarbyl, $C_{1-10}$ carbocyclyl or $C_{1-10}$ heterocyclyl; each of $G^1$, $G^2$, and $G^3$ is an unsubstituted or substituted $C_{1-10}$ alkyl, $C_{1-10}$ alkenyl, $C_{1-10}$ alkynyl, $C_{1-10}$ carbocyclyl or $C_{1-10}$ heteroalkyl, $C_{1-10}$ heteroalkenyl, $C_{1-10}$ heteroalkynyl, $C_{1-10}$ heterocyclyl, or $C_{5-9}$ heteraryl; and $i_1$, $i_2$, $j_1$, $j_2$, $k_1$, $k_2$ are integers from 0 to 10.

In some forms, $R^8$ and $R^9$ are the side chains of an amino acid, which can be independently selected from the side chains of the amino acids Lys, Gln, Thr, Ala, Arg, Ser, Leu, Trp, and Gly.

In some forms, $R^{10}$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, $R^{10}$ can be H. In some forms, $R^{10}$ can be carboxybenzyl (Cbz). In some forms, $R^{10}$ can be acetyl. In some forms, $R^{10}$ can be benzenecarbonyl. In some forms, $R^{10}$ can be benzenemethylcarbonyl. In some forms, $R^{10}$ can be benzeneethylcarbonyl. In some forms, $R^{10}$ can be benzenepropylcarbonyl. In some forms, $R^{10}$ can be naphthalenemethylcarbonyl. In some forms, $R^{10}$ can be naphthaleneethylcarbonyl.

In other forms, the composition is an inhibitor compound, which includes a linear base peptide and a side chain according to Formula (VI):

Formula (VI)

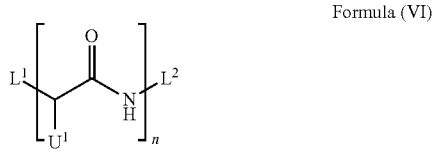

where n is an integer greater than 1, preferably in the range of 2-10; $L^1$ and $L^2$ are independently selected from a hydrogen, —$NH_2$, unsubstituted or substituted $C_{1-10}$ alkyl, $C_{1-10}$ alkenyl, $C_{1-10}$ alkynyl, $C_{3-10}$ carbocyclyl, $C_{1-10}$ heteroalkyl, $C_{1-10}$ heteroalkenyl, $C_{1-10}$ heteroalkynyl, or $C_{3-10}$ heterocyclyl. In some forms, $L^1$ is preferably an —$NH_2$ group.

In some forms of compounds of Formula (VI), $L^2$ is selected from a hydrogen or the following group:

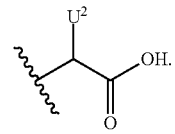

In some forms of compounds of Formula (VI), $U^1$ and $U^2$ are each independently selected from the following groups: a proline structure,

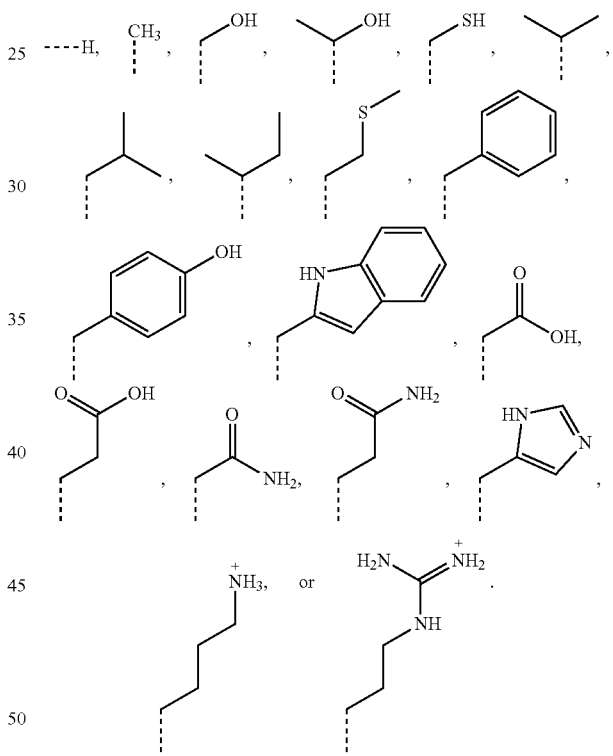

where the dashed lines denote the linkage point of the above groups.

In some instances, $U^1$ may form a proline structure, where $U^1$ is a $C_3$ alkyl that forms a cyclic structure with the nitrogen of the NH group shown in the bracketed repeating unit of the inhibitor of Formula (IV) and the hydrogen of the NH group is absent. In some instances, $U^2$ may form a proline structure, where $U^2$ is a $C_3$ alkyl that forms a cyclic structure with the nitrogen of the NH group shown in the bracketed repeating unit of the inhibitor of Formula (IV) and the hydrogen of the NH group is absent.

The compounds of Formula (VI) include at least one $U^1$ or $U^2$ group which is defined according to the following structure:

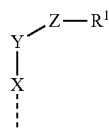

where the dashed line denotes the linkage point of above structure and where $R^1$ can be a conjugated/delocalized group. In some forms, the conjugated/delocalized group can be an unsubstituted or substituted, heterocyclic or carbocyclic, aromatic ring (such as monocyclic, bicyclic, tricyclic, tetracyclic) or unsubstituted or substituted alkenyl or alkynyl group, wherein the conjugated/delocalized group includes p-orbitals which allow for pi-electrons to become delocalized.

In some forms of compounds of Formula (VI), X can be unsubstituted or substituted $C_{1-10}$ alkyl, $C_{1-10}$ alkenyl, $C_{1-10}$ alkynyl, $C_{3-10}$ carbocyclyl, $C_{1-10}$ heteroalkyl, $C_{1-10}$ heteroalkenyl, $C_{1-10}$ heteroalkynyl, or $C_{3-10}$ heterocyclyl. In some forms, X can be an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, X can be —$(CH_2)_p$—, where p is an integer from 1 to 6. In some forms, X can be —$(CH_2)_p$—, where p is an integer from 2 to 5. In some forms, X can be —$(CH_2)_p$—, where p is 3 or 4. In some forms, X can be —$(CH_2)_p$—, where p is 4.

In some forms of compounds of Formula (VI), Y can be —$NR^3$, —O—, or —S—. In some forms, $R^3$ can be H or $C_{1-10}$ hydrocarbyl, $C_{3-10}$ carbocyclyl, or $C_{3-10}$ heterocyclyl. In some forms, $R^3$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms Y can be $NR^3$, and $R^3$ can be H.

In some forms of compounds of Formula (VI), Z can be —CO—, —CS—, —$CNR^4$—, —SO—, or —$SO_2$—. In some forms, Z can be —CO—. In some forms, $R^4$ can be H or $C_{1-10}$ hydrocarbyl, $C_{3-10}$ carbocyclyl, or $C_{3-10}$ heterocyclyl. In some forms, $R^4$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group.

In yet other forms, the composition is an inhibitor compound, which includes a linear base peptide and a side chain according to Formula (VII):

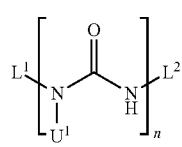

Formula (VII)

where n, $L^1$, $L^2$, $U^1$, and $U^2$ groups are defined in the same manner as in Formula (VI) and include at least one $U^1$ or $U^2$ group which defined according to the following structure:

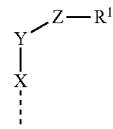

where the dashed line denotes the linkage point of above structure and wherein X, Y, Z, and $R^1$ are defined in the same manner as in Formula (VI).

In still some other forms, the composition is an inhibitor compound, which includes a linear base peptide and a side chain according to Formula (VIII):

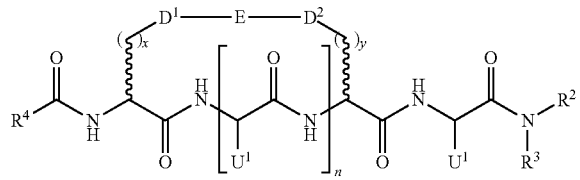

Formula (VIII)

where n is an integer greater than 1, preferably in the range of 2-10; and x and y are independently integers from 1-10. The compounds of Formula (VIII) include $U^1$ groups as defined in Formula (VI) and include at least one $U^1$ group defined according to the following structure:

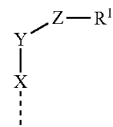

where the dashed line denotes the linkage point of above structure and wherein X, Y, Z, and $R^1$ are defined in the same manner as in Formula (VI).

In some forms of compounds of Formula (VIII), $R^2$ and $R^3$ are each independently selected from a hydrogen, $C_{1-10}$ hydrocarbyl, $C_{3-10}$ carbocyclyl, or $C_{3-10}$ heterocyclyl; and $R^4$ is selected from a hydrogen, —OH, —$NH_2$, $C_{1-10}$ hydrocarbyl, $C_{3-10}$ carbocyclyl, or $C_{3-10}$ heterocyclyl.

In some forms of compounds of Formula (VIII), $D^1$ and $D^2$ are each independently selected from an unsubstituted or substituted $C_{1-10}$ alkyl, $C_{1-10}$ alkenyl, $C_{1-10}$ alkynyl, $C_{3-10}$ carbocyclyl, $C_{1-10}$ heteroalkyl, $C_{1-10}$ heteroalkenyl, $C_{1-10}$ heteroalkynyl, or $C_{3-10}$ heterocyclyl; and E is defined according to the following structure:

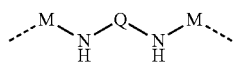

where the dashed lines denote the linkage point of above structure and where each M can independently be an unsubstituted or substituted $C_{1-10}$ alkyl, $C_{1-10}$ alkenyl, $C_{1-10}$ alkynyl, $C_{3-10}$ carbocyclyl, $C_{1-10}$ heteroalkyl, $C_{1-10}$ heteroalkenyl, $C_{1-10}$ heteroalkynyl, or $C_{3-10}$ heterocyclyl. In some forms, each M can be an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, M can be —$(CH_2)_p$—, where p is an integer from 1 to 6. In some forms, X can be —$(CH_2)_p$—, where p is an integer from 2 to 5. In some forms, X can be —$(CH_2)_p$—, where p is 3 or 4. In some forms, X can be —$(CH_2)_p$—, where p is 4; and where Q can be —$CH_2$—, C=NH, C(O), S(O), or S(O)$_2$. In some forms, Z can be C(O) or C=NH. In some forms, Q can be —$(CH_2)_p$—, where p is an integer from 1 to 6. In some forms, Q can be —$(CH_2)_p$—, where p is an integer from 2 to 5. In some forms, Q can be —$(CH_2)_p$—, where p is 3 or 4. The compounds described herein can be formulated with, for example, a pharmaceutically acceptable carrier and, optionally one or more pharmaceutically acceptable excipients, for administration to a patient in need thereof.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figure 1:
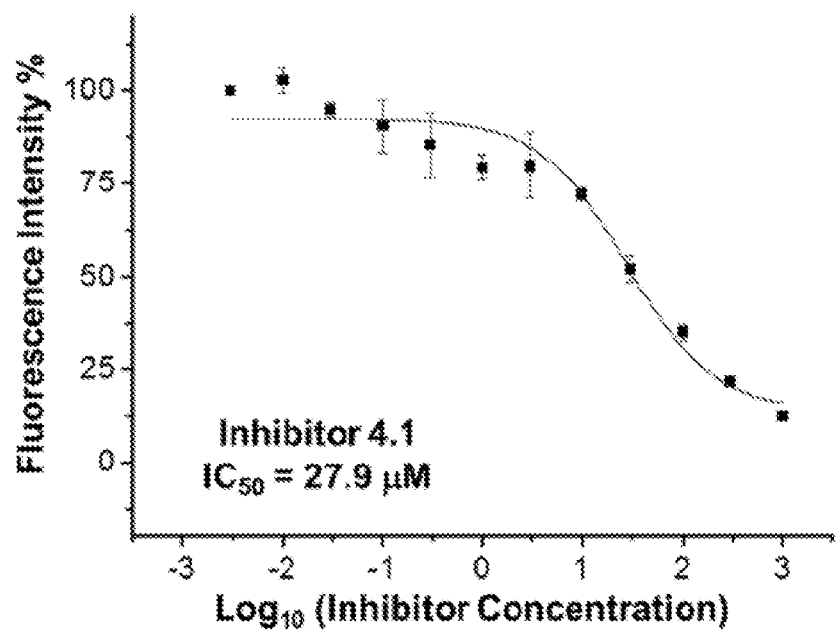
FIG. 1 is a graph showing the effects of compound 1 inhibitor concentration on the actual fluorescence intensity of probe-labeled protein, leading to determination of $IC_{50}$.
Figure 2:
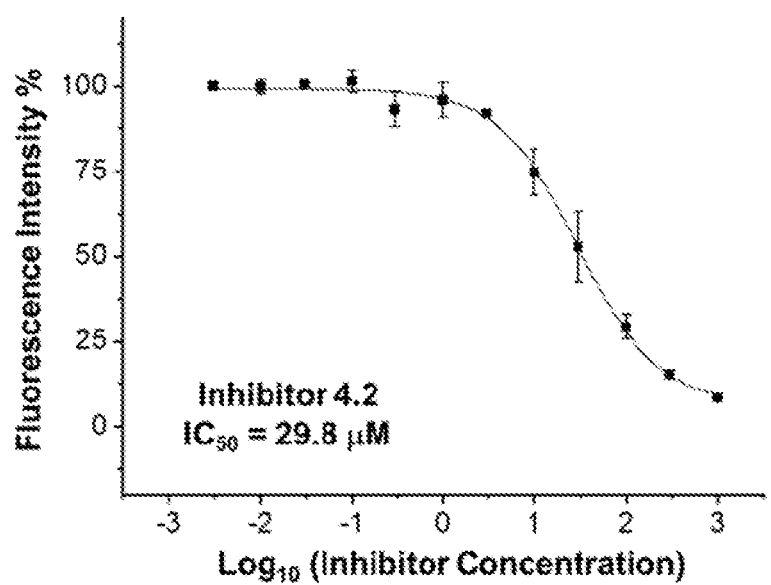
FIG. 2 is a graph showing the effects of compound 2 inhibitor concentration on the actual fluorescence intensity of probe-labeled protein, leading to determination of $IC_{50}$.
Figure 3:
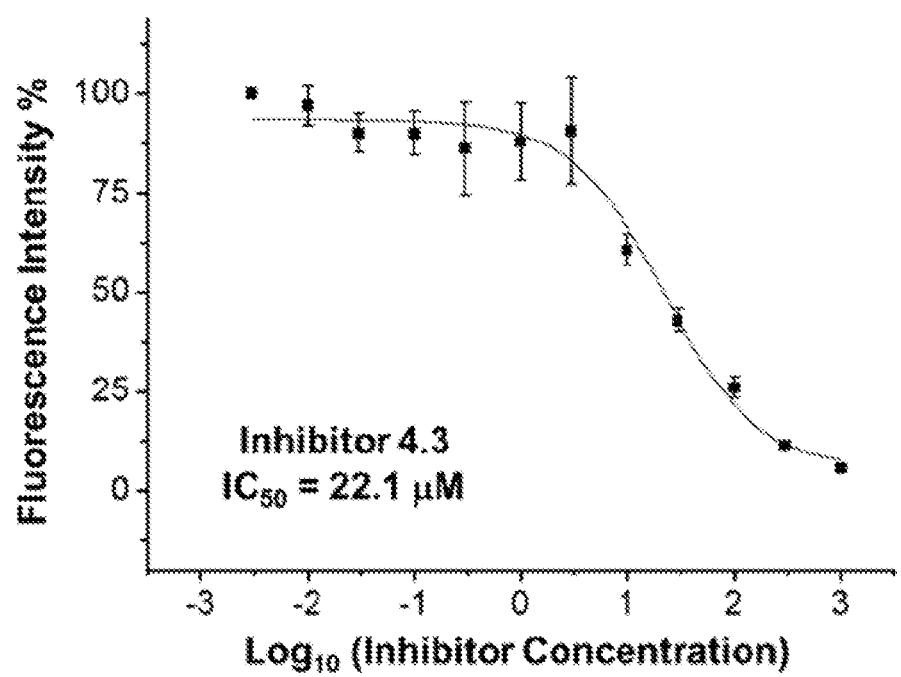
FIG. 3 is a graph showing the effects of compound 3 inhibitor concentration on the actual fluorescence intensity of probe-labeled protein, leading to determination of $IC_{50}$.
Figure 4:
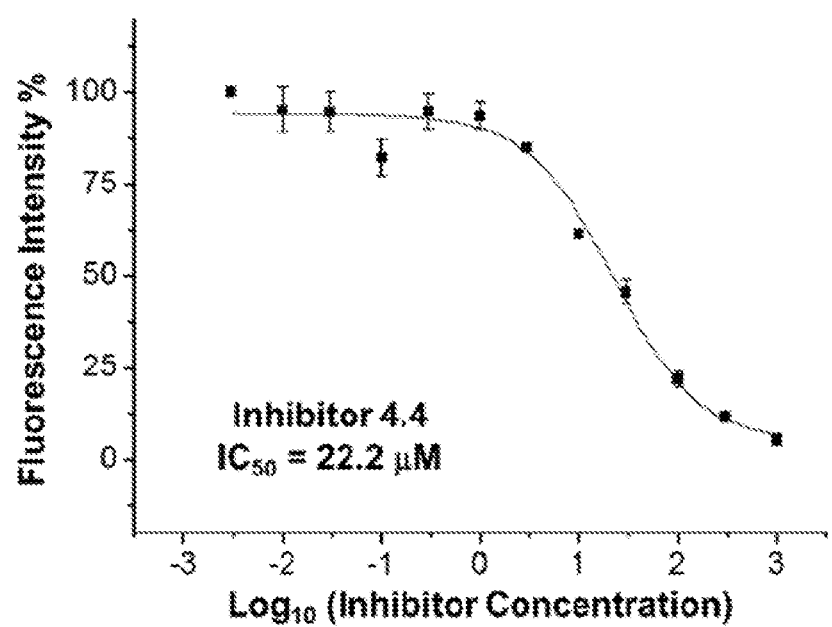
FIG. 4 is a graph showing the effects of compound 4 inhibitor concentration on the actual fluorescence intensity of probe-labeled protein, leading to determination of $IC_{50}$.
Figure 5:
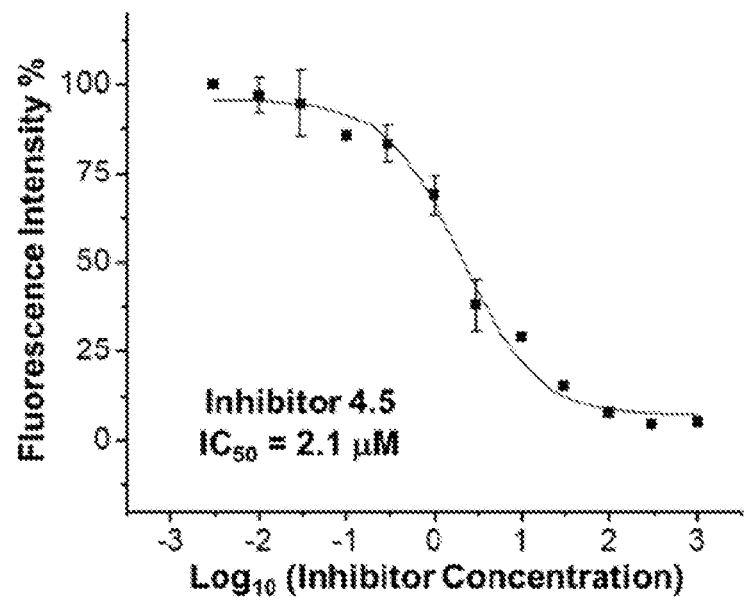
FIG. 5 is a graph showing the effects of compound 5 inhibitor concentration on the actual fluorescence intensity of probe-labeled protein, leading to determination of $IC_{50}$.
Figure 6:
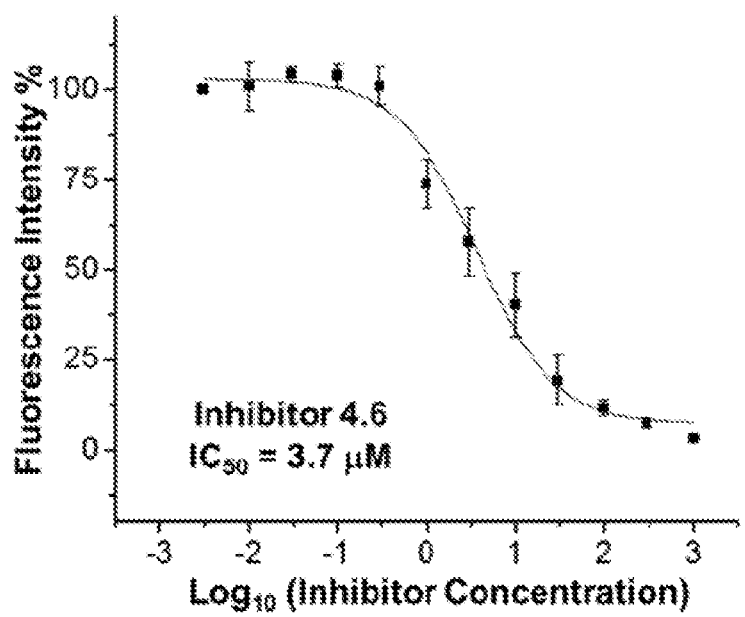
FIG. 6 is a graph showing the effects of compound 6 inhibitor concentration on the actual fluorescence intensity of probe-labeled protein, leading to determination of $IC_{50}$.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

I. Definitions

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "alkenyl group" as used herein is a hydrocarbon group of from 2 to 24 carbon atoms and structural formula containing at least one carbon-carbon double bond. Asymmetric structures such as (AB)C=C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to 24 carbon atoms and a structural formula containing at least one carbon-carbon triple bond.

The term "aryl group" as used herein is any carbon-based aromatic group including, but not limited to, benzene, naphthalene, etc. The term "aromatic" also includes "heteroaryl group," or "heterocyclic aromatic group," which is defined as an aromatic group that has at least one heteroatom incorporated within the ring of the aromatic group, and the "heteroaryl group" or "heterocyclic aromatic group" has 5 to 9 ring atoms ("$C_{5-9}$ heterocyclic aromatic group"), such as 5 or 6 ring atoms ("$C_5$ or $C_6$ heterocyclic aromatic group"), selected from carbon atoms and heteroatoms. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "circular oligomer" as used herein is an oligomer whose ends, two side chains thereof, or a combination thereof, are covalently coupled so that it forms a circular structure.

By the term "effective amount" of a compound as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "inhibit" means to reduce or decrease in activity or expression. This can be a complete inhibition of activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

The term "thioester" as used herein refers to a functional group characterized by a sulfur atom flanked by one carbonyl group and one carbon of any hybridization.

The term "sulfonate" as used herein refers to a salt or ester of a sulfonic acid.

As used herein, the term "peptide" refers to a class of compounds composed of amino acids chemically bound together. In general, the amino acids are chemically bound together via amide linkages (CONH); however, the amino acids may be bound together by other chemical bonds known in the art. For example, the amino acids may be bound by amine linkages. Peptide as used herein includes oligomers of amino acids and small and large peptides, including polypeptides.

As used herein, the terms "π-π-π stacking", "π-π stacking", or "π-stacking", or "pi-stacking" are used interchangeably and refer to attractive non-covalent interactions between aromatic rings which contain π-bonds.

As used herein, the terms "conjugated" and "delocalized" refer to delocalized π-electrons (which may also be referred to as conjugated π electrons). Conjugated π-electrons or a conjugated system refers to a system of overlapping p-orbitals (bridging intervening sigma bonds) with delocalized electrons which are present in compounds having alternating single and multiple bonds, most often double bonds.

As used herein, the term "pharmacological activity" refers to the inherent physical properties of a peptide or polypeptide. These properties include but are not limited to half-life, solubility, and stability and other pharmacokinetic properties.

By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

As used herein, a "ring" refers to a cycle of atoms and bonds in a molecule or to a connected set of atoms and bonds in which every atom and bond is a member of a cycle. A "monocyclic" ring typically consists of one cyclic structure; a "bicyclic" ring has two cyclic structures; a "tricyclic" ring has three cyclic structures; a "tetracyclic" ring has four cyclic structures; and so on.

As used herein, the term "selectively targets" refers to the ability to specifically home in on one specific area.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

The term "treatment" and "treating" as used herein is meant as the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

Numerical ranges disclosed in the present application of any type, disclose individually each possible number that such a range could reasonably encompass, as well as any sub-ranges and combinations of sub-ranges encompassed therein. A carbon range (i.e., $C_1$-$C_{10}$), is intended to disclose individually every possible carbon value and/or sub-range encompassed within. For example, a carbon length range of $C_1$-$C_{10}$ discloses $C_1$, $C_2$, $C_3$, $C_4$, $C_5$, $C_6$, $C_7$, $C_8$, $C_9$, and $C_{10}$, as well as discloses sub-ranges encompassed therein, such as $C_2$-$C_9$, $C_3$-$C_8$, $C_1$-$C_5$, etc.

II. Compounds

Provided herein are compounds including a base peptide and a side chain, and pharmaceutically acceptable forms thereof. The term "side chain" as used herein refers to a group of atoms attached to the main part of the molecule, or the base peptide. In the most preferred embodiments, the compounds are linear peptides. In some forms, the compounds are cyclic peptides. Pharmaceutical compositions including the linear peptides or cyclic peptides are proteins including the compound and a pharmaceutically acceptable excipient. Such pharmaceutical compositions may optionally contain one or more additional biologically active substances. For the purposes of the present disclosure, the phrase "active ingredient" generally refers to a linear or cyclic compound.

The relative amounts of the active ingredient, the pharmaceutically acceptable excipient, and/or any additional ingredients in a pharmaceutical composition will vary, depending upon the identity, size, and/or condition of the subject treated and further depending upon the route by which the composition is to be administered. By way of example, the composition may contain between 0.1% and 100% (w/w) active ingredient.

The delivery can be targeted to cells or tissues of interest, such as tumors. In some forms, delivery is targeted to π-π-π-stacked molecules in the YEATS domain of proteins. Internalization of compositions (including nanoparticles, drugs, detectable markers, and other compounds) and their payload into target cells and penetration into target tissue can increase the efficiency of the targeting and the effectiveness of the payload.

A. Oligomer Backbone

The synthesis of a peptide first involves the selection of a desired sequence and number of amino acids and amino acid analogues. As one of ordinary skill in the art will realize, the number, stereochemistry, and type of amino acid structures (natural or non-natural) selected will depend upon the size of the peptide to be prepared, the ability of the particular amino acids to generate a desired structural motif (e.g., an α-helix), and any particular motifs that are desirable to mimic protein domains that effectively bind to the target or effector biomolecule. In some forms, the peptides are helical. In some forms, the peptides are non-helical. Thus the peptide sequence can parallel a sequence or subsequence of a known peptide or protein and improve the stability or other characteristics of an existing α-helix or other amino acid motif(s) therein. Additionally or alternatively, the peptide sequence can be added to a known peptide or protein to add an α-helix or other amino acid motif(s) wherein none existed before.

In preferred forms, the peptide backbone includes a linear motif. Different amino acids have different propensities for forming different secondary structures. For example, methionine (M, Met), alanine (A, Ala), leucine (L, Leu), glutamate (E, Glu), and lysine (K, Lys) all have especially high α-helix forming propensities. Thus in some forms, the peptide sequence includes or consists of methionine (M, Met), alanine (A, Ala), leucine (L, Leu), glutamate (E, Glu), and lysine (K, Lys). In contrast, proline (P, Pro) and glycine (G, Gly) are α-helix disruptors. Thus in some forms, the peptide sequence does not include methionine (M, Met), alanine (A, Ala), leucine (L, Leu), glutamate (E, Glu), and lysine (K, Lys).

In particular exemplary forms, the peptide backbone includes or consists of

```
                                              (SEQ ID NO: 1)
H2N-Lys-Gln-Thr-Ala-Arg-Lys-Ser-Thr-Gly-Gly-CONH2;

(SEQ ID NO: 2)
H2N-Gln-Thr-Ala-Arg-Lys-CONH2;

(SEQ ID NO: 3)
H2N-Lys-Gln-Thr-Ala-Arg-Lys-CONH2;
or (SEQ ID NO: 4)
CbzHN-Gln-Thr-Ala-Arg-Lys-CONH2.
```

Cbz refers to carboxybenzyl.

It is to be understood, however, that the peptide backbone structure is not limited to above identified sequences, and, as such, may vary.

It is understood that there are numerous amino acid analogs which can be incorporated into the disclosed peptides. For example, there are numerous D amino acids or other non-natural amino acids which can be used. The opposite stereoisomers of naturally occurring peptides are disclosed, as well as the stereo isomers of peptide analogs. These amino acids can readily be incorporated into polypeptide chains by chemical synthesis or by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10): 400-403 (1989); Benner, TIB Tech, 12:158-163 (1994); Ibba and Hennecke, Bio/technology, 12:678-682 (1994) all of which are herein incorporated by reference at least for material related to amino acid analogs).

B. Active Agents

Disclosed are compositions and methods for treating a subject having acute leukemia. Generally, the compositions include linear or circular oligomers that include a base oligomer and a side chain. The side chain is generally designed or selected to include a conjugated/delocalized group. The oligomers generally can interact with a YEATS protein domain via the conjugated/delocalized group. It is believed that this interaction interferes with or inhibits π-π-π stacking interactions in the YEATS protein domain and that this has the desired YEATS inhibitory effect. The YEATS domains specifically recognize the lysine crotonylation marks on histones, accommodating the crotonyl group by forming π-π-π stacking using two conserved aromatic ring-containing amino acid residues.

In preferred forms, the base oligomer is a peptide or peptide analog. Generally, the oligomer can be made up of bivalent linking units where the linking units are joined together via an appropriate linkage. Bivalent linking units a compounds, units, monomers, etc. that have two moieties or groups that allow linkage to other compounds, units, monomers, etc. This allows oligomers of the bivalent linking units to be formed or constituted. Generally, the disclosed bivalent linking units include one or more side chains in addition to the backbone or link between the moieties or groups that allow linkage to other bivalent linking units. Alpha amino acids are a preferred example of bivalent lining units.

The linkages of bivalent linkage units can be, for example, amide, ester, thioester, thioamide, imidate, imide, sulfonate, or sulfonamide linkages. Different linkages in the oligomer can be the same or different, and can be made up of any combination of linkages. Preferred linkages are amide linkages. The linking units can be linked head-to-tail, head-to-head, tail-to-tail. Different linking units in the oligomer can be linked in the same orientation or in different orientations in any order. Preferred linking orientation is head-to-tail orientation. Different linking units in the oligomer can the same or different, and can be made up of any combination of linking units. Preferred linking units are α-amino acids.

In some forms, the composition includes a compound, or a pharmaceutically acceptable salt thereof, that comprises a base oligomer and a side chain. In some forms, the compound can be defined according to Formula (I):

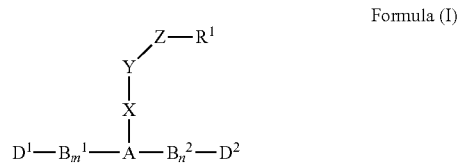

Formula (I)

where A can be $CR^2$ or N; where each instance of $B^1$ and $B^2$ can be an independently selected bivalent linking unit, where the linking units can be connected by amide, ester, thioester, thioamide, imidate, imide, sulfonate, or sulfonamide linkage; where the linking units can be linked in a head-to-tail manner; where $D^1$ can be H or unsubstituted or substituted hydrocarbyl, carbocyclyl or heterocyclyl; where $D^2$ can be H, $NH_2$, $NHR^{15}$, $NR^{16}R^{17}$, OH, $OR^{18}$, or unsubstituted or substituted hydrocarbyl, carbocyclyl or heterocyclyl; where X can be unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl; where Y can be $NR^3$, O, or S; where Z can be —CO—, —CS—, —$CNR^4$—, —SO—, or —$SO_2$—; where $R^{15}$, $R^{16}$, $R^{17}$, and $R^{18}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; where $R^2$, $R^3$, and $R^4$ can be independently H or $C_{1-10}$ hydrocarbyl, $C_{1-10}$ carbocyclyl, or $C_{1-10}$ heterocyclyl; where $R^1$ can be a conjugated/delocalized group. In some forms, the conjugated/delocalized group can be an unsubstituted or substituted, heterocyclic or carbocyclic, aromatic ring (such as monocyclic, bicyclic, tricyclic, tetracyclic) or unsubstituted or substituted alkenyl or alkynyl, wherein the conjugated/delocalized group includes overlapping p-orbitals which allow for pi-electrons to become delocalized; and where m and n are each independently integers from 0 to 10, where at least one of m or n is not 0. In some forms, at least one of m or n is not 0. In some forms, both of m or n are 0.

In some forms, A can be $CR^2$ or N. In some forms, $R^2$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, A can be $CR^2$ and $R^2$ can be H.

In some forms, $B^1$ can be —NH—, —O—, —S—, or —$(CH_2)_p$—, where p is an integer from 1 to 6, for example 1, 2, 3, 4, 5, and 6. In some forms, the terminal $B^2$ can be —C(═O)—, —C(═NH)—, —C(═S)—, —S(═O)$_2$—, or -(representing a terminal bond on $B^2$). In some forms, $D^2$ can be H, $NH_2$, $NHR^{15}$, $NR^{16}R^{17}$, OH, $OR^{18}$, or unsubstituted or substituted hydrocarbyl, carbocyclyl or heterocyclyl, where $R^{15}$, $R^{16}$, $R^{17}$, and $R^{18}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic.

In some forms, the bivalent unit can be

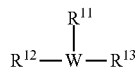

where W can be $CR^2$, $R^{11}$ can be a side chain, and $R^{12}$ and $R^{13}$ can be components of linkages such as amide linkages, ester linkages, thioester linkages, thioamine linkages, imidate linkages, imide linkages, sulfonate linkages, and sulfonamide linkages. Different bivalent units can be linked with the same or different types of linkages, with linked $R^{12}$ and $R^{13}$ groups being compatible components of the desired linkage. In some forms, $R^{12}$ can be —C(═O)—$R^{19}$, —C(═NH)—$R^{19}$, —C(═S)—$R^{19}$, or —S(═O)$_2$—$R^{19}$. In some forms, $R^{19}$ can be $N(R^{14})$—, O—, S—, or $N(R^{14})$—C(═O)—, where $R^{14}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic.

In some forms, $R^{11}$ can be made up in part of an existing or normal side chain of a monomer of the oligomer. Thus, for example, in a composition where the linear base oligomer is a peptide, one of the side chains of an amino acid in the peptide can comprise part of $R^{11}$ or can be replaced by $R^{11}$. In general, a composition of this form includes at least one $R^{11}$ terminating in $R^1$ (with $R^1$ as defined herein). In some forms, composition of this form includes at least one $R^{11}$ defined according to the following structure:

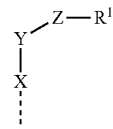

where the dashed line denotes the linkage point of the above structure and where $R^1$ can be a conjugated/delocalized group and X, Y, and Z are as defined herein.

In some forms, the bivalent units are all independently any α-amino acid. In some forms, the bivalent units are each an α-amino acid independently selected from the group consisting of Lys, Gln, Thr, Ala, Arg, Ser, and Gly.

In some forms, $D^1$ can be H or unsubstituted or substituted hydrocarbyl, carbocyclyl or heterocyclyl. In some forms, $D^1$ can be an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, $D^1$ can be H. In some forms, $D^1$ can be carboxybenzyl (Cbz). In some forms, $D^1$ can be acetyl. In some forms, $D^1$ can be benzenemethylcarbonyl. In some forms, $D^1$ can be benzeneethylcarbonyl. In some forms, $D^1$ can be benzenepropylcarbonyl. In some forms, $D^1$ can be naphthaleneethylcarbonyl.

In some forms, $D^2$ can be H, —$NH_2$, —$NHR^{15}$, —$NR^{16}R^{17}$, —OH, —$OR^{18}$, or unsubstituted or substituted hydrocarbyl, carbocyclyl or heterocyclyl, where $R^{15}$, $R^{16}$, $R^{17}$, and $R^{18}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic. In some forms, $D^2$ can be H or —$NH_2$. In some forms, $D^2$ can be an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, $D^2$ can be H. In some forms, $D^2$ can be —$NH_2$. In some forms, $D^2$ can be OH or $OR^{18}$. In some forms, $D^2$ can be OH.

In some forms, X can be unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl. In some forms, X can be an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, X can be —$(CH_2)_p$—, where p is an integer from 1 to 6. In some forms, X can be —$(CH_2)_p$—, where p is an integer from 2 to 5. In some forms, X can be —$(CH_2)_p$—, where p is 3 or 4. In some forms, X can be —$(CH_2)_p$—, where p is 4.

In some forms, Y can be —$NR^3$, —O—, or —S—. In some forms, $R^3$ can be H or $C_{1-10}$ hydrocarbyl, $C_{1-10}$ carbocyclyl, or $C_{1-10}$ heterocyclyl. In some forms, $R^3$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms Y can be $NR^3$, and $R^3$ can be H.

In some forms, Z can be —CO—, —CS—, —$CNR^4$—, —SO—, or —$SO_2$—. In some forms, Z can be —CO—. In some forms, $R^4$ can be H or $C_{1-10}$ hydrocarbyl, $C_{1-10}$ carbocyclyl, or $C_{1-10}$ heterocyclyl. In some forms, $R^4$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group.

In some forms, the conjugated/delocalized group can be an unsubstituted or substituted, heterocyclic or carbocyclic, aromatic ring or unsubstituted or substituted alkenyl or alkynyl, wherein the conjugated/delocalized group includes p-orbitals which allow for pi-electrons to become delocalized. In some forms, the conjugated/delocalized group can be unsubstituted or substituted aromatic rings. In some forms, the conjugated/delocalized group can be unsubstituted or substituted aromatic monocyclic, bicyclic, tricyclic, or tetracyclic rings. In some forms, the conjugated/delocalized group can be unsubstituted or substituted alkenyl or alkynyl.

In some forms, $R^1$ can be an unsubstituted or substituted, heterocyclic or carbocyclic, aromatic ring or unsubstituted or substituted alkenyl or alkynyl, wherein the conjugated/delocalized group includes p-orbitals which allow for pi-electrons to become delocalized. In some forms, $R^1$ can be unsubstituted or substituted aromatic rings. In some forms, $R^1$ can be unsubstituted or substituted aromatic monocyclic, bicyclic, tricyclic, or tetracyclic rings. In some forms, $R^1$ can be unsubstituted or substituted alkenyl or alkynyl. In some forms, $R^1$ can be:

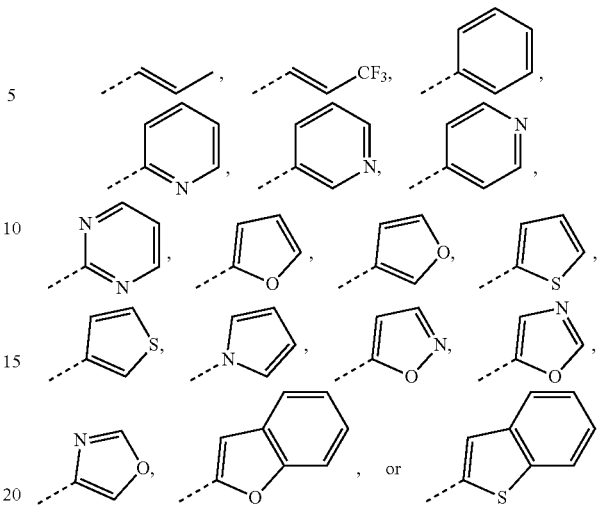

where the dashed lines denote the linkage point of the above groups.

In some forms, $R^1$ can be unsubstituted $C_6$ carbocyclic aromatic ring. In some forms, $R^1$ can be unsubstituted $C_6$ heterocyclic aromatic ring. In some forms, the unsubstituted $C_6$ heterocyclic aromatic ring can have nitrogen at any one of positions 2, 3, 4, 5, or 6. In some forms, the unsubstituted $C_6$ heterocyclic aromatic ring can have nitrogen at position 2. In some forms, the unsubstituted $C_6$ heterocyclic aromatic ring can have nitrogen at position 3. In some forms, the unsubstituted $C_6$ heterocyclic aromatic ring can have nitrogen at position 4. In some forms, the unsubstituted $C_6$ heterocyclic aromatic ring can have nitrogen at position 5. In some forms, the unsubstituted $C_6$ heterocyclic aromatic ring can have nitrogen at position 6.

In some forms, the unsubstituted $C_6$ heterocyclic aromatic ring can have nitrogen at any two of positions 2, 3, 4, 5, or 6. In some forms, the unsubstituted $C_6$ heterocyclic aromatic ring can have nitrogen at positions 2 and 3. In some forms, the unsubstituted $C_6$ heterocyclic aromatic ring can have nitrogen at positions 2 and 4. In some forms, the unsubstituted $C_6$ heterocyclic aromatic ring can have nitrogen at positions 2 and 5. In some forms, the unsubstituted $C_6$ heterocyclic aromatic ring can have nitrogen at positions 2 and 6. In some forms, the unsubstituted $C_6$ heterocyclic aromatic ring can have nitrogen at positions 3 and 4. In some forms, the unsubstituted $C_6$ heterocyclic aromatic ring can have nitrogen at positions 3 and 5. In some forms, the unsubstituted $C_6$ heterocyclic aromatic ring can have nitrogen at positions 3 and 6. In some forms, the unsubstituted $C_6$ heterocyclic aromatic ring can have nitrogen at positions 4 and 5. In some forms, the unsubstituted $C_6$ heterocyclic aromatic ring can have nitrogen at positions 4 and 6. In some forms, the unsubstituted $C_6$ heterocyclic aromatic ring can have nitrogen at positions 5 and 6.

In some forms, $R^1$ can be unsubstituted $C_5$ carbocyclic aromatic ring. In some forms, $R^1$ can be unsubstituted $C_5$ heterocyclic aromatic ring. In some forms, the unsubstituted $C_5$ heterocyclic aromatic ring can have nitrogen at any one of positions 2, 3, 4, 5, or 1. In some forms, the unsubstituted $C_5$ heterocyclic aromatic ring can have nitrogen at position 2. In some forms, the unsubstituted $C_5$ heterocyclic aromatic ring can have nitrogen at position 3. In some forms, the unsubstituted $C_5$ heterocyclic aromatic ring can have nitrogen at position 4. In some forms, the unsubstituted $C_5$ heterocyclic aromatic ring can have nitrogen at position 5. In some forms, the unsubstituted $C_5$ heterocyclic aromatic ring can have nitrogen at position 1.

In some forms, the unsubstituted $C_5$ heterocyclic aromatic ring can have nitrogen at any two of positions 2, 3, 4, 5, or 1. In some forms, the unsubstituted $C_5$ heterocyclic aromatic ring can have nitrogen at positions 2 and 3. In some forms, the unsubstituted $C_5$ heterocyclic aromatic ring can have nitrogen at positions 2 and 4. In some forms, the unsubstituted $C_5$ heterocyclic aromatic ring can have nitrogen at positions 2 and 5. In some forms, the unsubstituted $C_5$ heterocyclic aromatic ring can have nitrogen at positions 2 and 1. In some forms, the unsubstituted $C_5$ heterocyclic aromatic ring can have nitrogen at positions 3 and 4. In some forms, the unsubstituted $C_5$ heterocyclic aromatic ring can have nitrogen at positions 3 and 5. In some forms, the unsubstituted $C_5$ heterocyclic aromatic ring can have nitrogen at positions 3 and 1. In some forms, the unsubstituted $C_5$ heterocyclic aromatic ring can have nitrogen at positions 4 and 5. In some forms, the unsubstituted $C_5$ heterocyclic aromatic ring can have nitrogen at positions 4 and 1. In some forms, the unsubstituted $C_5$ heterocyclic aromatic ring can have nitrogen at positions 5 and 1.

In some forms, the unsubstituted $C_5$ heterocyclic aromatic ring can have oxygen at any one of positions 2, 3, 4, 5, or 1. In some forms, the unsubstituted $C_5$ heterocyclic aromatic ring can have oxygen at position 2. In some forms, the unsubstituted $C_5$ heterocyclic aromatic ring can have oxygen at position 3. In some forms, the unsubstituted $C_5$ heterocyclic aromatic ring can have oxygen at position 4. In some forms, the unsubstituted $C_5$ heterocyclic aromatic ring can have oxygen at position 5. In some forms, the unsubstituted $C_5$ heterocyclic aromatic ring can have oxygen at position 1.

In some forms, the unsubstituted $C_5$ heterocyclic aromatic ring can have sulfur at any one of positions 2, 3, 4, 5, or 1. In some forms, the unsubstituted $C_5$ heterocyclic aromatic ring can have sulfur at position 2. In some forms, the unsubstituted $C_5$ heterocyclic aromatic ring can have sulfur at position 3. In some forms, the unsubstituted $C_5$ heterocyclic aromatic ring can have sulfur at position 4. In some forms, the unsubstituted $C_5$ heterocyclic aromatic ring can have sulfur at position 5. In some forms, the unsubstituted $C_5$ heterocyclic aromatic ring can have sulfur at position 1.

In some forms, the unsubstituted $C_5$ heterocyclic aromatic ring can have nitrogen or oxygen at any one of positions 2, 3, 4, 5, or 1. In some forms, the unsubstituted $C_5$ heterocyclic aromatic ring can have nitrogen or oxygen at position 2. In some forms, the unsubstituted $C_5$ heterocyclic aromatic ring can have nitrogen or oxygen at position 3. In some forms, the unsubstituted $C_5$ heterocyclic aromatic ring can have nitrogen or oxygen at position 4. In some forms, the unsubstituted $C_5$ heterocyclic aromatic ring can have nitrogen or oxygen at position 5. In some forms, the unsubstituted $C_5$ heterocyclic aromatic ring can have nitrogen or oxygen at position 1.

In some forms, the unsubstituted $C_5$ heterocyclic aromatic ring can have nitrogen or oxygen independently at any two of positions 2, 3, 4, 5, or 1. In some forms, the unsubstituted $C_5$ heterocyclic aromatic ring can have nitrogen or oxygen independently at positions 2 and 3. In some forms, the unsubstituted $C_5$ heterocyclic aromatic ring can have nitrogen or oxygen independently at positions 2 and 4. In some forms, the unsubstituted $C_5$ heterocyclic aromatic ring can have nitrogen or oxygen independently at positions 2 and 5. In some forms, the unsubstituted $C_5$ heterocyclic aromatic ring can have nitrogen or oxygen independently at positions 2 and 1. In some forms, the unsubstituted $C_5$ heterocyclic aromatic ring can have nitrogen or oxygen independently at positions 3 and 4. In some forms, the unsubstituted $C_5$ heterocyclic aromatic ring can have nitrogen or oxygen independently at positions 3 and 5. In some forms, the unsubstituted $C_5$ heterocyclic aromatic ring can have nitrogen or oxygen independently at positions 3 and 1. In some forms, the unsubstituted $C_5$ heterocyclic aromatic ring can have nitrogen or oxygen independently at positions 4 and 5. In some forms, the unsubstituted $C_5$ heterocyclic aromatic ring can have nitrogen or oxygen independently at positions 4 and 1. In some forms, the unsubstituted $C_5$ heterocyclic aromatic ring can have nitrogen or oxygen independently at positions 5 and 1.

In some forms, the unsubstituted $C_5$ heterocyclic aromatic ring can have oxygen at any one of positions 2, 3, 4, 5, or 1 and nitrogen at any one of positions 2, 3, 4, or 1 not occupied by oxygen. In some forms, the unsubstituted $C_5$ heterocyclic aromatic ring can have oxygen at position 2 and nitrogen at position 3. In some forms, the unsubstituted $C_5$ heterocyclic aromatic ring can have oxygen at position 2 and nitrogen at position 4. In some forms, the unsubstituted $C_5$ heterocyclic aromatic ring can have oxygen at position 2 and nitrogen at position 5. In some forms, the unsubstituted $C_5$ heterocyclic aromatic ring can have oxygen at position 2 and nitrogen at position 1. In some forms, the unsubstituted $C_5$ heterocyclic aromatic ring can have oxygen at position 3 and nitrogen at position 4. In some forms, the unsubstituted $C_5$ heterocyclic aromatic ring can have oxygen at position 3 and nitrogen at position 5. In some forms, the unsubstituted $C_5$ heterocyclic aromatic ring can have oxygen at position 3 and nitrogen at position 1. In some forms, the unsubstituted $C_5$ heterocyclic aromatic ring can have oxygen at position 4 and nitrogen at position 5. In some forms, the unsubstituted $C_5$ heterocyclic aromatic ring can have oxygen at position 4 and nitrogen at position 1. In some forms, the unsubstituted $C_5$ heterocyclic aromatic ring can have oxygen at position 5 and nitrogen at position 1.

In some forms, the unsubstituted $C_5$ heterocyclic aromatic ring can have nitrogen at any one of positions 2, 3, 4, 5, or 1 and oxygen at any one of positions 2, 3, 4, or 1 not occupied by nitrogen. In some forms, the unsubstituted $C_5$ heterocyclic aromatic ring can have nitrogen at position 2 and oxygen at position 3. In some forms, the unsubstituted $C_5$ heterocyclic aromatic ring can have nitrogen at position 2 and oxygen at position 4. In some forms, the unsubstituted $C_5$ heterocyclic aromatic ring can have nitrogen at position 2 and oxygen at position 5. In some forms, the unsubstituted $C_5$ heterocyclic aromatic ring can have nitrogen at position 2 and oxygen at position 1. In some forms, the unsubstituted $C_5$ heterocyclic aromatic ring can have nitrogen at position 3 and oxygen at position 4. In some forms, the unsubstituted $C_5$ heterocyclic aromatic ring can have nitrogen at position 3 and oxygen at position 5. In some forms, the unsubstituted $C_5$ heterocyclic aromatic ring can have nitrogen at position 3 and oxygen at position 1. In some forms, the unsubstituted $C_5$ heterocyclic aromatic ring can have nitrogen at position 4 and oxygen at position 5. In some forms, the unsubstituted $C_5$ heterocyclic aromatic ring can have nitrogen at position 4 and oxygen at position 1. In some forms, the unsubstituted $C_5$ heterocyclic aromatic ring can have nitrogen at position 5 and oxygen at position 1.

In some forms, $R^1$ can be unsubstituted $C_9$ bicyclic carbocyclic aromatic ring. In some forms, $R^1$ can be unsubstituted $C_9$ bicyclic heterocyclic aromatic ring. In some forms, the unsubstituted $C_9$ bicyclic heterocyclic aromatic ring can have nitrogen at any one of positions 1, 2, 3, 4, 5, 6, 7, 8, or 9. In some forms, the unsubstituted $C_9$ bicyclic heterocyclic aromatic ring can have nitrogen at position 1. In some forms, the unsubstituted $C_9$ bicyclic heterocyclic aromatic ring can have nitrogen at position 2. In some forms, the unsubstituted $C_9$ bicyclic heterocyclic aromatic ring can have nitrogen at position 3. In some forms, the unsubstituted $C_9$ bicyclic heterocyclic aromatic ring can have nitrogen at position 4. In some forms, the unsubstituted $C_9$ bicyclic heterocyclic aromatic ring can have nitrogen at position 5. In some forms, the unsubstituted $C_9$ bicyclic heterocyclic aromatic ring can have nitrogen at position 6. In some forms, the unsubstituted $C_9$ bicyclic heterocyclic aromatic ring can have nitrogen at position 7. In some forms, the unsubstituted $C_9$ bicyclic heterocyclic aromatic ring can have nitrogen at position 8. In some forms, the unsubstituted $C_9$ bicyclic heterocyclic aromatic ring can have nitrogen at position 9.

In some forms, the unsubstituted $C_9$ bicyclic heterocyclic aromatic ring can have nitrogen at any two of positions 1, 2, 3, 4, 5, 6, 7, 8, or 9. In some forms, the unsubstituted $C_9$ bicyclic heterocyclic aromatic ring can have nitrogen at positions 1 and 3. In some forms, the unsubstituted $C_9$ bicyclic heterocyclic aromatic ring can have nitrogen at positions 1 and 4. In some forms, the unsubstituted $C_9$ bicyclic heterocyclic aromatic ring can have nitrogen at positions 1 and 5. In some forms, the unsubstituted $C_9$ bicyclic heterocyclic aromatic ring can have nitrogen at positions 1 and 6. In some forms, the unsubstituted $C_9$ bicyclic heterocyclic aromatic ring can have nitrogen at positions 1 and 7. In some forms, the unsubstituted $C_9$ bicyclic heterocyclic aromatic ring can have nitrogen at positions 1 and 8. In some forms, the unsubstituted $C_9$ bicyclic heterocyclic aromatic ring can have nitrogen at positions 1 and 9.

In some forms, the unsubstituted $C_9$ bicyclic heterocyclic aromatic ring can have nitrogen at positions 2 and 3. In some forms, the unsubstituted $C_9$ bicyclic heterocyclic aromatic ring can have nitrogen at positions 2 and 4. In some forms, the unsubstituted $C_9$ bicyclic heterocyclic aromatic ring can have nitrogen at positions 2 and 5. In some forms, the unsubstituted $C_9$ bicyclic heterocyclic aromatic ring can have nitrogen at positions 2 and 6. In some forms, the unsubstituted $C_9$ bicyclic heterocyclic aromatic ring can have nitrogen at positions 2 and 7. In some forms, the unsubstituted $C_9$ bicyclic heterocyclic aromatic ring can have nitrogen at positions 2 and 8. In some forms, the unsubstituted $C_9$ bicyclic heterocyclic aromatic ring can have nitrogen at positions 2 and 9.

In some forms, the unsubstituted $C_9$ bicyclic heterocyclic aromatic ring can have nitrogen at positions 3 and 4. In some forms, the unsubstituted $C_9$ bicyclic heterocyclic aromatic ring can have nitrogen at positions 3 and 5. In some forms, the unsubstituted $C_9$ bicyclic heterocyclic aromatic ring can have nitrogen at positions 3 and 6. In some forms, the unsubstituted $C_9$ bicyclic heterocyclic aromatic ring can have nitrogen at positions 3 and 7. In some forms, the unsubstituted $C_9$ bicyclic heterocyclic aromatic ring can have nitrogen at positions 3 and 8. In some forms, the unsubstituted $C_9$ bicyclic heterocyclic aromatic ring can have nitrogen at positions 3 and 9.

In some forms, the unsubstituted $C_9$ bicyclic heterocyclic aromatic ring can have nitrogen at positions 4 and 5. In some forms, the unsubstituted $C_9$ bicyclic heterocyclic aromatic ring can have nitrogen at positions 4 and 6. In some forms, the unsubstituted $C_9$ bicyclic heterocyclic aromatic ring can have nitrogen at positions 4 and 7. In some forms, the unsubstituted $C_9$ bicyclic heterocyclic aromatic ring can have nitrogen at positions 4 and 8. In some forms, the unsubstituted $C_9$ bicyclic heterocyclic aromatic ring can have nitrogen at positions 4 and 9.

In some forms, the unsubstituted $C_9$ bicyclic heterocyclic aromatic ring can have nitrogen at positions 5 and 6. In some forms, the unsubstituted $C_9$ bicyclic heterocyclic aromatic ring can have nitrogen at positions 5 and 7. In some forms, the unsubstituted $C_9$ bicyclic heterocyclic aromatic ring can have nitrogen at positions 5 and 8. In some forms, the unsubstituted $C_9$ bicyclic heterocyclic aromatic ring can have nitrogen at positions 5 and 9. In some forms, the unsubstituted $C_9$ bicyclic heterocyclic aromatic ring can have nitrogen at positions 6 and 7. In some forms, the unsubstituted $C_9$ bicyclic heterocyclic aromatic ring can have nitrogen at positions 6 and 8. In some forms, the unsubstituted $C_9$ bicyclic heterocyclic aromatic ring can have nitrogen at positions 6 and 9.

In some forms, the unsubstituted $C_9$ bicyclic heterocyclic aromatic ring can have nitrogen at positions 7 and 8. In some forms, the unsubstituted $C_9$ bicyclic heterocyclic aromatic ring can have nitrogen at positions 7 and 9. In some forms, the unsubstituted $C_9$ bicyclic heterocyclic aromatic ring can have nitrogen at positions 8 and 9.

In some forms, the unsubstituted $C_9$ bicyclic heterocyclic aromatic ring can have oxygen at any one of positions 2, 3, 4, 5, 7, 8, or 9. In some forms, the unsubstituted $C_9$ bicyclic heterocyclic aromatic ring can have oxygen at position 2. In some forms, the unsubstituted $C_9$ bicyclic heterocyclic aromatic ring can have oxygen at position 3. In some forms, the unsubstituted $C_9$ bicyclic heterocyclic aromatic ring can have oxygen at position 4. In some forms, the unsubstituted $C_9$ bicyclic heterocyclic aromatic ring can have oxygen at position 5. In some forms, the unsubstituted $C_9$ bicyclic heterocyclic aromatic ring can have oxygen at position 7. In some forms, the unsubstituted $C_9$ bicyclic heterocyclic aromatic ring can have oxygen at position 8. In some forms, the unsubstituted $C_9$ bicyclic heterocyclic aromatic ring can have oxygen at position 9.

In some forms, the unsubstituted $C_9$ bicyclic heterocyclic aromatic ring can have sulfur at any one of positions 2, 3, 4, 5, 7, 8, or 9. In some forms, the unsubstituted $C_9$ bicyclic heterocyclic aromatic ring can have sulfur at position 2. In some forms, the unsubstituted $C_9$ bicyclic heterocyclic aromatic ring can have sulfur at position 3. In some forms, the unsubstituted $C_9$ bicyclic heterocyclic aromatic ring can have sulfur at position 4. In some forms, the unsubstituted $C_9$ bicyclic heterocyclic aromatic ring can have sulfur at position 5. In some forms, the unsubstituted $C_9$ bicyclic heterocyclic aromatic ring can have sulfur at position 7. In some forms, the unsubstituted $C_9$ bicyclic heterocyclic aromatic ring can have sulfur at position 8. In some forms, the unsubstituted $C_9$ bicyclic heterocyclic aromatic ring can have sulfur at position 9.

In some forms, the unsubstituted $C_9$ bicyclic heterocyclic aromatic ring can have nitrogen at any one of positions 1, 2, 3, 4, 5, 6, 7, 8, or 9 or oxygen at any one of positions 2, 3, 4, 5, 7, 8, or 9. In some forms, the unsubstituted $C_9$ bicyclic heterocyclic aromatic ring can have nitrogen or oxygen at position 1. In some forms, the unsubstituted $C_9$ bicyclic heterocyclic aromatic ring can have nitrogen or oxygen at position 2. In some forms, the unsubstituted $C_9$ bicyclic heterocyclic aromatic ring can have nitrogen or oxygen at position 3. In some forms, the unsubstituted $C_9$ bicyclic heterocyclic aromatic ring can have nitrogen or oxygen at position 4. In some forms, the unsubstituted $C_9$ bicyclic heterocyclic aromatic ring can have nitrogen or oxygen at position 5. In some forms, the unsubstituted $C_9$ bicyclic heterocyclic aromatic ring can have nitrogen at position 6. In some forms, the unsubstituted $C_9$ bicyclic heterocyclic aromatic ring can have nitrogen or oxygen at position 7. In some forms, the unsubstituted $C_9$ bicyclic heterocyclic aromatic ring can have nitrogen or oxygen at position 8. In some forms, the unsubstituted $C_9$ bicyclic heterocyclic aromatic ring can have nitrogen or oxygen at position 9.

In some forms, the unsubstituted $C_9$ bicyclic heterocyclic aromatic ring can have nitrogen or oxygen independently at any two of positions 1, 2, 3, 4, 5, 6, 7, 8, or 9. In some forms, the unsubstituted $C_9$ bicyclic heterocyclic aromatic ring can have nitrogen at position 1 and nitrogen or oxygen at position 2. In some forms, the unsubstituted $C_9$ bicyclic heterocyclic aromatic ring can have nitrogen at position 1 and nitrogen or oxygen at position 3. In some forms, the unsubstituted $C_9$ bicyclic heterocyclic aromatic ring can have nitrogen at position 1 and nitrogen or oxygen at position 4. In some forms, the unsubstituted $C_9$ bicyclic heterocyclic aromatic ring can have nitrogen at position 1 and nitrogen or oxygen at position 5. In some forms, the unsubstituted $C_9$ bicyclic heterocyclic aromatic ring can have nitrogen at position 1 and nitrogen at position 6. In some forms, the unsubstituted $C_9$ bicyclic heterocyclic aromatic ring can have nitrogen at position 1 and nitrogen or oxygen at position 7. In some forms, the unsubstituted $C_9$ bicyclic heterocyclic aromatic ring can have nitrogen at position 1 and nitrogen or oxygen at position 8. In some forms, the unsubstituted $C_9$ bicyclic heterocyclic aromatic ring can have nitrogen at position 1 and nitrogen or oxygen at position 9.

In some forms, the unsubstituted $C_9$ bicyclic heterocyclic aromatic ring can have nitrogen or oxygen independently at positions 2 and 3. In some forms, the unsubstituted $C_9$ bicyclic heterocyclic aromatic ring can have nitrogen or oxygen independently at positions 2 and 4. In some forms, the unsubstituted $C_9$ bicyclic heterocyclic aromatic ring can have nitrogen or oxygen independently at positions 2 and 5. In some forms, the unsubstituted $C_9$ bicyclic heterocyclic aromatic ring can have nitrogen or oxygen at position 2 and nitrogen at position 6. In some forms, the unsubstituted $C_9$ bicyclic heterocyclic aromatic ring can have nitrogen or oxygen independently at positions 2 and 7. In some forms, the unsubstituted $C_9$ bicyclic heterocyclic aromatic ring can have nitrogen or oxygen independently at positions 2 and 8. In some forms, the unsubstituted $C_9$ bicyclic heterocyclic aromatic ring can have nitrogen or oxygen independently at positions 2 and 9.

In some forms, the unsubstituted $C_9$ bicyclic heterocyclic aromatic ring can have nitrogen or oxygen independently at positions 3 and 4. In some forms, the unsubstituted $C_9$ bicyclic heterocyclic aromatic ring can have nitrogen or oxygen independently at positions 3 and 5. In some forms, the unsubstituted $C_9$ bicyclic heterocyclic aromatic ring can have nitrogen or oxygen at position 3 and nitrogen at position 6. In some forms, the unsubstituted $C_9$ bicyclic heterocyclic aromatic ring can have nitrogen or oxygen independently at positions 3 and 7. In some forms, the unsubstituted $C_9$ bicyclic heterocyclic aromatic ring can have nitrogen or oxygen independently at positions 3 and 8. In some forms, the unsubstituted $C_9$ bicyclic heterocyclic aromatic ring can have nitrogen or oxygen independently at positions 3 and 9.

In some forms, the unsubstituted $C_9$ bicyclic heterocyclic aromatic ring can have nitrogen or oxygen independently at positions 4 and 5. In some forms, the unsubstituted $C_9$ bicyclic heterocyclic aromatic ring can have nitrogen or oxygen at position 4 and nitrogen at position 6. In some forms, the unsubstituted $C_9$ bicyclic heterocyclic aromatic ring can have nitrogen or oxygen independently at positions 4 and 7. In some forms, the unsubstituted $C_9$ bicyclic heterocyclic aromatic ring can have nitrogen or oxygen independently at positions 4 and 8. In some forms, the unsubstituted $C_9$ bicyclic heterocyclic aromatic ring can have nitrogen or oxygen independently at positions 4 and 9.

In some forms, the unsubstituted $C_9$ bicyclic heterocyclic aromatic ring can have nitrogen or oxygen at position 5 and nitrogen at position 6. In some forms, the unsubstituted $C_9$ bicyclic heterocyclic aromatic ring can have nitrogen or oxygen independently at positions 5 and 7. In some forms, the unsubstituted $C_9$ bicyclic heterocyclic aromatic ring can have nitrogen or oxygen independently at positions 5 and 8. In some forms, the unsubstituted $C_9$ bicyclic heterocyclic aromatic ring can have nitrogen or oxygen independently at positions 5 and 9.

In some forms, the unsubstituted $C_9$ bicyclic heterocyclic aromatic ring can have oxygen at any one of positions 2, 3, 4, 5, 7, 8, or 9 and nitrogen at any one of positions 1, 2, 3, 4, 6, 7, 8, or 9 not occupied by oxygen. In some forms, the unsubstituted $C_9$ bicyclic heterocyclic aromatic ring can have oxygen at position 2 and nitrogen at position 3. In some forms, the unsubstituted $C_9$ bicyclic heterocyclic aromatic ring can have oxygen at position 2 and nitrogen at position 4. In some forms, the unsubstituted $C_9$ bicyclic heterocyclic aromatic ring can have oxygen at position 2 and nitrogen at position 5. In some forms, the unsubstituted $C_9$ bicyclic heterocyclic aromatic ring can have oxygen at position 2 and nitrogen at position 6. In some forms, the unsubstituted $C_9$ bicyclic heterocyclic aromatic ring can have oxygen at position 2 and nitrogen at position 7. In some forms, the unsubstituted $C_9$ bicyclic heterocyclic aromatic ring can have oxygen at position 2 and nitrogen at position 8. In some forms, the unsubstituted $C_9$ bicyclic heterocyclic aromatic ring can have oxygen at position 2 and nitrogen at position 9.

In some forms, the unsubstituted $C_9$ bicyclic heterocyclic aromatic ring can have oxygen at position 3 and nitrogen at position 4. In some forms, the unsubstituted $C_9$ bicyclic heterocyclic aromatic ring can have oxygen at position 3 and nitrogen at position 5. In some forms, the unsubstituted $C_9$ bicyclic heterocyclic aromatic ring can have oxygen at position 3 and nitrogen at position 6. In some forms, the unsubstituted $C_9$ bicyclic heterocyclic aromatic ring can have oxygen at position 3 and nitrogen at position 7. In some forms, the unsubstituted $C_9$ bicyclic heterocyclic aromatic ring can have oxygen at position 3 and nitrogen at position 8. In some forms, the unsubstituted $C_9$ bicyclic heterocyclic aromatic ring can have oxygen at position 3 and nitrogen at position 9.

In some forms, the unsubstituted $C_9$ bicyclic heterocyclic aromatic ring can have oxygen at position 4 and nitrogen at position 5. In some forms, the unsubstituted $C_9$ bicyclic heterocyclic aromatic ring can have oxygen at position 4 and nitrogen at position 6. In some forms, the unsubstituted $C_9$ bicyclic heterocyclic aromatic ring can have oxygen at position 4 and nitrogen at position 7. In some forms, the unsubstituted $C_9$ bicyclic heterocyclic aromatic ring can have oxygen at position 4 and nitrogen at position 8. In some forms, the unsubstituted $C_9$ bicyclic heterocyclic aromatic ring can have oxygen at position 4 and nitrogen at position 9.

In some forms, the unsubstituted $C_9$ bicyclic heterocyclic aromatic ring can have oxygen at position 5 and nitrogen at position 6. In some forms, the unsubstituted $C_9$ bicyclic heterocyclic aromatic ring can have oxygen at position 5 and nitrogen at position 7. In some forms, the unsubstituted $C_9$ bicyclic heterocyclic aromatic ring can have oxygen at position 5 and nitrogen at position 8. In some forms, the unsubstituted $C_9$ bicyclic heterocyclic aromatic ring can have oxygen at position 5 and nitrogen at position 9.

In some forms, the unsubstituted $C_9$ bicyclic heterocyclic aromatic ring can have oxygen at position 7 and nitrogen at position 8. In some forms, the unsubstituted $C_9$ bicyclic heterocyclic aromatic ring can have oxygen at position 7 and nitrogen at position 9. In some forms, the unsubstituted $C_9$ bicyclic heterocyclic aromatic ring can have oxygen at position 8 and nitrogen at position 9.

In some forms, the unsubstituted $C_9$ bicyclic heterocyclic aromatic ring can have nitrogen at any one of positions 1, 2, 3, 4, 5, 6, 7, 8, or 9 and oxygen at any one of positions 2, 3, 4, 7, 8, or 9 not occupied by nitrogen. In some forms, the unsubstituted $C_9$ bicyclic heterocyclic aromatic ring can have nitrogen at position 1 and oxygen at position 2. In some forms, the unsubstituted $C_9$ bicyclic heterocyclic aromatic ring can have nitrogen at position 1 and oxygen at position 3. In some forms, the unsubstituted $C_9$ bicyclic heterocyclic aromatic ring can have nitrogen at position 1 and oxygen at position 4. In some forms, the unsubstituted $C_9$ bicyclic heterocyclic aromatic ring can have nitrogen at position 1 and oxygen at position 5. In some forms, the unsubstituted $C_9$ bicyclic heterocyclic aromatic ring can have nitrogen at position 1 and oxygen at position 7. In some forms, the unsubstituted $C_9$ bicyclic heterocyclic aromatic ring can have nitrogen at position 1 and oxygen at position 8. In some forms, the unsubstituted $C_9$ bicyclic heterocyclic aromatic ring can have nitrogen at position 1 and oxygen at position 9.

In some forms, the unsubstituted $C_9$ bicyclic heterocyclic aromatic ring can have nitrogen at position 2 and oxygen at position 3. In some forms, the unsubstituted $C_9$ bicyclic heterocyclic aromatic ring can have nitrogen at position 2 and oxygen at position 4. In some forms, the unsubstituted $C_9$ bicyclic heterocyclic aromatic ring can have nitrogen at position 2 and oxygen at position 5. In some forms, the unsubstituted $C_9$ bicyclic heterocyclic aromatic ring can have nitrogen at position 2 and oxygen at position 7. In some forms, the unsubstituted $C_9$ bicyclic heterocyclic aromatic ring can have nitrogen at position 2 and oxygen at position 8. In some forms, the unsubstituted $C_9$ bicyclic heterocyclic aromatic ring can have nitrogen at position 2 and oxygen at position 9.

In some forms, the unsubstituted $C_9$ bicyclic heterocyclic aromatic ring can have nitrogen at position 3 and oxygen at position 4. In some forms, the unsubstituted $C_9$ bicyclic heterocyclic aromatic ring can have nitrogen at position 3 and oxygen at position 5. In some forms, the unsubstituted $C_9$ bicyclic heterocyclic aromatic ring can have nitrogen at position 3 and oxygen at position 7. In some forms, the unsubstituted $C_9$ bicyclic heterocyclic aromatic ring can have nitrogen at position 3 and oxygen at position 8. In some forms, the unsubstituted $C_9$ bicyclic heterocyclic aromatic ring can have nitrogen at position 3 and oxygen at position 9.

In some forms, the unsubstituted $C_9$ bicyclic heterocyclic aromatic ring can have nitrogen at position 4 and oxygen at position 5. In some forms, the unsubstituted $C_9$ bicyclic heterocyclic aromatic ring can have nitrogen at position 4 and oxygen at position 7. In some forms, the unsubstituted $C_9$ bicyclic heterocyclic aromatic ring can have nitrogen at position 4 and oxygen at position 8. In some forms, the unsubstituted $C_9$ bicyclic heterocyclic aromatic ring can have nitrogen at position 4 and oxygen at position 9.

In some forms, the unsubstituted $C_9$ bicyclic heterocyclic aromatic ring can have nitrogen at position 5 and oxygen at position 7. In some forms, the unsubstituted $C_9$ bicyclic heterocyclic aromatic ring can have nitrogen at position 5 and oxygen at position 8. In some forms, the unsubstituted $C_9$ bicyclic heterocyclic aromatic ring can have nitrogen at position 5 and oxygen at position 9.

In some forms, the unsubstituted $C_9$ bicyclic heterocyclic aromatic ring can have nitrogen at position 6 and oxygen at position 7. In some forms, the unsubstituted $C_9$ bicyclic heterocyclic aromatic ring can have nitrogen at position 6 and oxygen at position 8. In some forms, the unsubstituted $C_9$ bicyclic heterocyclic aromatic ring can have nitrogen at position 6 and oxygen at position 9.

In some forms, the unsubstituted $C_9$ bicyclic heterocyclic aromatic ring can have nitrogen at position 7 and oxygen at position 8. In some forms, the unsubstituted $C_9$ bicyclic heterocyclic aromatic ring can have nitrogen at position 7 and oxygen at position 9. In some forms, the unsubstituted $C_9$ bicyclic heterocyclic aromatic ring can have nitrogen at position 8 and oxygen at position 9.

In some forms, m is an integer from 0 to 10. In some forms, m can be an integer from 0 to 10, 1 to 10, 2 to 10, 3 to 10, 4 to 10, 5 to 10, 6 to 10, 7 to 10, 8 to 10, 9 to 10, 0 to 9, 1 to 9, 2 to 9, 3 to 9, 4 to 9, 5 to 9, 6 to 9, 7 to 9, 8 to 9, 0 to 8, 1 to 8, 2 to 8, 3 to 8, 4 to 8, 5 to 8, 6 to 8, 7 to 8, 0 to 7, 1 to 7, 2 to 7, 3 to 7, 4 to 7, 5 to 7, 6 to 7, 0 to 6, 1 to 6, 2 to 6, 3 to 6, 4 to 6, 5 to 6, 0 to 5, 1 to 5, 2 to 5, 3 to 5, 4 to 5, 0 to 4, 1 to 4, 2 to 4, 3 to 4, 0 to 3, 1 to 3, 2 to 3, 0 to 2, 1 to 2, and 0 to 1. In some forms, m can be 0, 1, 2, 3, 4, 5, 6, 7, 8, 9, or 10.

In some forms, n is an integer from 0 to 10. In some forms, n can be an integer from 0 to 10, 1 to 10, 2 to 10, 3 to 10, 4 to 10, 5 to 10, 6 to 10, 7 to 10, 8 to 10, 9 to 10, 0 to 9, 1 to 9, 2 to 9, 3 to 9, 4 to 9, 5 to 9, 6 to 9, 7 to 9, 8 to 9, 0 to 8, 1 to 8, 2 to 8, 3 to 8, 4 to 8, 5 to 8, 6 to 8, 7 to 8, 0 to 7, 1 to 7, 2 to 7, 3 to 7, 4 to 7, 5 to 7, 6 to 7, 0 to 6, 1 to 6, 2 to 6, 3 to 6, 4 to 6, 5 to 6, 0 to 5, 1 to 5, 2 to 5, 3 to 5, 4 to 5, 0 to 4, 1 to 4, 2 to 4, 3 to 4, 0 to 3, 1 to 3, 2 to 3, 0 to 2, 1 to 2, and 0 to 1. In some forms, n can be 0, 1, 2, 3, 4, 5, 6, 7, 8, 9, or 10.

In some forms, m+n can be an integer from 0 to 20.
0 to 20, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 0 to 19, 1 to 19, 2 to 19, 3 to 19, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 0 to 18, 1 to 18, 2 to 18, 3 to 18, 4 to 18, 5 to 18, 6 to 18, 7 to 18, 8 to 18, 9 to 18, 10 to 18, 11 to 18, 12 to 18, 13 to 18, 14 to 18, 15 to 18, 16 to 18, 17 to 18, 0 to 17, 1 to 17, 2 to 17, 3 to 17, 4 to 17, 5 to 17, 6 to 17, 7 to 17, 8 to 17, 9 to 17, 10 to 17, 11 to 17, 12 to 17, 13 to 17, 14 to 17, 15 to 17, 16 to 17, 0 to 16, 1 to 16, 2 to 16, 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 0 to 15, 1 to 15, 2 to 15, 3 to 15, 4 to 15, 5 to 15, 6 to 15, 7 to 15, 8 to 15, 9 to 15, 10 to 15, 11 to 15, 12 to 15, 13 to 15, 14 to 15, 0 to 14, 1 to 14, 2 to 14, 3 to 14, 4 to 14, 5 to 14, 6 to 14, 7 to 14, 8 to 14, 9 to 14, 10 to 14, 11 to 14, 12 to 14, 13 to 14, 0 to 13, 1 to 13, 2 to 13, 3 to 3, 4 to 13, 5 to 13, 6 to 13, 7 to 13, 8 to 13, 9 to 13, 10 to 13, 11 to 13, 12 to 13, 0 to 12, 1 to 12, 2 to 12, 3 to 12, 4 to 12, 5 to 12, 6 to 12, 7 to 12, 8 to 12, 9 to 12, 10 to 12, 11 to 12, 0 to 11, 1 to 11, 2 to 11, 3 to 11, 4 to 11, 5 to 11, 6 to 11, 7 to 11, 8 to 11, 9 to 11, 10 to 11, 0 to 10, 1 to 10, 2 to 10, 3 to 10, 4 to 10, 5 to 10, 6 to 10, 7 to 10, 8 to 10, 9 to 10, 0 to 9, 1 to 9, 2 to 9, 3 to 9, 4 to 9, 5 to 9, 6 to 9, 7 to 9, 8 to 9, 0 to 8, 1 to 8, 2 to 8, 3 to 8, 4 to 8, 5 to 8, 6 to 8, 7 to 8, 0 to 7, 1 to 7, 2 to 7, 3 to 7, 4 to 7, 5 to 7, 6 to 7, 0 to 6, 1 to 6, 2 to 6, 3 to 6, 4 to 6, 5 to 6, 0 to 5, 1 to 5, 2 to 5, 3 to 5, 4 to 5, 0 to 4, 1 to 4, 2 to 4, 3 to 4, 0 to 3, 1 to 3, 2 to 3, 0 to 2, 1 to 2, and 0 to 1. In some forms, m+n can be 0, 1, 2, 3, 4, 5, 6, 7, 8, 9, 10, 11, 12, 13, 14, 15, 16, 17, 18, 19, or 20.

In some forms, the compound can be defined according to Formula (II):

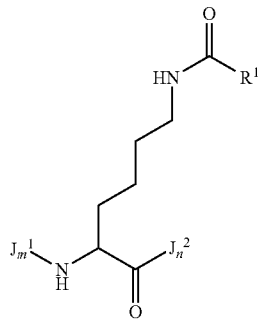

Formula (II)

where each instance of $J^1$ and $J^2$ is independently any α-amino acid; where $R^1$ is a conjugated/delocalized group, comprising an unsubstituted or substituted, heterocyclic or carbocyclic, aromatic ring (monocyclic, bicyclic, tricyclic, tetracyclic), or unsubstituted or substituted alkenyl or alkynyl, wherein the conjugated/delocalized group includes p-orbitals which allow for pi-electrons to become delocalized; and where m and n are each independently integers from 0 to 10, where at least one of m or n is not 0. In some forms, at least one of m or n is not 0. In some forms, both of m or n are 0.

In some forms, the compound can be defined according to Formula (III):

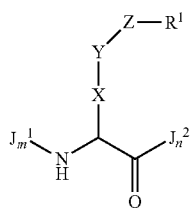

Formula (III)

where each instance of $J^1$ and $J^2$ is independently any α-amino acid; where X is an unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl; where Y is $NR^3$, O, or S; where Z is —CO—, —CS—, —CNR$^4$—, —SO—, and —SO$_2$—; where $R^3$ and $R^4$ are independently H or $C_{1-10}$ hydrocarbyl, $C_{1-10}$ carbocyclyl or $C_{1-10}$ heterocyclyl; where $R^1$ is a conjugated/delocalized group, such as an unsubstituted or substituted, heterocyclic or carbocyclic, aromatic ring (monocyclic, bicyclic, tricyclic, tetracyclic), unsubstituted or substituted alkenyl or alkynyl, wherein the conjugated/delocalized group includes p-orbitals which allow for pi-electrons to become delocalized; and where m and n are each independently integers from 0 to 10. In some forms, at least one of m or n is not 0. In some forms, both of m or n are 0.

In some forms, the compound can be defined according to Formula (IV):

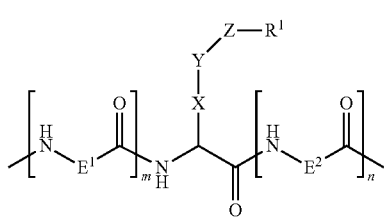

Formula (IV)

where each instance of $E^1$ and $E^2$ is independently an unsubstituted or substituted $C_{1-10}$ $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl, or O, S, or $NR^5$; where X is an unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl; where Y is $NR^3$, O, or S; where Z is —CO—, —CS—, —CNR$^4$—, —SO—, or —SO$_2$—; where $R^3$, $R^4$, and $R^5$ are independently a H, $C_{1-10}$ hydrocarbyl, $C_{1-10}$ carbocyclyl or $C_{1-10}$ heterocyclyl; where $R^1$ is a conjugated/delocalized group, such as an unsubstituted or substituted, heterocyclic or carbocyclic, aromatic ring (monocyclic, bicyclic, tricyclic, tetracyclic) or unsubstituted or substituted alkenyl or alkynyl, wherein the conjugated/delocalized group includes p-orbitals which allow for pi-electrons to become delocalized; and where m and n are each independently integers from 0 to 10. In some forms, at least one of m or n is not 0. In some forms, both of m or n are 0.

In some forms of the compound, at least two of the instances of $B^1$ linking units can comprise side chains, where two of the side chains of the $B^1$ linking units can be covalently coupled to each other forming a circular oligomer.

In some forms of the compound, at least two of the instances of $B^2$ linking units can comprise side chains, where two of the side chains of the $B^2$ linking units can be covalently coupled to each other forming a circular oligomer.

In some forms of the compound, at least one of the instances of $B^1$ linking units and at least one of the instances of $B^2$ linking units can comprise side chains, where two of the side chains of the $B^1$ and $B^2$ linking units can be covalently coupled to each other forming a circular oligomer.

In some forms of the compound, at least two of the instances of $J^1$ amino acids can comprise side chains, where two of the side chains of the $J^1$ amino acids can be covalently coupled to each other forming a circular oligomer.

In some forms of the compound, at least two of the instances of $J^2$ amino acids can comprise side chains, where two of the side chains of the $J^2$ amino acids can be covalently coupled to each other forming a circular oligomer.

In some forms of the compound, at least one of the instances of $J^1$ amino acids and at least one of the instances of $J^2$ amino acids can comprise side chains, where two of the side chains of the $J^1$ and $J^2$ amino acids can be covalently coupled to each other forming a circular oligomer.

In some forms of the compound, at least two of the instances of $E^1$ can comprise side chains, where two of the side chains of the $E^1$ can be covalently coupled to each other forming a circular oligomer.

In some forms of the compound, at least two of the instances of $E^2$ can comprise side chains, where two of the side chains of the $E^2$ can be covalently coupled to each other forming a circular oligomer.

In some forms of the compound, at least one of the instances of $E^1$ and at least one of the instances of $E^2$ can comprise side chains, where two of the side chains of the $E^1$ and $E^2$ can be covalently coupled to each other forming a circular oligomer.

In some forms, the compound can be defined according to Formula (V):

Formula (V)

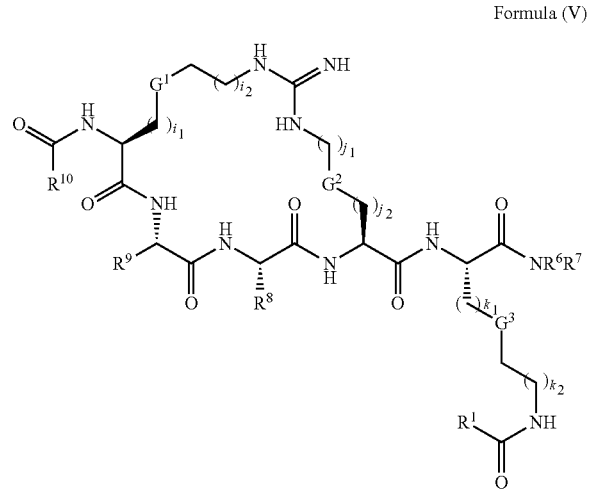

where $R^1$ is a conjugated/delocalized group, comprising an unsubstituted or substituted, heterocyclic or carbocyclic, aromatic ring (monocyclic, bicyclic, tricyclic, tetracyclic) or unsubstituted or substituted alkenyl or alkynyl, wherein the conjugated/delocalized group includes p-orbitals which allow for pi-electrons to become delocalized; where $R^6$, $R^7$, $R^8$, $R^9$, and $R^{10}$ are independently H or $C_{1-10}$ hydrocarbyl, $C_{1-10}$ carbocyclyl or $C_{1-10}$ heterocyclyl; where each of $G^1$, $G^2$, and $G^3$ is an unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, $C_{1-10}$ heterocyclyl, or 5 to 9-membered heteroaryl; and where $i_1$, $i_2$, $j_1$, $j_2$, $k_1$, $k_2$ are each independently integers from 0 to 10.

In some forms, $R^8$ and $R^9$ are the side chains of an amino acid, which can be independently selected from the side chains of the amino acids Lys, Gln, Thr, Ala, Arg, Ser, Leu, Trp, and Gly.

In some forms, $R^{10}$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, $R^{10}$ can be H. In some forms, $R^{10}$ can be carboxybenzyl (Cbz). In some forms, $R^{10}$ can be acetyl. In some forms, $R^{10}$ can be benzenecarbonyl. In some forms, $R^{10}$ can be benzenemethylcarbonyl. In some forms, $R^{10}$ can be benzeneethylcarbonyl. In some forms, $R^{10}$ can be benzenepropylcarbonyl. In some forms, $R^{10}$ can be naphthalenemethylcarbonyl. In some forms, $R^{10}$ can be naphthaleneethylcarbonyl.

In some forms, $i_1$ is an integer from 0 to 10. In some forms, $i_1$ can be an integer from 0 to 10, 1 to 10, 2 to 10, 3 to 10, 4 to 10, 5 to 10, 6 to 10, 7 to 10, 8 to 10, 9 to 10, 0 to 9, 1 to 9, 2 to 9, 3 to 9, 4 to 9, 5 to 9, 6 to 9, 7 to 9, 8 to 9, 0 to 8, 1 to 8, 2 to 8, 3 to 8, 4 to 8, 5 to 8, 6 to 8, 7 to 8, 0 to 7, 1 to 7, 2 to 7, 3 to 7, 4 to 7, 5 to 7, 6 to 7, 0 to 6, 1 to 6, 2 to 6, 3 to 6, 4 to 6, 5 to 6, 0 to 5, 1 to 5, 2 to 5, 3 to 5, 4 to 5, 0 to 4, 1 to 4, 2 to 4, 3 to 4, 0 to 3, 1 to 3, 2 to 3, 0 to 2, 1 to 2, and 0 to 1. In some forms, $i_1$ can be 0, 1, 2, 3, 4, 5, 6, 7, 8, 9, or 10.

In some forms, $i_2$ is an integer from 0 to 10. In some forms, $i_2$ can be an integer from 0 to 10, 1 to 10, 2 to 10, 3 to 10, 4 to 10, 5 to 10, 6 to 10, 7 to 10, 8 to 10, 9 to 10, 0 to 9, 1 to 9, 2 to 9, 3 to 9, 4 to 9, 5 to 9, 6 to 9, 7 to 9, 8 to 9, 0 to 8, 1 to 8, 2 to 8, 3 to 8, 4 to 8, 5 to 8, 6 to 8, 7 to 8, 0 to 7, 1 to 7, 2 to 7, 3 to 7, 4 to 7, 5 to 7, 6 to 7, 0 to 6, 1 to 6, 2 to 6, 3 to 6, 4 to 6, 5 to 6, 0 to 5, 1 to 5, 2 to 5, 3 to 5, 4 to 5, 0 to 4, 1 to 4, 2 to 4, 3 to 4, 0 to 3, 1 to 3, 2 to 3, 0 to 2, 1 to 2, and 0 to 1. In some forms, $i_2$ can be 0, 1, 2, 3, 4, 5, 6, 7, 8, 9, or 10.

In some forms, $j_1$ is an integer from 0 to 10. In some forms, $j_1$ can be an integer from 0 to 10, 1 to 10, 2 to 10, 3 to 10, 4 to 10, 5 to 10, 6 to 10, 7 to 10, 8 to 10, 9 to 10, 0 to 9, 1 to 9, 2 to 9, 3 to 9, 4 to 9, 5 to 9, 6 to 9, 7 to 9, 8 to 9, 0 to 8, 1 to 8, 2 to 8, 3 to 8, 4 to 8, 5 to 8, 6 to 8, 7 to 8, 0 to 7, 1 to 7, 2 to 7, 3 to 7, 4 to 7, 5 to 7, 6 to 7, 0 to 6, 1 to 6, 2 to 6, 3 to 6, 4 to 6, 5 to 6, 0 to 5, 1 to 5, 2 to 5, 3 to 5, 4 to 5, 0 to 4, 1 to 4, 2 to 4, 3 to 4, 0 to 3, 1 to 3, 2 to 3, 0 to 2, 1 to 2, and 0 to 1. In some forms, $j_1$ can be 0, 1, 2, 3, 4, 5, 6, 7, 8, 9, or 10.

In some forms, $j_2$ is an integer from 0 to 10. In some forms, $j_2$ can be an integer from 0 to 10, 1 to 10, 2 to 10, 3 to 10, 4 to 10, 5 to 10, 6 to 10, 7 to 10, 8 to 10, 9 to 10, 0 to 9, 1 to 9, 2 to 9, 3 to 9, 4 to 9, 5 to 9, 6 to 9, 7 to 9, 8 to 9, 0 to 8, 1 to 8, 2 to 8, 3 to 8, 4 to 8, 5 to 8, 6 to 8, 7 to 8, 0 to 7, 1 to 7, 2 to 7, 3 to 7, 4 to 7, 5 to 7, 6 to 7, 0 to 6, 1 to 6, 2 to 6, 3 to 6, 4 to 6, 5 to 6, 0 to 5, 1 to 5, 2 to 5, 3 to 5, 4 to 5, 0 to 4, 1 to 4, 2 to 4, 3 to 4, 0 to 3, 1 to 3, 2 to 3, 0 to 2, 1 to 2, and 0 to 1. In some forms, $j_2$ can be 0, 1, 2, 3, 4, 5, 6, 7, 8, 9, or 10.

In some forms, $k_1$ is an integer from 0 to 10. In some forms, $k_1$ can be an integer from 0 to 10, 1 to 10, 2 to 10, 3 to 10, 4 to 10, 5 to 10, 6 to 10, 7 to 10, 8 to 10, 9 to 10, 0 to 9, 1 to 9, 2 to 9, 3 to 9, 4 to 9, 5 to 9, 6 to 9, 7 to 9, 8 to 9, 0 to 8, 1 to 8, 2 to 8, 3 to 8, 4 to 8, 5 to 8, 6 to 8, 7 to 8, 0 to 7, 1 to 7, 2 to 7, 3 to 7, 4 to 7, 5 to 7, 6 to 7, 0 to 6, 1 to 6, 2 to 6, 3 to 6, 4 to 6, 5 to 6, 0 to 5, 1 to 5, 2 to 5, 3 to 5, 4 to 5, 0 to 4, 1 to 4, 2 to 4, 3 to 4, 0 to 3, 1 to 3, 2 to 3, 0 to 2, 1 to 2, and 0 to 1. In some forms, $k_i$ can be 0, 1, 2, 3, 4, 5, 6, 7, 8, 9, or 10.

In some forms, $k_2$ is an integer from 0 to 10. In some forms, $k_2$ can be an integer from 0 to 10, 1 to 10, 2 to 10, 3 to 10, 4 to 10, 5 to 10, 6 to 10, 7 to 10, 8 to 10, 9 to 10, 0 to 9, 1 to 9, 2 to 9, 3 to 9, 4 to 9, 5 to 9, 6 to 9, 7 to 9, 8 to 9, 0 to 8, 1 to 8, 2 to 8, 3 to 8, 4 to 8, 5 to 8, 6 to 8, 7 to 8, 0 to 7, 1 to 7, 2 to 7, 3 to 7, 4 to 7, 5 to 7, 6 to 7, 0 to 6, 1 to 6, 2 to 6, 3 to 6, 4 to 6, 5 to 6, 0 to 5, 1 to 5, 2 to 5, 3 to 5, 4 to 5, 0 to 4, 1 to 4, 2 to 4, 3 to 4, 0 to 3, 1 to 3, 2 to 3, 0 to 2, 1 to 2, and 0 to 1. In some forms, $k_2$ can be 0, 1, 2, 3, 4, 5, 6, 7, 8, 9, or 10.

In some forms, the compound inhibits π-π-π stacking interactions. In some forms, the compound selectively targets the YEATS protein domain.

Also disclosed are pharmaceutical compositions comprising an effective amount of any of the disclosed compounds. In some forms, the composition can further comprise one or more pharmaceutically acceptable carriers or excipients. In some forms, the composition selectively inhibits π-π-π stacking interactions. In some forms, the composition selectively targets the YEATS protein domain. In some forms, the composition is effective for treating cancer. In some forms, the cancer is acute leukemia.

Also disclosed are methods for treating cancer, the method comprising administering any of the disclosed compositions to a subject in need thereof. In some forms, the subject has acute leukemia.

In certain forms, the compound includes a base peptide and a side chain, and is defined according to Formula (I):

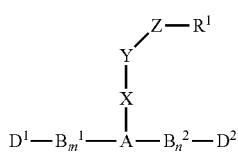

Formula (I)

where A is N or $CR^2$; each of $B^1$ and $B^2$ are independently bivalent linking groups that connect each unit by ester, amide, thioester, thioamide, imidate, imide, sulfonate, sulfonamide linkage in a head-to-tail manner; $D^1$ can be H or unsubstituted or substituted hydrocarbyl, carbocyclyl or heterocyclyl; $D^2$ can be H, $NH_2$, $NHR^{15}$, $NR^{16}R^{17}$, OH, $OR^{18}$, or unsubstituted or substituted hydrocarbyl, carbocyclyl or heterocyclyl; X is an unsubstituted or substituted $C_{1-10}$ alkyl, $C_{1-10}$ alkenyl, $C_{1-10}$ alkynyl, $C_{1-10}$ carbocyclyl or $C_{1-10}$ heteroalkyl, $C_{1-10}$ heteroalkenyl, $C_{1-10}$ heteroalkynyl, or $C_{1-10}$ heterocyclyl; Y is O, S or $NR^3$; Z is —CO—, —CS—, —$CNR^4$—, —SO—, and —$SO_2$—; $R^{15}$, $R^{16}$, $R^{17}$, and $R^{18}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; $R^2$, $R^3$, and $R^4$ are independently a H, $C_{1-10}$ hydrocarbyl, $C_{1-10}$ carbocyclyl or $C_{1-10}$ heterocyclyl; $R^1$ is a conjugated/delocalized group, including unsubstituted or substituted aromatic rings (monocyclic, bicyclic, tricyclic, tetracyclic), unsubstituted or substituted alkenyl or alkynyl, wherein the conjugated/delocalized group includes p-orbitals which allow for pi-electrons to become delocalized; and m and n are integers from 0 to 10. In some forms, at least one of m or n is not 0. In some forms, both of morn are 0.

In some forms, $B^1$ can be —NH—, —O—, —S—, or —$(CH_2)_p$—, where p is an integer from 1 to 6, for example 1, 2, 3, 4, 5, and 6. In some forms, the terminal $B^2$ can be —C(=O)—, —C(=NH)—, —C(=S)—, —S(=O)$_2$—, or -(representing a terminal bond on $B^2$). In some forms, $D^2$ can be H, $NH_2$, $NHR^{15}$, $NR^{16}R^{17}$, OH, $OR^{18}$, or unsubstituted or substituted hydrocarbyl, carbocyclyl or heterocyclyl, where $R^{15}$, $R^{16}$, $R^{17}$, and $R^{18}$ can be H or alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic.

In other forms, the compound includes a base peptide and a side chain, and is defined according to Formula (II):

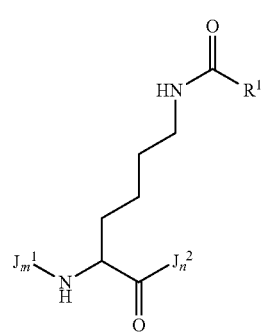

Formula (II)

where each of $J^1$ and $J^2$ are independently any α-amino acids; $R^1$ is a conjugated/delocalized group, comprising unsubstituted or substituted aromatic rings (monocyclic, bicyclic, tricyclic, tetracyclic), unsubstituted or substituted alkenyl or alkynyl, wherein the conjugated/delocalized group includes p-orbitals which allow for pi-electrons to become delocalized; and m and n are integers from 0 to 10. In some forms, at least one of m or n is not 0. In some forms, both of m or n are 0.

In other forms, the compound includes a base peptide and a side chain, and is defined according to Formula (III):

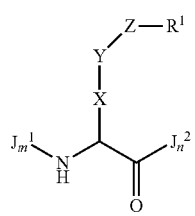

Formula (III)

where each of $J^1$ and $J^2$ are independently any α-amino acid; X is an unsubstituted or substituted $C_{1-10}$ alkyl, $C_{1-10}$ alkenyl, $C_{1-10}$ alkynyl, $C_{1-10}$ carbocyclyl or $C_{1-10}$ heteroalkyl, $C_{1-10}$ heteroalkenyl, $C_{1-10}$ heteroalkynyl, or $C_{1-10}$ heterocyclyl; Y is O, S or $NR^2$; Z is —CO—, —CS—, —$CNR^3$—, —SO—, and —$SO_2$—; $R^2$, $R^3$ are independently a H, $C_{1-10}$ hydrocarbyl, $C_{1-10}$ carbocyclyl or $C_{1-10}$ heterocyclyl; $R^1$ is a conjugated/delocalized group, including unsubstituted or substituted aromatic rings (monocyclic, bicyclic, tricyclic, tetracyclic), unsubstituted or substituted alkenyl or alkynyl, wherein the conjugated/delocalized group includes p-orbitals which allow for pi-electrons to become delocalized; and m and n are integers from 0 to 10. In some forms, at least one of m or n is not 0. In some forms, both of m or n are 0.

In other forms, the compound includes a base peptide and a side chain, and is defined according to Formula (IV):

Formula (IV)

where each of $E^1$ and $E^2$ is independently a O, S, $NR^2$, unsubstituted or substituted $C_{1-10}$ alkyl, $C_{1-10}$ alkenyl, $C_{1-10}$ alkynyl, $C_{1-10}$ carbocyclyl or $C_{1-10}$ heteroalkyl, $C_{1-10}$ heteroalkenyl, $C_{1-10}$ heteroalkynyl, or $C_{1-10}$ heterocyclyl; X is an unsubstituted or substituted $C_{1-10}$ alkyl, $C_{1-10}$ alkenyl, $C_{1-10}$ alkynyl, $C_{1-10}$ carbocyclyl or $C_{1-10}$ heteroalkyl, $C_{1-10}$ heteroalkenyl, $C_{1-10}$ heteroalkynyl, or $C_{1-10}$ heterocyclyl; Y is O, S or $NR^3$; Z is —CO—, —CS—, —$CNR^4$—, —SO—, or —$SO_2$—; $R^2$, $R^3$, and $R^4$ are independently a H, $C_{1-10}$ hydrocarbyl, $C_{1-10}$ carbocyclyl or $C_{1-10}$ heterocyclyl; $R^1$ is a conjugated/delocalized group, including unsubstituted or substituted aromatic rings (monocyclic, bicyclic, tricyclic, tetracyclic), unsubstituted or substituted alkenyl or alkynyl, wherein the conjugated/delocalized group includes p-orbitals which allow for pi-electrons to become delocalized; and m and n are integers from 0 to 10. In some forms, at least one of m or n is not 0. In some forms, both of m or n are 0.

In alternative forms, the compound includes a cyclic peptide and is defined according to Formula (V):

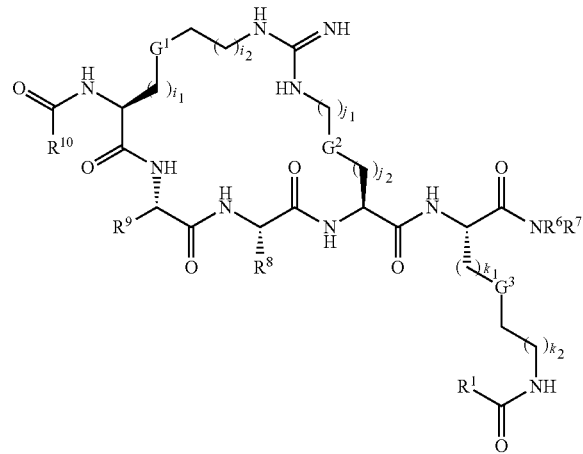

Formula (V)

where $R^1$ is a conjugated/delocalized group, comprising unsubstituted or substituted aromatic rings (monocyclic, bicyclic, tricyclic, tetracyclic), unsubstituted or substituted alkenyl or alkynyl, wherein the conjugated/delocalized group includes p-orbitals which allow for pi-electrons to become delocalized; $R^6$, $R^7$, $R^8$, $R^9$, and $R^{10}$ are independently a H, $C_{1-10}$ hydrocarbyl, $C_{1-10}$ carbocyclyl or $C_{1-10}$ heterocyclyl; each of $G^1$, $G^2$, and $G^3$ is an unsubstituted or substituted $C_{1-10}$ alkyl, $C_{1-10}$ alkenyl, $C_{1-10}$ alkynyl, $C_{1-10}$ carbocyclyl or $C_{1-10}$ heteroalkyl, $C_{1-10}$ heteroalkenyl, $C_{1-10}$ heteroalkynyl, $C_{1-10}$ heterocyclyl, or 5 to 9-membered heteroaryl; and $i_1$, $i_2$, $j_1$, $j_2$, $k_1$, $k_2$ are integers from 0 to 10.

In some forms, $R^8$ and $R^9$ are the side chains of an amino acid, which can be independently selected from the side chains of the amino acids Lys, Gln, Thr, Ala, Arg, Ser, Leu, Trp, and Gly.

In some forms, $R^{10}$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, $R^{10}$ can be H. In some forms, $R^{10}$ can be carboxybenzyl (Cbz). In some forms, $R^{10}$ can be acetyl. In some forms, $R^{10}$ can be benzenecarbonyl. In some forms, $R^{10}$ can be benzenemethylcarbonyl. In some forms, $R^{10}$ can be benzeneethylcarbonyl. In some forms, $R^{10}$ can be benzenepropylcarbonyl. In some forms, $R^{10}$ can be naphthalenemethylcarbonyl. In some forms, $R^{10}$ can be naphthaleneethylcarbonyl.

In some other forms, the composition includes a compound, or a pharmaceutically acceptable salt thereof, that comprises a base oligomer and a side chain. In some forms, the compound can be defined according to Formula (VI):

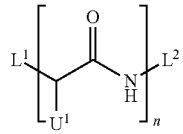

Formula (VI)

where n is an integer greater than 1, preferably in the range of 2-10.

In some forms of compounds of Formula (VI), $L^1$ and $L^2$ are independently selected from a hydrogen, —$NH_2$, unsubstituted or substituted $C_{1-10}$ alkyl, $C_{1-10}$ alkenyl, $C_{1-10}$ alkynyl, $C_{3-10}$ carbocyclyl, $C_{1-10}$ heteroalkyl, $C_{1-10}$ heteroalkenyl, $C_{1-10}$ heteroalkynyl, or $C_{3-10}$ heterocyclyl. In some forms, $L^1$ is preferably an —$NH_2$ group.

In some forms of compounds of Formula (VI), $L^2$ is selected from a hydrogen or the following group:

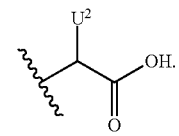

In some forms of compounds of Formula (VI), $U^1$ and $U^2$ are each independently selected from the following groups: a proline structure,

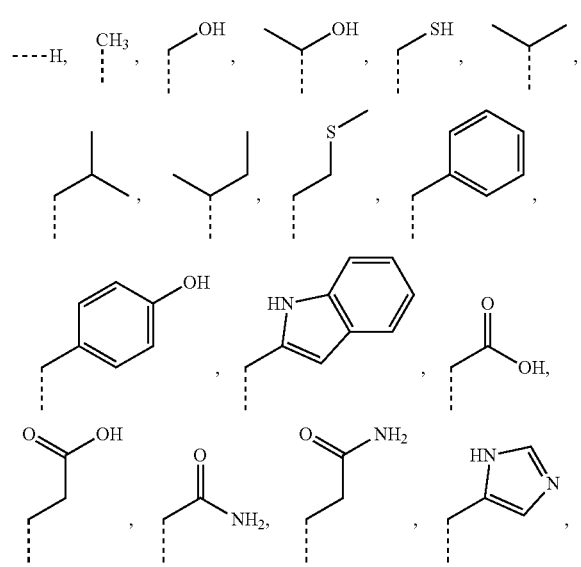

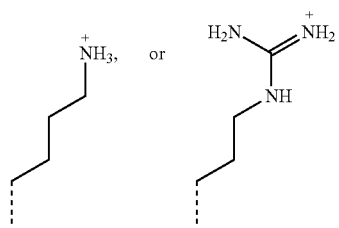

where the dashed lines denote the linkage point of the above groups.

In some instances, $U^1$ may form a proline structure, where $U^1$ is a $C_3$ alkyl that forms a cyclic structure with the nitrogen of the NH group shown in the bracketed repeating unit of the inhibitor of Formula (IV) and the hydrogen of the NH group is absent. In some instances, $U^2$ may form a proline structure, where $U^2$ is a $C_3$ alkyl that forms a cyclic structure with the nitrogen of the NH group shown in the bracketed repeating unit of the inhibitor of Formula (IV) and the hydrogen of the NH group is absent. The compounds of Formula (VI) include at least one $U^1$ or $U^2$ group which is defined according to the following structure:

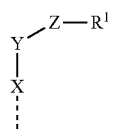

where the dashed line denotes the linkage point of above structure and where $R^1$ can be a conjugated/delocalized group. In some forms, the conjugated/delocalized group can be an unsubstituted or substituted, heterocyclic or carbocyclic, aromatic ring (such as monocyclic, bicyclic, tricyclic, tetracyclic) or unsubstituted or substituted alkenyl or alkynyl group, wherein the conjugated/delocalized group includes p-orbitals which allow for pi-electrons to become delocalized.

In some forms of compounds of Formula (VI), X can be unsubstituted or substituted $C_{1-10}$ alkyl, $C_{1-10}$ alkenyl, $C_{1-10}$ alkynyl, $C_{3-10}$ carbocyclyl, $C_{1-10}$ heteroalkyl, $C_{1-10}$ heteroalkenyl, $C_{1-10}$ heteroalkynyl, or $C_{3-10}$ heterocyclyl. In some forms, X can be an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, X can be —$(CH_2)_p$—, where p is an integer from 1 to 6. In some forms, X can be —$(CH_2)_p$—, where p is an integer from 2 to 5. In some forms, X can be —$(CH_2)_p$—, where p is 3 or 4. In some forms, X can be —$(CH_2)_p$—, where p is 4.

In some forms of compounds of Formula (VI), Y can be —$NR^3$, —O—, or —S—. In some forms, $R^3$ can be H or $C_{1-10}$ hydrocarbyl, $C_{3-10}$ carbocyclyl, or $C_{3-10}$ heterocyclyl. In some forms, $R^3$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms Y can be $NR^3$, and $R^3$ can be H.

In some forms of compounds of Formula (VI), Z can be —CO—, —CS—, —$CNR^4$—, —SO—, or —$SO_2$—. In some forms, Z can be —CO—. In some forms, $R^4$ can be H or $C_{1-10}$ hydrocarbyl, $C_{3-10}$ carbocyclyl, or $C_{3-10}$ heterocyclyl. In some forms, $R^4$ can be H or an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group.

In yet other forms, the composition includes a compound, or a pharmaceutically acceptable salt thereof, that comprises a base oligomer and a side chain. In some forms, the compound can be defined according to Formula (VII):

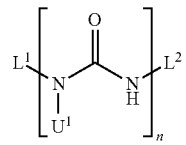

Formula (VII)

where n, $L^1$, and $L^2$ groups are defined in the same manner as in Formula (VI). The compounds of Formula (VII) include $U^1$ groups as defined in Formula (VI) and include at least one $U^1$ or $U^2$ group which defined according to the following structure:

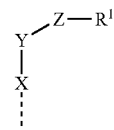

where the dashed line denotes the linkage point of above structure and wherein X, Y, Z, and $R^1$ are defined in the same manner as in Formula (VI).

In still some other forms, the composition includes a compound, or a pharmaceutically acceptable salt thereof, that comprises a cyclized oligomer having side chain(s) thereon.

In some forms, the compound can be defined according to Formula (VIII):

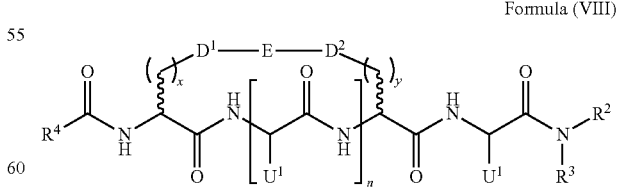

Formula (VIII)

where n is an integer greater than 1, preferably in the range of 2-10; and x and y are independently integers from 1-10. The compounds of Formula (VIII) include $U^1$ groups as defined in Formula (VI) and include at least one $U^1$ group defined according to the following structure:

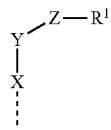

where the dashed line denotes the linkage point of above structure and wherein X, Y, Z, and $R^1$ are defined in the same manner as in Formula (VI).

In some forms of compounds of Formula (VIII), $R^2$ and $R^3$ are each independently selected from a hydrogen, $C_{1-10}$ hydrocarbyl, $C_{3-10}$ carbocyclyl, or $C_{3-10}$ heterocyclyl; and $R^4$ is selected from a hydrogen, —OH, —NH$_2$, $C_{1-10}$ hydrocarbyl, $C_{3-10}$ carbocyclyl, or $C_{3-10}$ heterocyclyl.

In some forms of compounds of Formula (VIII), $D^1$ and $D^2$ are each independently selected from an unsubstituted or substituted $C_{1-10}$ alkyl, $C_{1-10}$ alkenyl, $C_{1-10}$ alkynyl, $C_{3-10}$ carbocyclyl, $C_{1-10}$ heteroalkyl, $C_{1-10}$ heteroalkenyl, $C_{1-10}$ heteroalkynyl, or $C_{3-10}$ heterocyclyl; and E is defined according to the following structure:

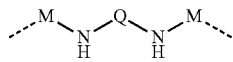

where the dashed lines denote the linkage point of above structure and where each M can independently be an unsubstituted or substituted $C_{1-10}$ alkyl, $C_{1-10}$ alkenyl, $C_{1-10}$ alkynyl, $C_{3-10}$ carbocyclyl, $C_{1-10}$ heteroalkyl, $C_{1-10}$ heteroalkenyl, $C_{1-10}$ heteroalkynyl, or $C_{3-10}$ heterocyclyl. In some forms, each M can be an alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic group. In some forms, M can be —(CH$_2$)$_p$—, where p is an integer from 1 to 6. In some forms, X can be —(CH$_2$)$_p$—, where p is an integer from 2 to 5. In some forms, X can be —(CH$_2$)$_p$—, where p is 3 or 4. In some forms, X can be —(CH$_2$)$_p$—, where p is 4; and where Q can be —CH$_2$—, C=NH, C(O), S(O), or S(O)$_2$. In some forms, Z can be C(O) or C=NH. In some forms, Q can be —(CH$_2$)$_p$—, where p is an integer from 1 to 6. In some forms, Q can be —(CH$_2$)$_p$—, where p is an integer from 2 to 5. In some forms, Q can be —(CH$_2$)$_p$—, where p is 3 or 4.

In some forms, the compounds can include a "sequence" of sign chains (such as the side chains of the bivalent linking units or monomer units (e.g., $B^1$, $B^2$, $J^1$, $J^2$, $E^1$, $E^2$) where the sequence of side chains corresponds to side chains of amino acids. In this regard, side chain refers to, for example, $R^{11}$, $U^1$, $U^2$, $R^8$, $R^9$, or $R^{10}$, or the side chain of a bivalent linking unit or monomer unit (e.g., Bi, $B^2$, $J^1$, $J^2$, $E^1$, $E^2$). The following discussion of the sequence of side chains refers to any of these side chains or other side chains as described elsewhere herein. In some forms, the side chains can be independently selected from the side chains of the amino acids Lys, Gln, Thr, Ala, Arg, Ser, Leu, Trp, and Gly.

In some forms, the sequence of signs chains of bivalent units or monomer units can comprise the amino acid side chain sequence of the peptide ARK. In some forms, the sequence of signs chains can comprise the amino acid side chain sequence of the peptide TARK (amino acids 2 to 5 of SEQ ID NO:4). In some forms, the sequence of signs chains can comprise the amino acid side chain sequence of the peptide QTARK (SEQ ID NO:4). In some forms, the sequence of signs chains can comprise the amino acid side chain sequence of the peptide KQTARK (SEQ ID NO:5). In some forms, the sequence of signs chains can comprise the amino acid side chain sequence of the peptide ARKSTGG (amino acids 4 to 10 of SEQ ID NO:6). In some forms, the sequence of signs chains can comprise the amino acid side chain sequence of the peptide TARKSTGG (amino acids 3 to 10 of SEQ ID NO:6). In some forms, the sequence of signs chains can comprise the amino acid side chain sequence of the peptide QTARKSTGG (amino acids 2 to 10 of SEQ ID NO:6). In some forms, the sequence of signs chains can comprise the amino acid side chain sequence of the peptide KQTARKSTGG (SEQ ID NO:6).

In some forms, the sequence of signs chains can comprise the amino acid side chain sequence of the peptide (T/A/S)ARK (amino acids 3 to 6 of SEQ ID NO:7). In some forms, the sequence of signs chains can comprise the amino acid side chain sequence of the peptide Q(T/A/S)ARK (amino acids 2 to 6 of SEQ ID NO:7). In some forms, the sequence of signs chains can comprise the amino acid side chain sequence of the peptide KQ(T/A/S)ARK (SEQ ID NO:7). In some forms, the sequence of signs chains can comprise the amino acid side chain sequence of the peptide (T/A/S)ARKSTGG (amino acids 3 to 10 of SEQ ID NO:8). In some forms, the sequence of signs chains can comprise the amino acid side chain sequence of the peptide Q(T/A/S)ARKSTGG (amino acids 2 to 10 of SEQ ID NO:8). In some forms, the sequence of signs chains can comprise the amino acid side chain sequence of the peptide KQ(T/A/S)ARKSTGG (SEQ ID NO:8).

In some forms, the sequence of signs chains can comprise the amino acid side chain sequence of the peptide AARK (amino acids 3 to 6 of SEQ ID NO:13). In some forms, the sequence of signs chains can comprise the amino acid side chain sequence of the peptide QAARK (amino acids 2 to 6 of SEQ ID NO:13). In some forms, the sequence of signs chains can comprise the amino acid side chain sequence of the peptide KQAARK (SEQ ID NO:13). In some forms, the sequence of signs chains can comprise the amino acid side chain sequence of the peptide AARKSTGG (amino acids 3 to 10 of SEQ ID NO:14). In some forms, the sequence of signs chains can comprise the amino acid side chain sequence of the peptide QAARKSTGG (amino acids 2 to 10 of SEQ ID NO:14). In some forms, the sequence of signs chains can comprise the amino acid side chain sequence of the peptide KQAARKSTGG (SEQ ID NO:14).

In some forms, the sequence of signs chains can comprise the amino acid side chain sequence of the peptide SARK (amino acids 3 to 6 of SEQ ID NO:15). In some forms, the sequence of signs chains can comprise the amino acid side chain sequence of the peptide QSARK (amino acids 2 to 6 of SEQ ID NO:15). In some forms, the sequence of signs chains can comprise the amino acid side chain sequence of the peptide KQSARK (SEQ ID NO:15). In some forms, the sequence of signs chains can comprise the amino acid side chain sequence of the peptide SARKSTGG (amino acids 3 to 10 of SEQ ID NO:16). In some forms, the sequence of signs chains can comprise the amino acid side chain sequence of the peptide QSARKSTGG (amino acids 2 to 10 of SEQ ID NO:16). In some forms, the sequence of signs chains can comprise the amino acid side chain sequence of the peptide KQSARKSTGG (SEQ ID NO:16).

In some forms, the sequence of signs chains can comprise the amino acid side chain sequence of the peptide (A/L/W)RK. In some forms, the sequence of signs chains can comprise the amino acid side chain sequence of the peptide T(A/L/W)RK (amino acids 3 to 6 of SEQ ID NO:9). In some forms, the sequence of signs chains can comprise the amino acid side chain sequence of the peptide QT(A/L/W)RK (amino acids 2 to 6 of SEQ ID NO:9). In some forms, the sequence of signs chains can comprise the amino acid side chain sequence of the peptide KQT(A/L/W)RK (SEQ ID NO:9). In some forms, the sequence of signs chains can comprise the amino acid side chain sequence of the peptide (A/L/W)RKSTGG (amino acids 4 to 10 of SEQ ID NO:10). In some forms, the sequence of signs chains can comprise the amino acid side chain sequence of the peptide T(A/L/W)RKSTGG (amino acids 3 to 10 of SEQ ID NO:10). In some forms, the sequence of signs chains can comprise the amino acid side chain sequence of the peptide QT(A/L/W)RKSTGG (amino acids 2 to 10 of SEQ ID NO:10). In some forms, the sequence of signs chains can comprise the amino acid side chain sequence of the peptide KQT(A/L/W)RKSTGG (SEQ ID NO:10).

In some forms, the sequence of signs chains can comprise the amino acid side chain sequence of the peptide LRK. In some forms, the sequence of signs chains can comprise the amino acid side chain sequence of the peptide LRK (amino acids 3 to 6 of SEQ ID NO:19). In some forms, the sequence of signs chains can comprise the amino acid side chain sequence of the peptide QTLRK (amino acids 2 to 6 of SEQ ID NO:19). In some forms, the sequence of signs chains can comprise the amino acid side chain sequence of the peptide KQTLRK (SEQ ID NO:19). In some forms, the sequence of signs chains can comprise the amino acid side chain sequence of the peptide LRKSTGG (amino acids 4 to 10 of SEQ ID NO:20). In some forms, the sequence of signs chains can comprise the amino acid side chain sequence of the peptide TLRKSTGG (amino acids 3 to 10 of SEQ ID NO:20). In some forms, the sequence of signs chains can comprise the amino acid side chain sequence of the peptide QTLRKSTGG (amino acids 2 to 10 of SEQ ID NO:20). In some forms, the sequence of signs chains can comprise the amino acid side chain sequence of the peptide KQTLRKSTGG (SEQ ID NO:20).

In some forms, the sequence of signs chains can comprise the amino acid side chain sequence of the peptide WRK. In some forms, the sequence of signs chains can comprise the amino acid side chain sequence of the peptide TWRK (amino acids 3 to 6 of SEQ ID NO:17). In some forms, the sequence of signs chains can comprise the amino acid side chain sequence of the peptide QTWRK (amino acids 2 to 6 of SEQ ID NO:17). In some forms, the sequence of signs chains can comprise the amino acid side chain sequence of the peptide KQTWRK (SEQ ID NO:17). In some forms, the sequence of signs chains can comprise the amino acid side chain sequence of the peptide WRKSTGG (amino acids 4 to 10 of SEQ ID NO:18). In some forms, the sequence of signs chains can comprise the amino acid side chain sequence of the peptide TWRKSTGG (amino acids 3 to 10 of SEQ ID NO:18). In some forms, the sequence of signs chains can comprise the amino acid side chain sequence of the peptide QTWRKSTGG (amino acids 2 to 10 of SEQ ID NO:18). In some forms, the sequence of signs chains can comprise the amino acid side chain sequence of the peptide KQTWRKSTGG (SEQ ID NO:18).

In some forms, the sequence of signs chains can comprise the amino acid side chain sequence of the peptide (T/A/S)(A/L/W)RK (amino acids 3 to 6 of SEQ ID NO:11). In some forms, the sequence of signs chains can comprise the amino acid side chain sequence of the peptide Q(T/A/S)(A/L/W)RK (amino acids 2 to 6 of SEQ ID NO:11). In some forms, the sequence of signs chains can comprise the amino acid side chain sequence of the peptide KQ(T/A/S)(A/L/W)RK (SEQ ID NO:11). In some forms, the sequence of signs chains can comprise the amino acid side chain sequence of the peptide (T/A/S)(A/L/W)RKSTGG (amino acids 3 to 10 of SEQ ID NO:12). In some forms, the sequence of signs chains can comprise the amino acid side chain sequence of the peptide Q(T/A/S)(A/L/W)RKSTGG (amino acids 2 to 10 of SEQ ID NO:12). In some forms, the sequence of signs chains can comprise the amino acid side chain sequence of the peptide KQ(T/A/S)(A/L/W)RKSTGG (SEQ ID NO:12).

In some forms, the sequence of signs chains can consist of the amino acid side chain sequence of the peptide ARK. In some forms, the sequence of signs chains can consist of the amino acid side chain sequence of the peptide TARK (amino acids 2 to 5 of SEQ ID NO:4). In some forms, the sequence of signs chains can consist of the amino acid side chain sequence of the peptide QTARK (SEQ ID NO:4). In some forms, the sequence of signs chains can consist of the amino acid side chain sequence of the peptide KQTARK (SEQ ID NO:5). In some forms, the sequence of signs chains can consist of the amino acid side chain sequence of the peptide ARKSTGG (amino acids 4 to 10 of SEQ ID NO:6). In some forms, the sequence of signs chains can consist of the amino acid side chain sequence of the peptide TARKSTGG (amino acids 3 to 10 of SEQ ID NO:6). In some forms, the sequence of signs chains can consist of the amino acid side chain sequence of the peptide QTARKSTGG (amino acids 2 to 10 of SEQ ID NO:6). In some forms, the sequence of signs chains can consist of the amino acid side chain sequence of the peptide KQTARKSTGG (SEQ ID NO:6).

In some forms, the sequence of signs chains can consist of the amino acid side chain sequence of the peptide (T/A/S)ARK (amino acids 3 to 6 of SEQ ID NO:7). In some forms, the sequence of signs chains can consist of the amino acid side chain sequence of the peptide Q(T/A/S)ARK (amino acids 2 to 6 of SEQ ID NO:7). In some forms, the sequence of signs chains can consist of the amino acid side chain sequence of the peptide KQ(T/A/S)ARK (SEQ ID NO:7). In some forms, the sequence of signs chains can consist of the amino acid side chain sequence of the peptide (T/A/S)ARKSTGG (amino acids 3 to 10 of SEQ ID NO:8). In some forms, the sequence of signs chains can consist of the amino acid side chain sequence of the peptide Q(T/A/S)ARKSTGG (amino acids 2 to 10 of SEQ ID NO:8). In some forms, the sequence of signs chains can consist of the amino acid side chain sequence of the peptide KQ(T/A/S)ARKSTGG (SEQ ID NO:8).

In some forms, the sequence of signs chains can consist of the amino acid side chain sequence of the peptide AARK (amino acids 3 to 6 of SEQ ID NO:13). In some forms, the sequence of signs chains can consist of the amino acid side chain sequence of the peptide QAARK (amino acids 2 to 6 of SEQ ID NO:13). In some forms, the sequence of signs chains can consist of the amino acid side chain sequence of the peptide KQAARK (SEQ ID NO:13). In some forms, the sequence of signs chains can consist of the amino acid side chain sequence of the peptide AARKSTGG (amino acids 3 to 10 of SEQ ID NO:14). In some forms, the sequence of signs chains can consist of the amino acid side chain sequence of the peptide QAARKSTGG (amino acids 2 to 10 of SEQ ID NO:14). In some forms, the sequence of signs chains can consist of the amino acid side chain sequence of the peptide KQAARKSTGG (SEQ ID NO:14).

In some forms, the sequence of signs chains can consist of the amino acid side chain sequence of the peptide SARK (amino acids 3 to 6 of SEQ ID NO:15). In some forms, the sequence of signs chains can consist of the amino acid side chain sequence of the peptide QSARK (amino acids 2 to 6 of SEQ ID NO:15). In some forms, the sequence of signs chains can consist of the amino acid side chain sequence of the peptide KQSARK (SEQ ID NO:15). In some forms, the sequence of signs chains can consist of the amino acid side chain sequence of the peptide SARKSTGG (amino acids 3 to 10 of SEQ ID NO:16). In some forms, the sequence of signs chains can consist of the amino acid side chain sequence of the peptide QSARKSTGG (amino acids 2 to 10 of SEQ ID NO:16). In some forms, the sequence of signs chains can consist of the amino acid side chain sequence of the peptide KQSARKSTGG (SEQ ID NO:16).

In some forms, the sequence of signs chains can consist of the amino acid side chain sequence of the peptide (A/L/W)RK. In some forms, the sequence of signs chains can consist of the amino acid side chain sequence of the peptide T(A/L/W)RK (amino acids 3 to 6 of SEQ ID NO:9). In some forms, the sequence of signs chains can consist of the amino acid side chain sequence of the peptide QT(A/L/W)RK (amino acids 2 to 6 of SEQ ID NO:9). In some forms, the sequence of signs chains can consist of the amino acid side chain sequence of the peptide KQT(A/L/W)RK (SEQ ID NO:9). In some forms, the sequence of signs chains can consist of the amino acid side chain sequence of the peptide (A/L/W)RKSTGG (amino acids 4 to 10 of SEQ ID NO:10). In some forms, the sequence of signs chains can consist of the amino acid side chain sequence of the peptide T(A/L/W)RKSTGG (amino acids 3 to 10 of SEQ ID NO:10). In some forms, the sequence of signs chains can consist of the amino acid side chain sequence of the peptide QT(A/L/W)RKSTGG (amino acids 2 to 10 of SEQ ID NO:10). In some forms, the sequence of signs chains can consist of the amino acid side chain sequence of the peptide KQT(A/L/W)RKSTGG (SEQ ID NO:10).

In some forms, the sequence of signs chains can consist of the amino acid side chain sequence of the peptide LRK. In some forms, the sequence of signs chains can consist of the amino acid side chain sequence of the peptide LRK (amino acids 3 to 6 of SEQ ID NO:19). In some forms, the sequence of signs chains can consist of the amino acid side chain sequence of the peptide QTLRK (amino acids 2 to 6 of SEQ ID NO:19). In some forms, the sequence of signs chains can consist of the amino acid side chain sequence of the peptide KQTLRK (SEQ ID NO:19). In some forms, the sequence of signs chains can consist of the amino acid side chain sequence of the peptide LRKSTGG (amino acids 4 to 10 of SEQ ID NO:20). In some forms, the sequence of signs chains can consist of the amino acid side chain sequence of the peptide TLRKSTGG (amino acids 3 to 10 of SEQ ID NO:20). In some forms, the sequence of signs chains can consist of the amino acid side chain sequence of the peptide QTLRKSTGG (amino acids 2 to 10 of SEQ ID NO:20). In some forms, the sequence of signs chains can consist of the amino acid side chain sequence of the peptide KQTLRKSTGG (SEQ ID NO:20).

In some forms, the sequence of signs chains can consist of the amino acid side chain sequence of the peptide WRK. In some forms, the sequence of signs chains can consist of the amino acid side chain sequence of the peptide TWRK (amino acids 3 to 6 of SEQ ID NO:17). In some forms, the sequence of signs chains can consist of the amino acid side chain sequence of the peptide QTWRK (amino acids 2 to 6 of SEQ ID NO:17). In some forms, the sequence of signs chains can consist of the amino acid side chain sequence of the peptide KQTWRK (SEQ ID NO:17). In some forms, the sequence of signs chains can consist of the amino acid side chain sequence of the peptide WRKSTGG (amino acids 4 to 10 of SEQ ID NO:18). In some forms, the sequence of signs chains can consist of the amino acid side chain sequence of the peptide TWRKSTGG (amino acids 3 to 10 of SEQ ID NO:18). In some forms, the sequence of signs chains can consist of the amino acid side chain sequence of the peptide QTWRKSTGG (amino acids 2 to 10 of SEQ ID NO:18). In some forms, the sequence of signs chains can consist of the amino acid side chain sequence of the peptide KQTWRKSTGG (SEQ ID NO:18).

In some forms, the sequence of signs chains can consist of the amino acid side chain sequence of the peptide (T/A/S)(A/L/W)RK (amino acids 3 to 6 of SEQ ID NO:11). In some forms, the sequence of signs chains can consist of the amino acid side chain sequence of the peptide Q(T/A/S)(A/L/W)RK (amino acids 2 to 6 of SEQ ID NO:11). In some forms, the sequence of signs chains can consist of the amino acid side chain sequence of the peptide KQ(T/A/S)(A/L/W)RK (SEQ ID NO:11). In some forms, the sequence of signs chains can consist of the amino acid side chain sequence of the peptide (T/A/S)(A/L/W)RKSTGG (amino acids 3 to 10 of SEQ ID NO:12). In some forms, the sequence of signs chains can consist of the amino acid side chain sequence of the peptide Q(T/A/S)(A/L/W)RKSTGG (amino acids 2 to 10 of SEQ ID NO:12). In some forms, the sequence of signs chains can consist of the amino acid side chain sequence of the peptide KQ(T/A/S)(A/L/W)RKSTGG (SEQ ID NO:12).

Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula (I) to base used are chosen to provide the ratio desired for any particular salts. For preparing, for example, the ammonium salts of the free acid starting material, the starting material can be treated with approximately one equivalent of pharmaceutically acceptable base to yield a neutral salt.

III. Pharmaceutical Compositions

The disclosed compounds can be used to treat subjects in need thereof. For this purpose, it is useful to have the compounds formulated in a pharmaceutical composition. Such pharmaceutical compositions comprise one or more of the disclosed linear or cyclic peptide compounds and a pharmaceutically acceptable excipient.

Pharmaceutically acceptable excipients, as used herein, include any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21.sup.st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some forms, the pharmaceutically acceptable excipient is at least 95%, 96%, 97%, 98%, 99%, or 100% pure. In some forms, the excipient is approved for use in humans and for veterinary use. In some forms, the excipient is approved by the United States Food and Drug Administration. In some forms, the excipient is of pharmaceutical grade. In some forms, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and Veegum [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain forms, the preservative is an anti-oxidant. In other forms, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can include adjuvants such as wetting agents, emulsifying and suspending agents, sweetening, flavoring, and perfuming agents. In certain forms for parenteral administration, the conjugates of the invention are mixed with solubilizing agents such as CREMOPHOR, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients, such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may contain buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may contain, as is normal practice, additional substances other than inert diluents, e.g., tableting lubricants and other tableting aids such a magnesium stearate and microcrystalline cellulose. In the case of capsules, tablets and pills, the dosage forms may contain buffering agents. They may optionally contain opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a conjugate of this invention may include ointments, pastes, creams, lotions, gels, powders, solutions, sprays, inhalants and/or patches. Generally, the active component is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

The compounds, proteins, or peptides described herein (e.g., amino acids, and linear or cyclic peptides and proteins) may exist in particular geometric or stereoisomeric forms. They may have one or more chiral centers and thus exist as one or more stereoisomers. Such stereoisomers as encompassed by the present disclosure can exist as a single enantiomer, a mixture of diastereomers or a racemic mixture. As used herein, the term "stereoisomers" refers to compounds made up of the same atoms having the same bond order but having different three-dimensional arrangements of atoms which are not interchangeable. The three-dimensional structures are called configurations. In the present disclosure the chemical structures shown may include one or more wavy bonds therein which represent all enantiomers possible at each of the chiral centers depicted. The wavy bonds shown in chemical structures, as used herein, are intended to depict either of the chiral configurations typically depicted by hashed or wedged bonds and in peptides containing more than one wavy bond any combination of stereochemistry possible is disclosed. As used herein, the term "enantiomers" refers to two stereoisomers which are non-superimposable mirror images of one another. As used herein, the term "optical isomer" is equivalent to the term "enantiomer." As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of pairs of enantiomers is well known to one of ordinary skill in the art using standard techniques (see e.g. Jacques, J. et al., "Enantiomers, Racemates, and Resolutions," John Wiley and Sons, Inc. 1981). The present invention contemplates all such compounds, including cis- and trans-isomers, R- and S-enantiomers, diastereomers, (D)- and (L)-isomers, the racemic mixtures thereof, and other mixtures thereof, as falling within the scope of the invention.

It will be appreciated that the compounds described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substituents are illustrated by the specific forms shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

Also disclosed are compositions comprising a protein or peptide and a cargo composition, wherein the protein or peptide comprises a peptide according to Formula I, II, III, IV, V, or other formula, and a homing peptide, wherein the peptide according to Formula I, II, III, IV, V, or other formula and the cargo composition are covalently coupled or non-covalently associated with each other. In these compositions, the composition can comprise one or more cargo compositions and/or one or more homing peptides, wherein the protein or peptide and at least one of the cargo compositions are not covalently coupled or non-covalently associated with each other, wherein the protein or peptide and at least one of the homing peptides are covalently coupled or non-covalently associated with each other.

As used herein, reference to components as being "not covalently coupled" means that the components are not connected via covalent bonds. That is, there is no continuous chain of covalent bonds between, for example, the peptide according to Formula I, II, III, IV, V, or other formula, and the co-composition. Conversely, reference to components as being "covalently coupled" means that the components are connected via covalent bonds. That is, there is a continuous chain of covalent bonds between, for example, the peptide according to Formula I, II, III, IV, V, or other formula and the cargo composition. Components can be covalently coupled either directly or indirectly. Direct covalent coupling refers to the presence of a covalent bond between atoms of each of the components. Indirect covalent coupling refers to the absence of a covalent bond between atoms of each of the components. That is, some other atom or atoms not belonging to either of the coupled components intervenes between atoms of the components. Both direct and indirect covalent coupling involve a continuous chain of covalent bonds.

Non-covalent association refers to association of components via non-covalent bonds and interactions. A non-covalent association can be either direct or indirect. A direct non-covalent association refers to a non-covalent bond involving atoms that are each respectively connected via a chain of covalent bonds to the components. Thus, in a direct non-covalent association, there is no other molecule intervening between the associated components. An indirect non-covalent association refers to any chain of molecules and bonds linking the components where the components are not covalently coupled (that is, there is a least one separate molecule other than the components intervening between the components via non-covalent bonds).

Non-covalent association refers to association of components via non-covalent bonds and interactions. A non-covalent association can be either direct or indirect. A direct non-covalent association refers to a non-covalent bond involving atoms that are each respectively connected via a chain of covalent bonds to the components. Thus, in a direct non-covalent association, there is no other molecule intervening between the associated components. An indirect non-covalent association refers to any chain of molecules and bonds linking the components where the components are not covalently coupled (that is, there is a least one separate molecule other than the components intervening between the components via non-covalent bonds).

The amino acid sequence can be associated with one or more accessory molecules. For example, an accessory molecule can be a part of an amino acid sequence, protein, peptide, conjugate, or composition that comprises the amino acid sequence. As another example, the accessory molecule can be covalently coupled or non-covalently associated with the amino acid sequence or an amino acid sequence, protein, peptide, conjugate, or composition that comprises the amino acid sequence. For example, the amino acid sequences can comprise an iRGD peptide, a LyP-1 peptide, a RGR peptide, a HER2 binding peptide, a CREKA peptide, a NGR peptide, iNGR, an RGD peptide, or a combination. The amino acid sequence can comprise a CREKA peptide. The protein or peptide can be associated with one or more accessory molecules. For example, an accessory molecule can be a part of a protein, peptide, conjugate, or composition that comprises the peptide. As another example, the accessory molecule can be covalently coupled or non-covalently associated with the peptide or a protein, peptide, conjugate, or composition that comprises the peptide. For example, an accessory molecule can be a part of a protein, conjugate, or composition that comprises the protein.

The amino acid sequence can be selected for internalization into a cell. The amino acid sequence can be selected for tissue penetration. The amino acid sequence can be selected for internalization into a cell and tissue penetration. The protein or peptide can be selected for internalization into a cell. The protein or peptide can be selected for tissue penetration. The protein or peptide can be selected for internalization into a cell and tissue penetration. The conjugate can be selected for internalization into a cell. The conjugate can be selected for tissue penetration. The conjugate can be selected for internalization into a cell and tissue penetration. The composition can be selected for internalization into a cell. The composition can be selected for tissue penetration. The composition can be selected for internalization into a cell and tissue penetration.

The disclosed peptides, conjugates, compositions, amino acid sequences, proteins co-compositions, cargo compositions, or a combination can selectively home to brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, tumor cells, tumors, tumor blood vessels, and/or tumor vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

In some forms, the compound can selectively home to a tumor. In some forms, the compound can selectively home to tumor vasculature. In some forms, the compound and the co-composition are not bound to each other. In some forms, the co-composition and/or cargo composition can comprise a therapeutic agent. In some forms, the co-composition and/or cargo composition can comprise a detection agent. In some forms, the co-composition and/or cargo composition can comprise a carrier, vehicle, or both. In some forms, the co-composition and/or cargo composition can comprise a therapeutic protein, a therapeutic compound, a therapeutic composition, a cancer chemotherapeutic agent, a toxin, a cytotoxic agent, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, an anti-angiogenic agent, or a combination.

IV. Methods of Using

A. Conditions

Provided are methods of treating a disease, disorder, or condition by administering to a subject diagnosed with or having susceptibility to the disease, disorder, or condition, a therapeutically effective amount of a peptide inhibitor. Peptide inhibitor compounds, as described herein, may be useful wherever such secondary structural motifs are advantageous, for example, as a therapeutic agent or a research tool. In some forms, the compounds may function as inhibitors of π-π-π stacking interactions. In certain forms, the compounds may function as inhibitors of π-π-π stacking interactions in YEATS domains. Generally speaking, the compounds may be modulators of protein-protein, protein-ligand, or protein-receptor binding interactions. In some forms, these compounds are useful in the treatment of any conditions characterized by chromatin modification or remodeling. In some forms, these compounds are useful in the treatment of acute leukemia. In certain forms, these compounds are useful in the treatment of mixed lineage leukemia.

In certain forms, peptide inhibitor compounds can be used to alter one or more characteristics of the target. In certain forms, the characteristics of the target are altered in such a way that this alteration affects cell fate and/or cell behavior. In certain forms, changes in cell fate or cell behavior as a result of changes in one or more characteristics of the target affect the disease state of a subject, such as a mammal, for example, a human. In certain forms, peptide inhibitor compounds can be used to treat disease. In certain forms peptide inhibitor compounds can be used to probe or elucidate biological pathways in research. The probing of a biological pathway can be performed both in vitro such as in cell or tissue culture, or in vivo, such as in an animal, e.g., humans, mice, rats, hamsters, fish, or primates.

B. Dosage

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The exact amount required will vary from subject to subject, depending on the species, age, and general condition of the subject, the particular protein, its mode of administration, its mode of activity, and the like. The proteins of the invention are preferably formulated in dosage unit form for ease of administration and uniformity of dosage. It will be understood, however, that the total daily usage of the proteins and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific protein employed; the specific composition employed; the age, body weight, general health, sex and diet of the patient; the time of administration, route of administration, and rate of excretion of the specific compound employed; the duration of the treatment; drugs used in combination or coincidental with the specific protein employed; and like factors well known in the medical arts.

In certain forms, the peptide inhibitor compounds of the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain forms, the desired dosage may be delivered using multiple administrations (e.g., two, three, four, five, six, seven, eight, nine, ten, eleven, twelve, thirteen, fourteen, or more administrations).

C. Routes of Administration

The pharmaceutical compositions of the present invention may be administered by any route. In some forms, the pharmaceutical compositions of the present invention are administered variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of the pharmaceutical composition by any appropriate route taking into consideration likely advances in the sciences of drug delivery.

The disclosed peptides and pharmaceutical compositions may be administered to animals, preferably mammals (e.g., domesticated animals, cats, dogs, mice, rats), and more preferably humans.

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain forms for parenteral administration, the proteins of the invention are mixed with solubilizing agents such Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

It will also be appreciated that the proteins and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a compound may be administered concurrently with another anticancer agent), or they may achieve different effects (e.g., control of any adverse effects).

In some forms, compositions can be administered in combination with surgery to remove a tumor. Because complete removal of a tumor with minimal or no damage to the rest of a patient's body is typically the goal of cancer treatment, surgery is often performed to physically remove part or all of a tumor. If surgery is unable to completely remove a tumor, additional therapies (e.g., chemotherapy, radiation therapy, hormonal therapy, immunotherapy, complementary or alternative therapy) may be employed.

In some forms, compositions can be administered in combination with radiation therapy. Radiation therapy (also known as radiotherapy, X-ray therapy, or irradiation) is the use of ionizing radiation to kill cancer cells and shrink tumors. Radiation therapy may be used to treat almost any type of solid tumor, including cancers of the brain, breast, cervix, larynx, lung, pancreas, prostate, skin, stomach, uterus, or soft tissue sarcomas. Radiation can be used to treat leukemia and lymphoma. Radiation therapy can be administered externally via external beam radiotherapy (EBRT) or internally via brachytherapy. Typically, the effects of radiation therapy are localized and confined to the region being treated. Radiation therapy injures or destroys tumor cells in an area being treated (e.g., a target organ, tissue, and/or cell) by damaging their genetic material, preventing tumor cells from growing and dividing. In general, radiation therapy attempts to damage as many tumor cells as possible while limiting harm to nearby healthy tissue. Hence, it is often administered in multiple doses, allowing healthy tissue to recover between fractions.

In some forms, compositions can be administered in combination with immunotherapy. Immunotherapy is the use of immune mechanisms against tumors which can be used in various forms of cancer, such as breast cancer (e.g., trastuzumab/HERCEPTIN®), leukemia (e.g., gemtuzumab ozogamicin/MYLOTARG®), and non-Hodgkin's lymphoma (e.g., rituximab/RITUXAN®). In some forms, immunotherapy agents are monoclonal antibodies directed against proteins that are characteristic to the cells of the cancer in question. In some forms, immunotherapy agents are cytokines that modulate the immune system's response. In some forms, immunotherapy agents may be vaccines.

EXAMPLES

Materials and Methods
Reagents and Instruments
Unless otherwise noted, all the chemical reagents were purchased from Sigma-Aldrich. All Fmoc- or Cbz-protected amino acids, resin for solid-phase peptide synthesis, and coupling reagents were purchased from GL Biochem. In-solution reactions were monitored by TLC silica gel 60 F254 from Merck. Flash column chromatography was performed with silica gel purchased from Grace.

$^1$H and $^{13}$C NMR spectra were recorded on Bruker UltraShield 400 or 600 MHz spectrometers and were calibrated using residual undeuterated solvent as an internal reference. Chemical shifts were reported in ppm, and coupling constant J was reported in Hz. Peptides were analyzed by LC-MS with an Agilent 1260 Infinity HPLC system connected to a Thermo Finnigan LCQ DecaXP MS detector. Peptides were purified on a preparative HPLC system with Waters 2535 Quaternary Gradient Module, Waters 515 HPLC pump, Waters SFO System Fluidics Organizer, and Waters 2767 Sample Manager. Photo-cross-linking was performed with an ENF-260C/FE hand-hang UV lamp (Spectroline). In-gel fluorescence scanning was performed using a Typhoon 9410 variable mode imager from GE Healthcare Life Sciences (excitation 532 nm, emission 580 nm). Images of Coomassie blue staining were acquired by MyECL Imager from Thermo Scientific. All images were processed by ImageJ software (National Institutes of Health), and contrast was adjusted appropriately. ITC experiments were performed with a MicroCal iTC200 titration calorimeter (MicroCal). $IC_{50}$ and dissociation constants were fit with Origin 7.0 software package (OriginLab).

Protein Expression and Purification
Plasmids of His-AF9 (1-138), His-SUMO-ENL (1-138), His-SUMO-YEATS2 (201-332), His-Gas41 (15-159) and all the proteins were expressed and purified with the methods described in the following references: Y. Li, et al., AF9 YEATS domain links histone acetylation to DOT1L-mediated H3K79 methylation, Cell, 2014, 159(3), 558-571; Y. Li, et al., Molecular Coupling of Histone Crotonylation and Active Transcription by AF9 YEATS Domain, Molecular Cell, 2016, 62(2), 181-193; and YEATS2 is a selective histone crotonylation reader, Cell Research (2016) 26:629-632. The proteins were expressed in *E. coli* Rosetta cells. To induce the expression, IPTG was added to a final concentration of 0.4 mM when O.D. 600 was 0.6, and the culture was grown at 16° C. for another 16 h. Cells were harvested and then resuspended in lysis buffer (50 mM Tris-HCl, pH 7.5, 500 mM NaCl, 1 mM TCEP, 20 mM imidazole with freshly added 1 mM PMSF and Roche EDTA-free protease inhibitors). Following sonication and centrifugation, the supernatant was loaded onto a Ni-column pre-equilibrated with lysis buffer. The column was washed with 5 column volumes of wash buffer (50 mM Tris-HCl, pH 7.5, 500 mM NaCl, 20 mM imidazole) and then target proteins were eluted with elution buffer (50 mM Tris-HCl, pH 7.5, 500 mM NaCl, 250 mM imidazole). The proteins were further loaded onto a Highload 26/60 Superdex-200 gel-filtration column (GE Healthcare Life Sciences) and were eluted with elution buffer (500 mM NaCl, 50 mM HEPES, 1 mM TCEP, pH 7.5). After concentration, the target proteins were frozen and then stored at −80° C. for later use.

Synthesis of Fmoc-Lys(2-furancarbonyl)-OH 2-furancarboxylic acid (1.5 equivalent) and N-hydroxysuccinimide (NHS, 1.4 equivalent) were dissolved in dry tetrahydrofuran (THF). Dicyclohexylcarbodiimide (DCC, 1.4 equivalent) in dry THF was added into the above solution and stirred at room temperature overnight. The reaction mixture was filtered and to the filtrate was added Fmoc-Lys-OH.HCl (1 equivalent) together with N,N-Diisopropylethylamine (DIEA, 3 equivalent). The resulting reaction mixture was allowed to stir at room temperature another 4-6 hours. The pH of the mixture was adjusted to 7 with 1 M HCl. The solvent was in vacuo. The residue was extracted with dichloromethane and 1 M HCl. The organic layer was washed with brine and dried over $Na_2SO_4$. After removal of solvent, the crude product was purified by silica gel column chromatography to give a white solid (74% yield). $^1$H-NMR (DMSO-$d_6$, 400 MHz) δ 8.37 (t, 1H, J=5.41), 7.89 (d, 2H, J=7.48), 7.79 (s, 1H), 7.72 (d, 2H, J=7.44), 7.65 (d, 1H, J=7.90), 7.41 (t, 2H, J=7.39), 7.32 (t, 2H, J=7.42), 7.06 (d, 1H, J=3.29), 6.60 (d, 1H, J=1.43), 4.29-4.20 (m, 3H), 3.95-3.89 (m, 1H), 3.20 (q, 2H, J=6.29), 1.73-1.58 (m, 2H), 1.52-1.42 (m, 2H), 1.38-1.32 (m, 2H). $^{13}$C-NMR (DMSO-$d_6$, 100 MHz) δ 174.07, 157.75, 156.23, 148.14, 144.80, 143.84, 140.77, 127.70, 127.12, 125.35, 120.17, 113.11, 111.82, 65.65, 53.85, 46.70, 38.26, 30.49, 28.84, 23.18. HRMS (ESI) calculated m/z for $[M+Na]^+$: 485.1683, found 485.1681.

Peptide Synthesis and Purification

Peptides were synthesized on a Rink-Amide MBHA resin followed by a standard Fmoc-based solid-phase peptide synthesis protocol. After all amino acids were coupled, protecting groups and cleavage of peptides from the resin were done by incubating the resin with a cleavage cocktail containing 95% trifluoroacetic acid, 2.5% triisopropylsilane, 1.5% $H_2O$ and, 1% thioanisole for 2 h. Peptides were purified by preparative HPLC with an XBridge Prep OBDTM C18 column (30 mm×250 mm, 10 μm, Waters). Mobile phase used were water with 0.1% trifluoroacetic acid (buffer A) and 90% acetonitrile in water with 0.1% trifluoroacetic acid (buffer B). The purity (>95%) and identity of peptides were confirmed by LC-MS. The inhibitory activities of the inhibitors were determined by a photo-cross-linking-based competition assay.

Photo Cross-Linking

The probe 4.1 or 4.2 (2 μM) with indicated concentrations of different inhibitors was incubated with YEATS domain proteins (5 or 20 ng/μL) in binding buffer (50 mM HEPES, 150 mM NaCl, 2 mM MgCl2, 0.1% Tween-20, 20% glycerol, pH 7.5, with or without 50 ng/μL BSA) for 10 min at 4° C. Then, the samples were irradiated at 365 nm using a UV lamp for 20 min in a 96-well plate on ice.

Cu(I)-catalyzed azide-alkyne Cycloaddition/"Click" Chemistry

To the prepared photo-cross-linking samples, 100 μM Rho-$N_3$ (10 mM stock in DMSO) was added, followed by 1 mM TCEP (freshly prepared 50 mM stock in $H_2O$), 100 μM TBTA (10 mM stock in DMSO), and finally the reactions were initiated by the addition of 1 mM $CuSO_4$ (freshly prepared 50 mM stock in $H_2O$). The reactions were incubated for 1 h at r.t . . . . The reactions were quenched by adding 5 volumes of ice-cold acetone and placed at −20° C. overnight to precipitate proteins.

In-Gel Fluorescence Scanning

After protein precipitation, samples were centrifuged at 6000×g for 5 min at 4° C. The supernatant was discarded and the pellet was washed with ice-cooled methanol twice and air-dried for 10 min. The proteins were resuspended in 1×LDS sample loading buffer (Invitrogen) with 50 mM DTT, and heated at 80° C. for 8 min. Samples were then resolved by SDS-PAGE. The labeled proteins were visualized by scanning the gel on a Typhoon 9410 variable mode imager (excitation 532 nm, emission filter 580 nm).

Example 1. Targeting π-π-π Stacking for YEATS Inhibition

Bromodomain (BrD), which recognizes lysine acetylation (Kac, as shown below), is one of the epigenetic readers that have been extensively explored for inhibitor development. While varied in sequences, the BrDs accommodate acetyllysine with hydrophobic pockets sharing a similar structure. The acetyl group is mainly anchored by forming a hydrogen bond with a conserved asparagine in the binding pocket. A major class of reported BrD inhibitors are the acetyllysine mimics, which retain the signature hydrogen bond when binding to the BrDs. The inhibition of BrDs has been demonstrated as an effective way for the treatment of cancer, viral infection, inflammation, as well as neurological diseases.

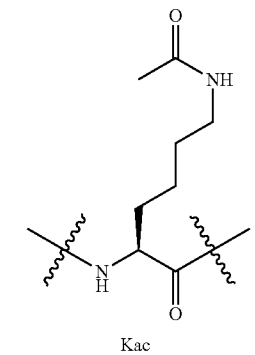 [SMILES: *N[C@@H](CCCCNC(C)=O)C(*)=O]

Kac

Besides the BrDs, the YEATS domain was identified as a novel reader of Kac. The human genome encodes 4 YEATS domain-containing proteins, which are AF9, ENL, YEATS2, and Gas41. Unlike the BrDs with end-closed binding cavities, the YEATS domains coordinate the acetyllysine with an end-open aromatic 'sandwich' cage shaped by two conserved aromatic residues. Notably, the tunnel-like feature of the end-open cage also enables the YEATS domains to recognize the histone lysine crotonylation (Kcr, as shown below) marks, whose acyl chain is two carbons longer than Kac.

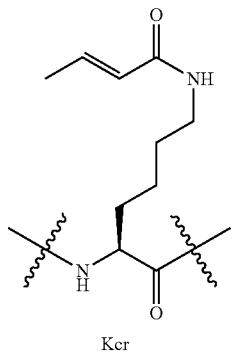 [SMILES: *N[C@@H](CCCCNC(=O)/C=C/C)C(*)=O]

Kcr

Moreover, the conjugated 'O=C—C=C' moiety of the crotonyl group forms a unique π-π-π stack with the two conserved aromatic residues, which significantly enhances the binding affinity, suggesting a preference of a YEATS domain toward Kcr over Kac at the molecular level. Given the fact that BrD-containing proteins and YEATS domain-containing proteins are presented in different nuclear complexes, and the low affinity or incapability of the BrDs to interact with Kcr, the YEATS-dependent recognitions toward histone Kac and Kcr marks are likely to result in distinct biological functions compared to BrD-Kac recognition. Recently, the AF9 YEATS domain was found to mediate active transcription through reading the histone Kac and Kcr marks. The YEATS-dependent association of ENL with acetylated histone H3 was reported to be essential for oncogenic gene expression in aggressive leukemia. Despite these discoveries, we have limited knowledge on the functional outcomes of YEATS-Kac/Kcr interactions in epigenetic regulation. The development of YEATS domain inhibitors should provide useful tools to fill such knowledge gap, and offer potential therapeutic agents targeting the YEATS domain.

Figure 23:
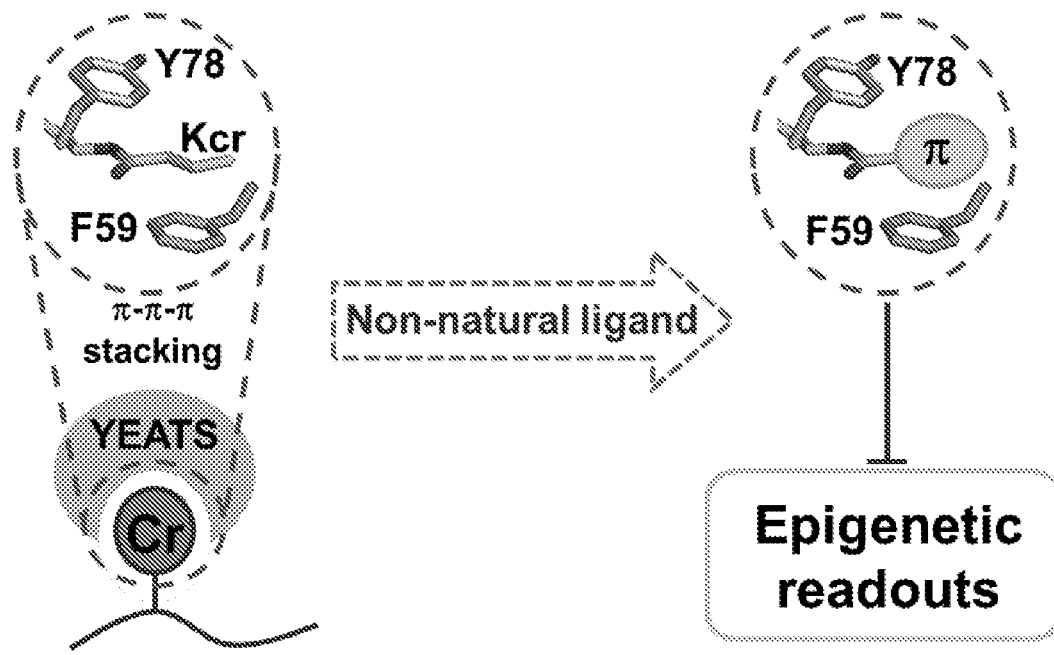
FIG. 23 is a schematic illustrating the strategy for inhibitor design.

In the YEATS-Kcr complex, the conjugated crotonyl group inserts into the aromatic 'sandwich' cage, forming a π-π-π stack with the two conserved aromatic residues (F59 and Y78 for AF9, FIG. 23). Although the YEATS domains recognize both Kac and Kcr using a same pocket, the binding affinity to Kcr is normally 2-5 folds higher than to Kac, suggesting an expanded π-system is favored for the recognition. We therefore reasoned that targeting the π-π-π stacking by replacing the native crotonyl group with non-natural conjugated π-system-containing functional groups should be a direct strategy for the inhibitor design (FIG. 23). We first focused on the histone H3K9 sequence and AF9 YEATS domain for inhibitor development, as the AF9-H3K9cr pair exhibited the highest binding affinity among all the reported YEATS-Kcr interactions. To search for the π-systems that block the YEATS-Kcr interaction, 16 groups were initially selected and incorporated at the K9 position (sequence derived from histone H3 K4-G13) to replace the original crotonyl side chain (inhibitor XL-01 to XL-16, Table 1). At the same time, a compound with cyclopentanecarbonyl group (XL-17, Table 1), lacking the conjugated π-system, was also obtained as a negative control. The base peptide in Table is SEQ ID NO:49.

TABLE 1

H₂N-Lys-Gln-Thr-Ala-Arg-Lys-Ser-Thr-Gly-Gly-CONH₂

| Compound | R |
|---|---|
| H3K9cr | propenyl |
| XL-01 | CH=CH-CF₃ |
| XL-02 | phenyl |
| XL-03 | 2-pyridyl |
| XL-04 | 3-pyridyl |
| XL-05 | 4-pyridyl |
| XL-06 | pyrimidinyl |
| XL-07 | 2-furyl |
| XL-08 | 3-furyl |
| XL-09 | 2-thienyl |
| XL-10 | 3-thienyl |
| XL-11 | pyrrolyl |
| XL-12 | isoxazolyl |
| XL-13 | oxazolyl |

TABLE 1-continued

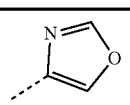

H₂N-Lys-Gln-Thr-Ala-Arg-Lys-Ser-Thr-Gly-Gly-CONH₂

| Compound | R |
|---|---|
| XL-14 | 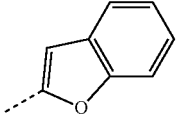 |
| XL-15 | |
| XL-16 | |
| XL-17 | |

Example 2. Generation of Inhibitors

Figure 46:
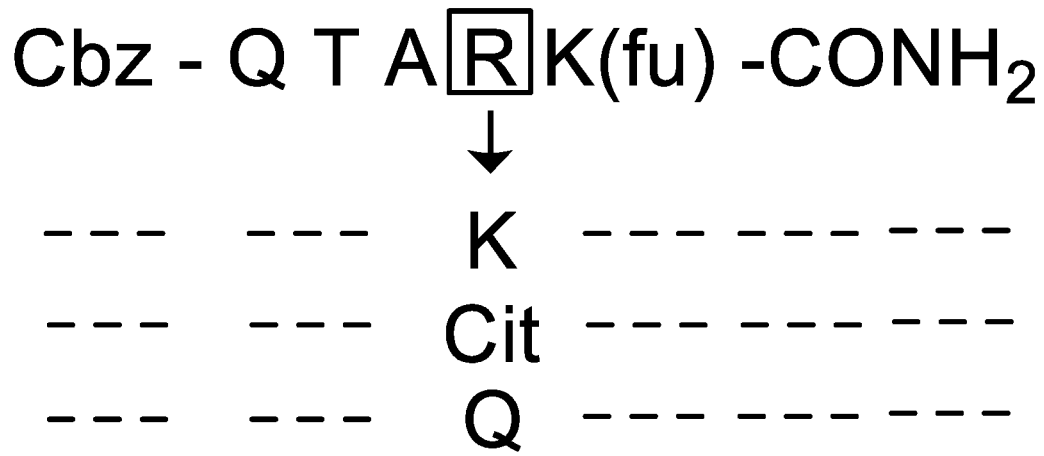
FIG. 46 shows alternative substituents for the arginine residue in the QTARK sequence; such as lysine, citrulline and glutamine (SEQ ID NO:21). For mutation to Lys, the positive charge was kept, while for Cit and Gln, the positive charge was blocked or converted to a negative charge.

To study the significance of the "H3R8-D103" interactions, the arginine residue was modified to three other amino acids including lysine, citrulline and glutamine (FIG. 46). For mutation to Lys, the positive charge was kept, while for Cit and Gln, the positive charge was blocked or converted to a negative charge. By comparing the signal intensities of peptide control, competitor R8-K, R8-Cit, and R8-Q at 0.3 μM, the activities of inhibitors can be preliminary estimated. The strong fluorescent signal intensities of samples R8-K, R8-Cit, and R8-Q indicated that a relatively small portion of AF9 binds to competitors. Comparison to the previous inhibitor (peptide control), shows that these three competitors interact with the AF9 YEATS domain weakly.

Figure 47:
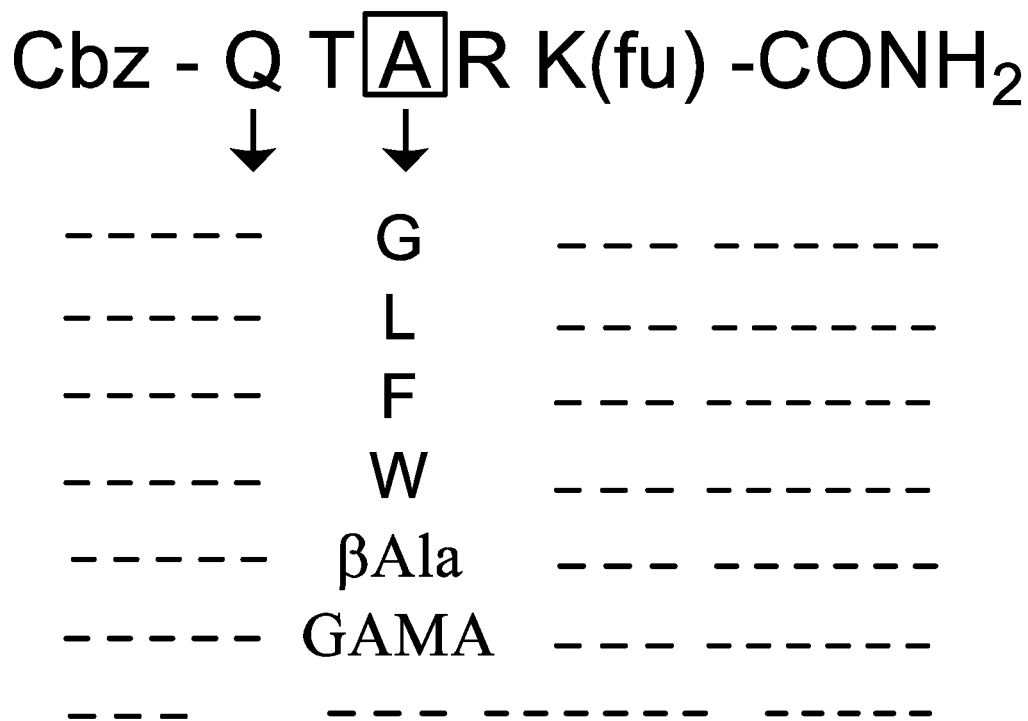
FIG. 47 shows alternative substituents for the alanine residue in the QTARK sequence; such as glycine, leucine, phenylalanine, tryptophan, β-alanine or γ-aminobutyric acid (GABA) (SEQ ID NO:22).

Next, modification on H3A7 was studied. For alanine, the α-carbon is bound to a methyl group. Mutations of alanine to glycine, leucine, phenylalanine, tryptophan, β-alanine or γ-aminobutyric acid (GABA) were made (FIG. 47). Modification to leucine (A7-L) and tryptophan (A7-W) demonstrated comparable results. These two competitors were selected for further study.

For competitor Q5-N, the side chain amide is replaced by a carboxyl group. The activity of inhibitor drops when the glutamine is modified to glutamic acid. At physiological pH, the side chain of threonine is polar and uncharged. Modification of this residue to other neutral residues such as Val, Ala, Leu, Ser and HoF resulted in loss of binding.

The effects of other modifications were also tested. Simultaneous modification of the threonine and alanine residues to Ava, Ahx, GABA and AMC, led to a significant drop in inhibitory activity. For competitor Control-COOH, the C-terminal amide was replaced by a carboxylic acid group. This —COOH can form a carboxylate anion after deprotonation to yield a negative charge. Yet, this inhibitor exhibited no significant improvement.

The N-terminus of competitor was modified as well. The K4 residue of H3 peptide is sandwiched between the H107 and H111 residues of AF9. Histidine bears an aromatic imidazole side chain. Previously we found that by replacing Lys4 to the aromatic Cbz group, the binding affinity of competitor increased. Inspired by this finding, other aromatic groups were incorporated into the N-termini of competitors so as to enhance the π-π stacking interaction between inhibitor and the AF9 YEATS domain. Competitor Cbz-4, with an extended aromatic system, displayed comparable binding affinity to AF9. Strikingly, modification of native Gln to beta-Gln resulted in a dramatic binding loss.

In summary, preliminary screening for all peptide-based inhibitors showed that competitors A7-L, A7-W, T6-S, T6-A and Cbz-4 exhibited comparable inhibitory activities.

Example 3. Activity Estimation by Photo-Cross-Linking-Based Competition

Figure 28:
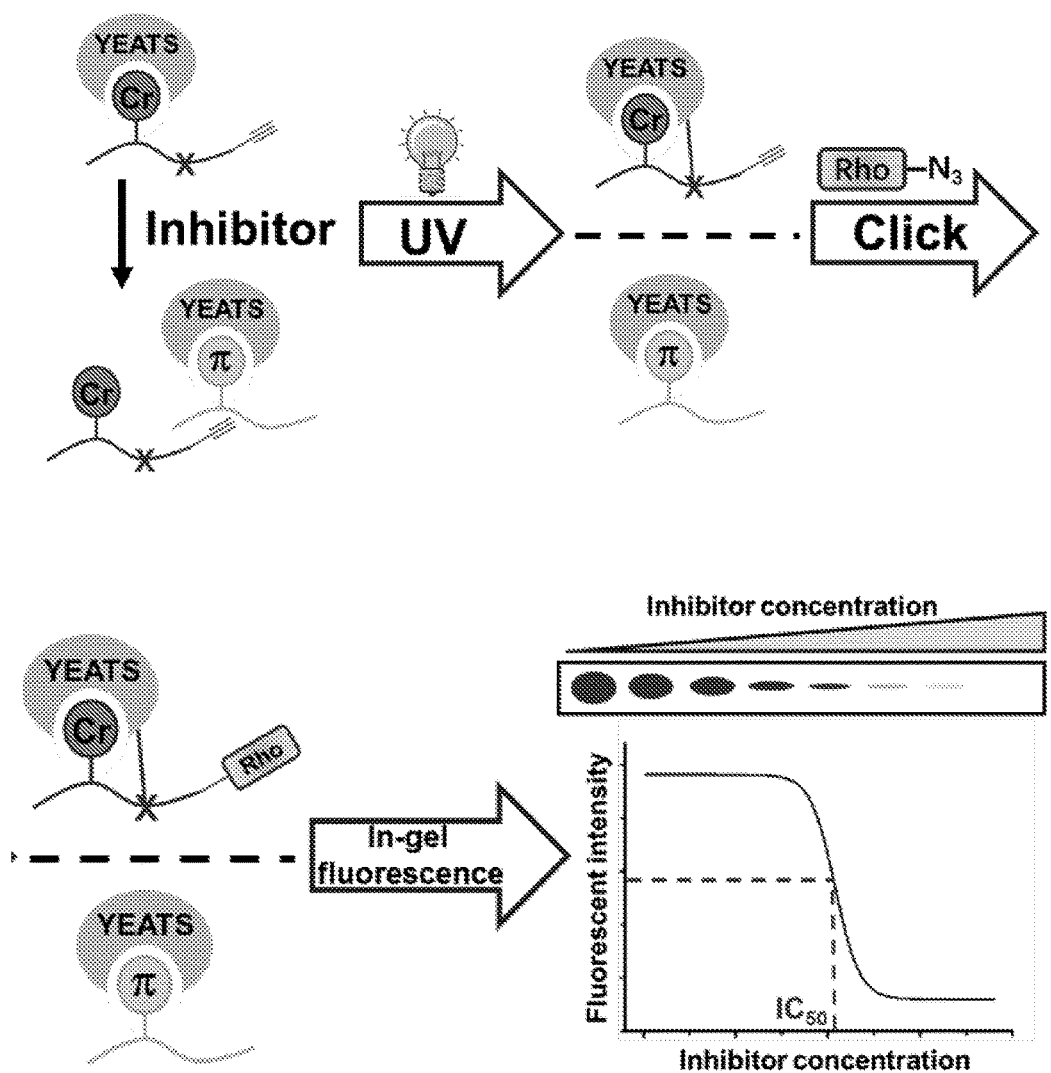
FIG. 28 is a schematic illustrating the strategy for estimating inhibitory activity of compounds using a photoaffinity probe. The YEATS domain is incubated and bound to the probe through Kcr-dependent recognition. Upon UV-irradiation, the photo-cross-linker is activated and rapidly cross-linked to the protein, converting the non-covalent protein-probe interaction into a covalent linkage. The probe-labeled protein is subsequently conjugated to an azide-functionalized fluorescence dye (for example, rhodamine-N3, Rho-N3) via Cu(I)-catalyzed azide-alkyne cycloaddition (CuAAC, or "click" chemistry). After SDS-PAGE, the protein can be visualized by in-gel fluorescence scanning.
Figure 29:
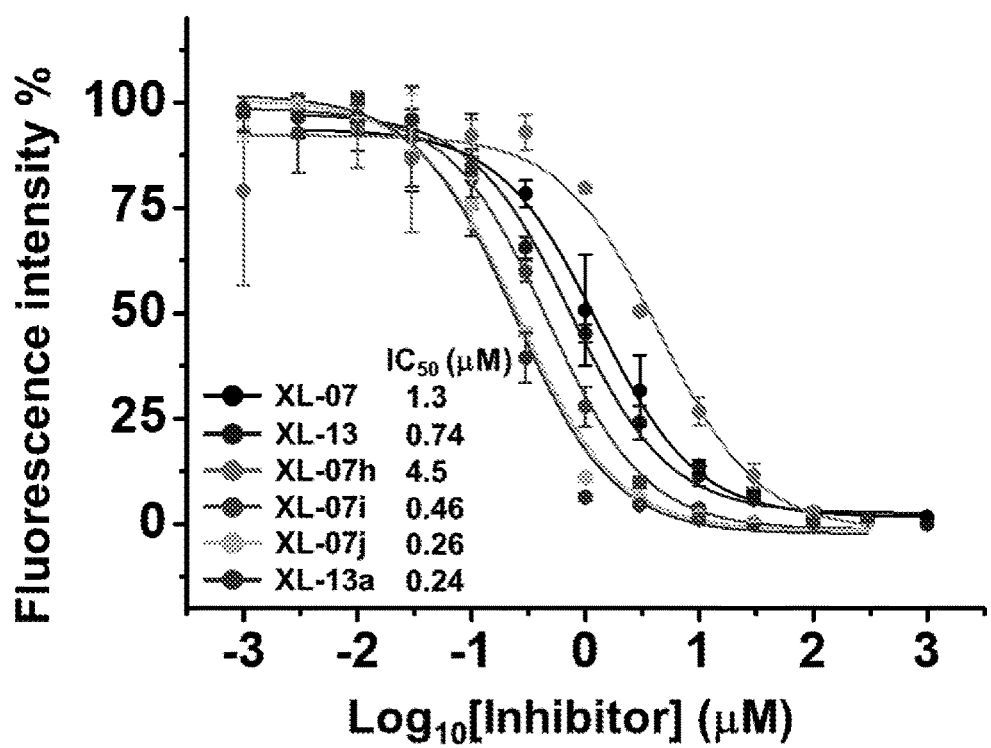
FIG. 29 is a graph showing the effects of concentrations of compounds on the relative fluorescence intensity of probe-labeled protein, leading to determination of $IC_{50}$. $IC_{50}$ values of compounds 7 (XL-07), 13 (XL-13), 27 (XL-07h), 25 (XL-07i), 26 (XL-07j), and 27 (XL-13a) based on their interaction with the AF9 YEATS domain are shown.

A photo-cross-linking based method was used in this study to estimate inhibitory activity (FIG. 28). This method requires the use of a photoaffinity probe. The probe (probe 1 (SEQ ID NO:48), see below) is derived from a crotonylated peptide, ligand of the protein, carrying a photo-cross-linker and a terminal alkyne as bioorthogonal.

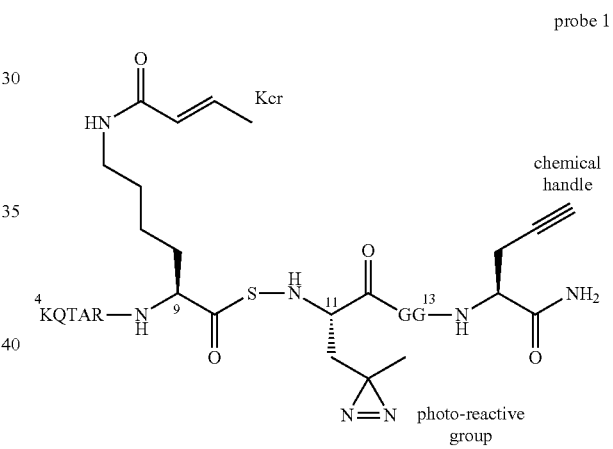

probe 1

The YEATS domain is incubated and bound to the probe through Kcr-dependent recognition. Upon UV-irradiation, the photo-cross-linker is activated and rapidly cross-linked to the protein, converting the non-covalent protein-probe interaction into a covalent linkage. The probe-labeled protein is subsequently conjugated to an azide-functionalized fluorescence dye (for example, rhodamine-N3, Rho-N3) via Cu(I)-catalyzed azide-alkyne cycloaddition (CuAAC, or "click" chemistry). After SDS-PAGE, the protein can be visualized by in-gel fluorescence scanning. If photo-cross-linking of the YEATS domain with photoaffinity probe is performed in the presence of an inhibitor, which occupies the Kcr binding pocket of the YEATS domain and thus inhibits the protein-probe interaction, the percentage of the YEATS domain in the sample that is labeled by the probe will be reduced. The in-gel fluorescence intensity detected will also be decreased. By varying the concentration of inhibitor added in the sample and quantifying the resulting fluorescence intensities, a competition curve of the inhibitor toward the protein-probe interaction will be obtained, which can be used to estimate the IC₅₀ value. Due to the covalent nature of photo-cross-linking, weak protein-protein interactions can be captured and eventually visualized. The protein concentration used in the assay can be as low as several nanograms per microliter, while the fluorescence signal can still be robustly detected and quantified.

In probe 1, the original T11 residue was replaced by a diazirine-based photo-reactive amino acid, photo-leucine. In the reported crystal structure of AF9 YEATS-H3K9cr complex, the T11 is invisible (although an H3K9cr peptide with A1-A15 in sequence was used for crystallization), suggesting a minor role of this residue in the protein-peptide interaction. The incorporation of photo-leucine at this position is thus not likely to interfere with the protein-probe interaction. Meanwhile, this position is close enough to the Kcr-binding site of the target protein, ensuring cross-linking efficiency and specificity.

Figure 7:
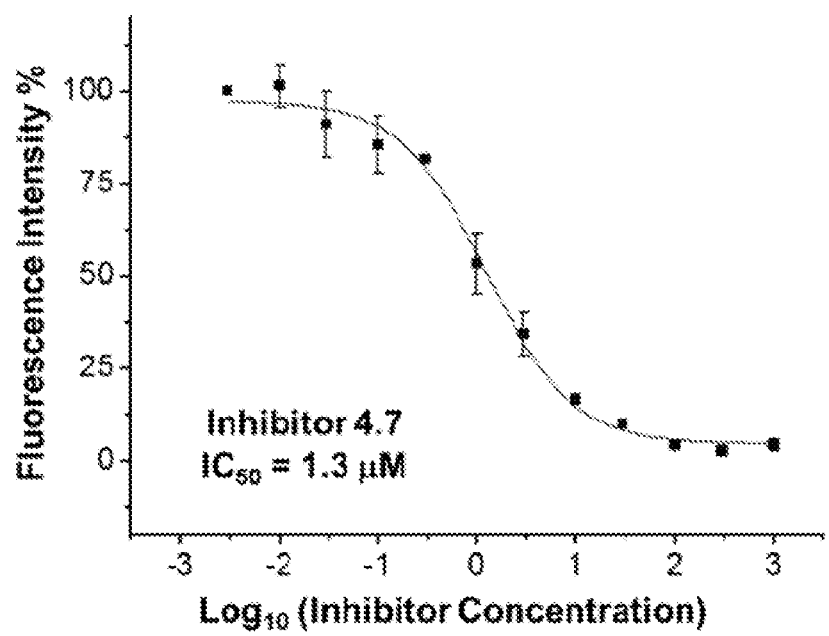
FIG. 7 is a graph showing the effects of compound 7 inhibitor concentration on the actual fluorescence intensity of probe-labeled protein, leading to determination of $IC_{50}$.
Figure 8:
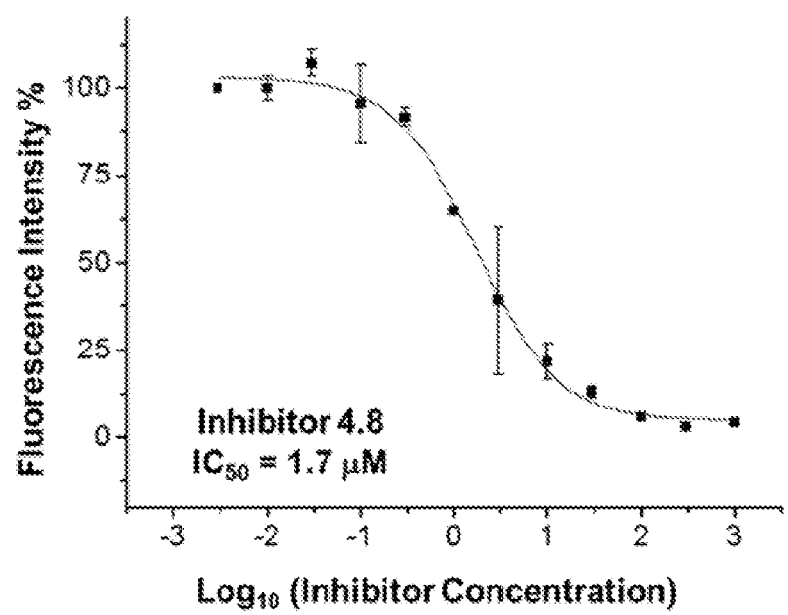
FIG. 8 is a graph showing the effects of compound 8 inhibitor concentration on the actual fluorescence intensity of probe-labeled protein, leading to determination of $IC_{50}$.
Figure 9:
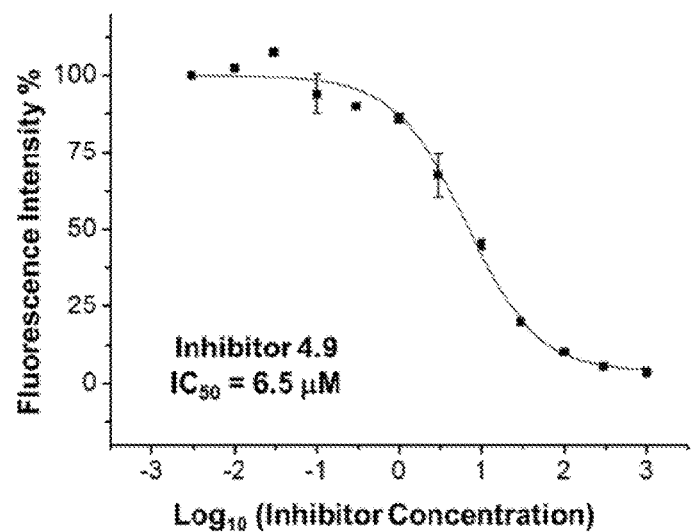
FIG. 9 is a graph showing the effects of compound 9 inhibitor concentration on the actual fluorescence intensity of probe-labeled protein, leading to determination of $IC_{50}$.
Figure 10:
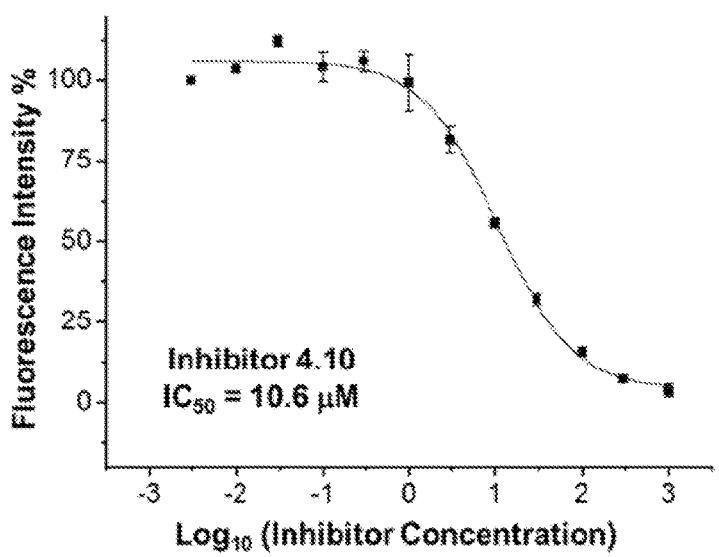
FIG. 10 is a graph showing the effects of compound 10 inhibitor concentration on the actual fluorescence intensity of probe-labeled protein, leading to determination of $IC_{50}$.
Figure 11:
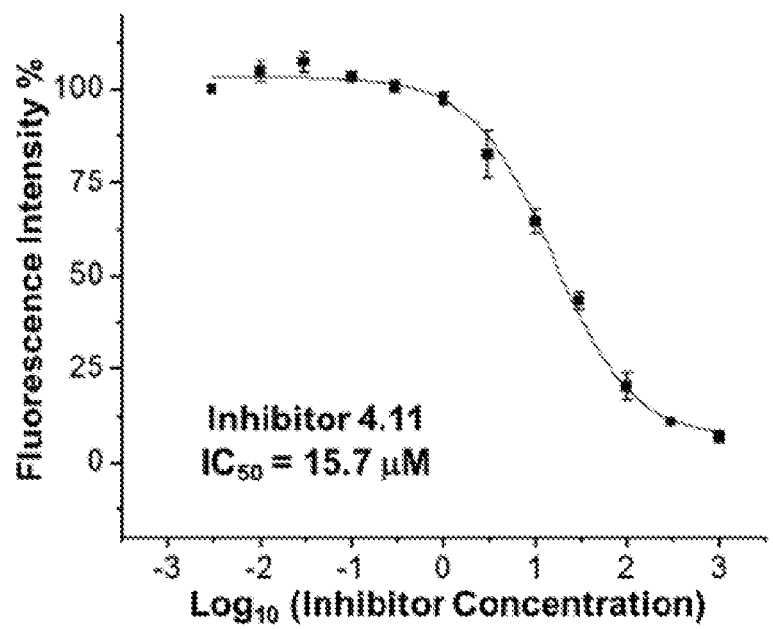
FIG. 11 is a graph showing the effects of compound 11 inhibitor concentration on the actual fluorescence intensity of probe-labeled protein, leading to determination of $IC_{50}$.
Figure 12:
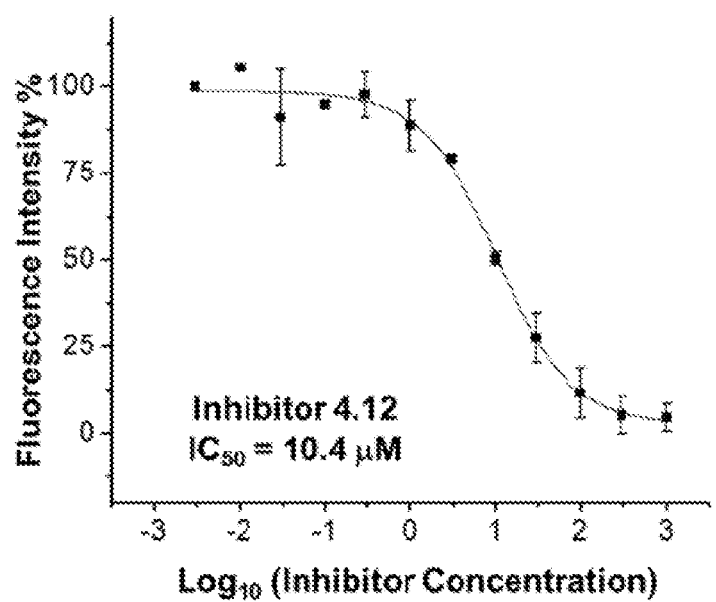
FIG. 12 is a graph showing the effects of compound 12 inhibitor concentration on the actual fluorescence intensity of probe-labeled protein, leading to determination of $IC_{50}$.
Figure 13:
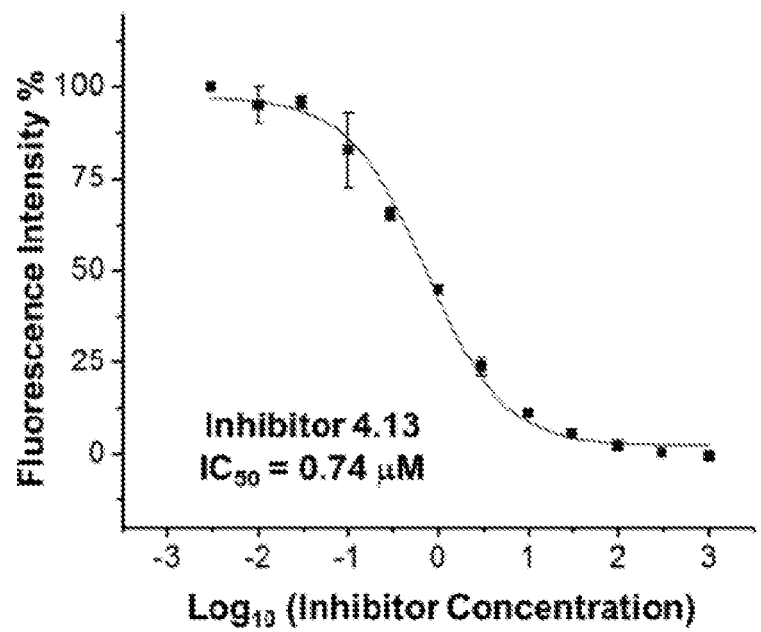
FIG. 13 is a graph showing the effects of compound 13 inhibitor concentration on the actual fluorescence intensity of probe-labeled protein, leading to determination of $IC_{50}$.
Figure 14:
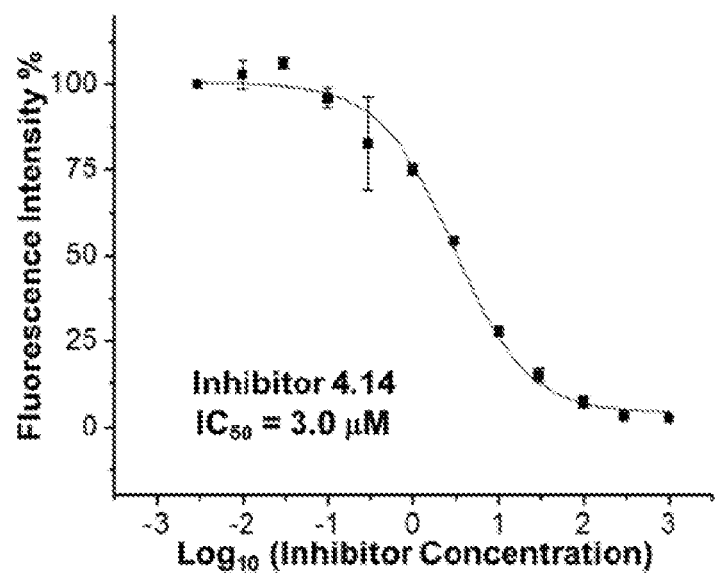
FIG. 14 is a graph showing the effects of compound 14 inhibitor concentration on the actual fluorescence intensity of probe-labeled protein, leading to determination of $IC_{50}$.
Figure 15:
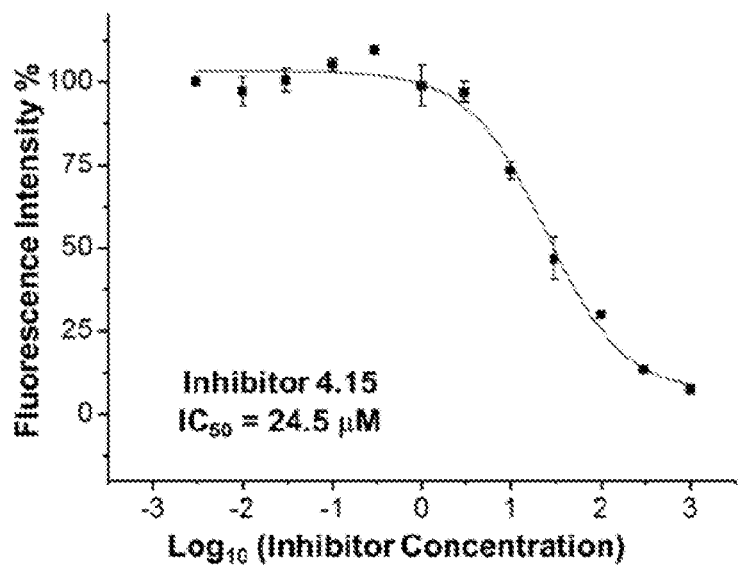
FIG. 15 is a graph showing the effects of compound 15 inhibitor concentration on the actual fluorescence intensity of probe-labeled protein, leading to determination of $IC_{50}$.
Figure 16:
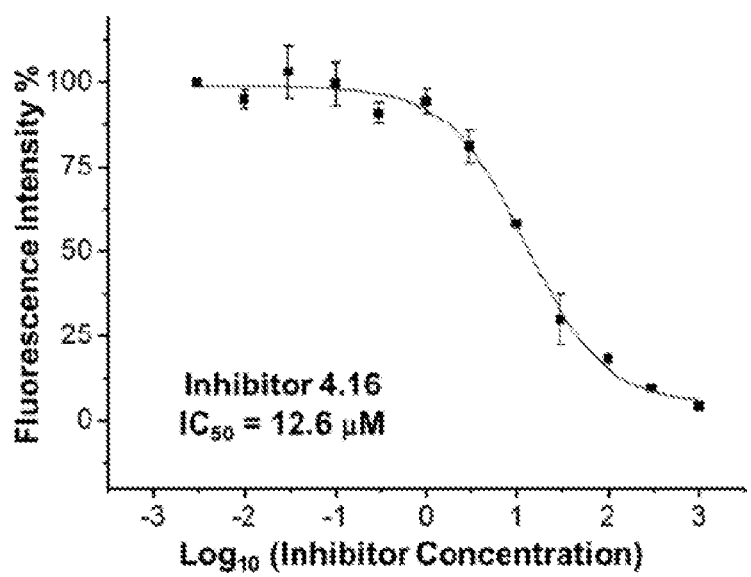
FIG. 16 is a graph showing the effects of compound 16 inhibitor concentration on the actual fluorescence intensity of probe-labeled protein, leading to determination of $IC_{50}$.
Figure 17:
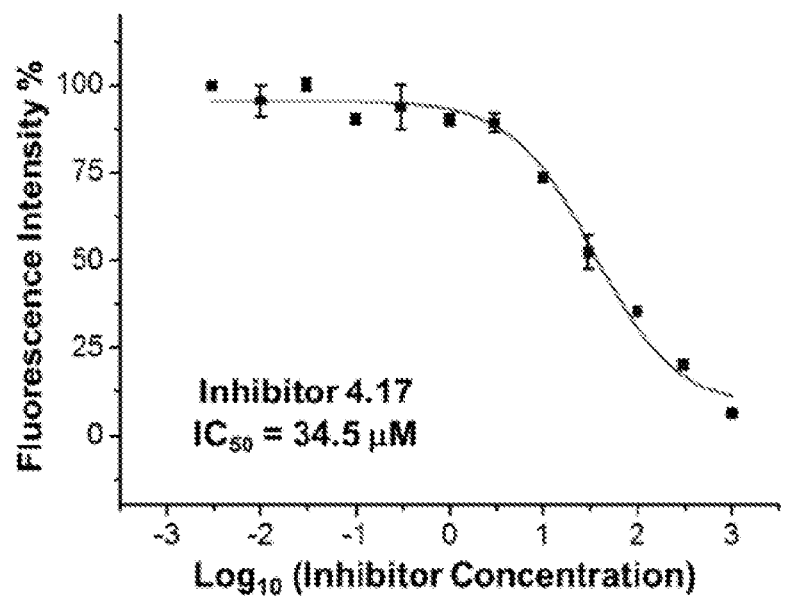
FIG. 17 is a graph showing the effects of compound 84 inhibitor concentration on the actual fluorescence intensity of probe-labeled protein, leading to determination of $IC_{50}$.
Figure 18:
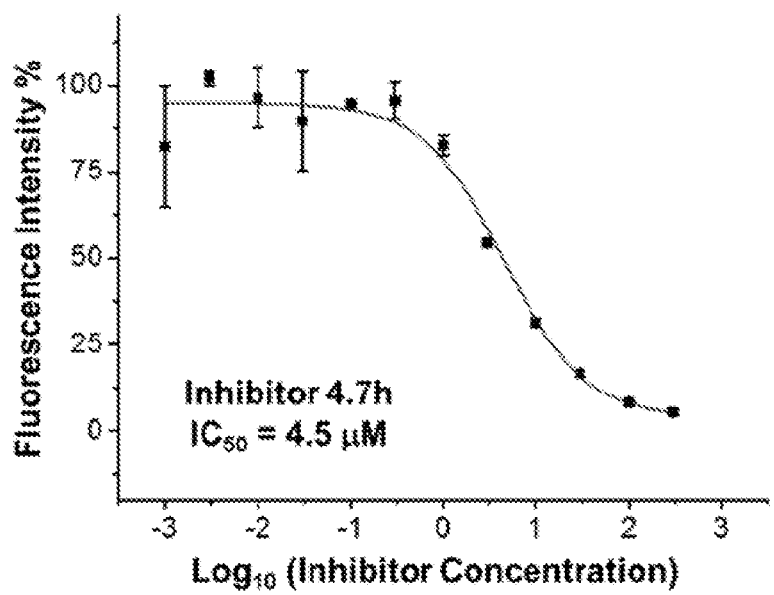
FIG. 18 is a graph showing the effects of compound 7h (24) inhibitor concentration on the actual fluorescence intensity of probe-labeled protein, leading to determination of $IC_{50}$.
Figure 19:
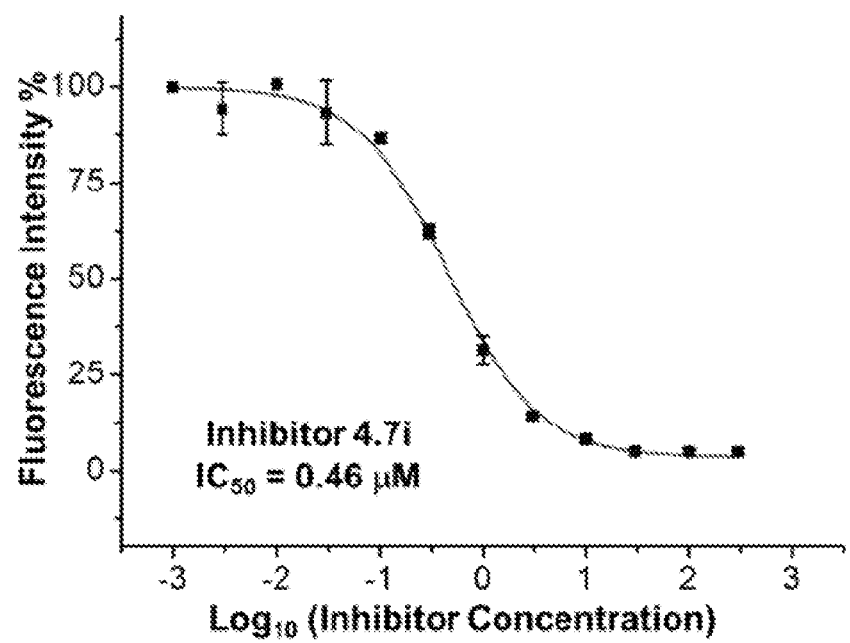
FIG. 19 is a graph showing the effects of compound 7i (25) inhibitor concentration on the actual fluorescence intensity of probe-labeled protein, leading to determination of $IC_{50}$.
Figure 24:
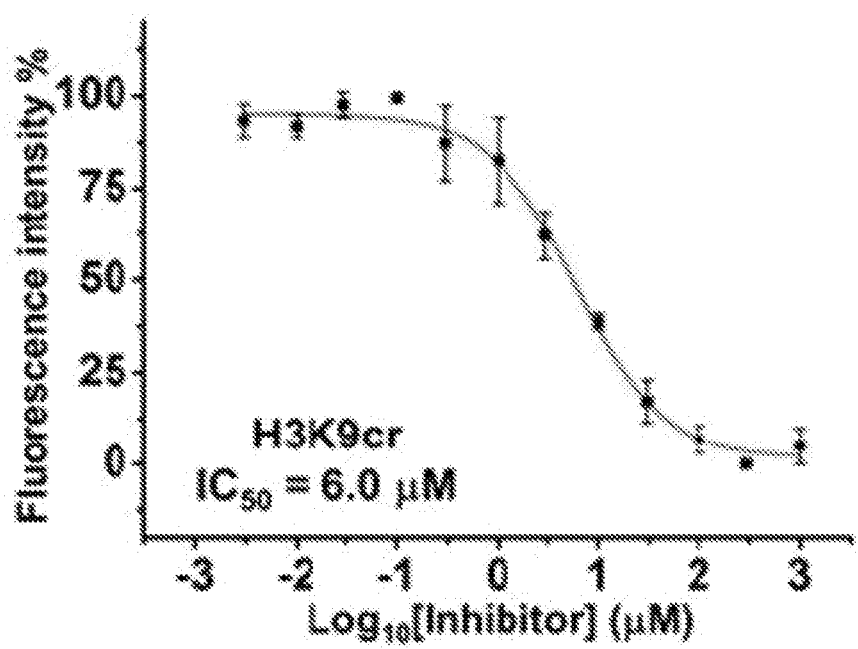
FIG. 24 is a graph showing the effects of H3K9cr peptide (positive control) concentration on the actual fluorescence intensity of probe-labeled protein, leading to determination of $IC_{50}$.
Figure 25:
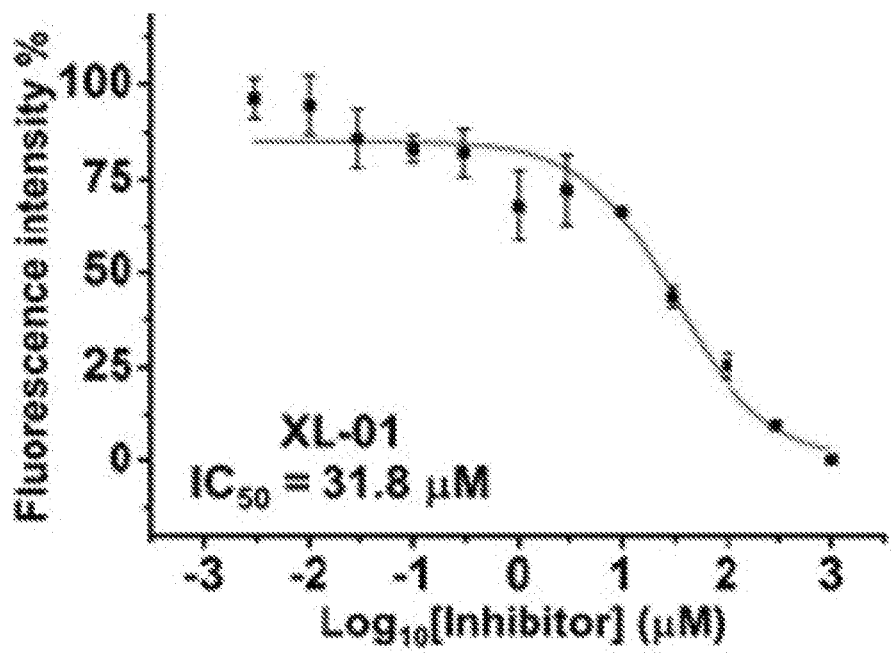
FIG. 25 is a graph showing the effects of compound 1 (XL-01) inhibitor concentration on the actual fluorescence intensity of probe-labeled protein, leading to determination of $IC_{50}$.
Figure 26:
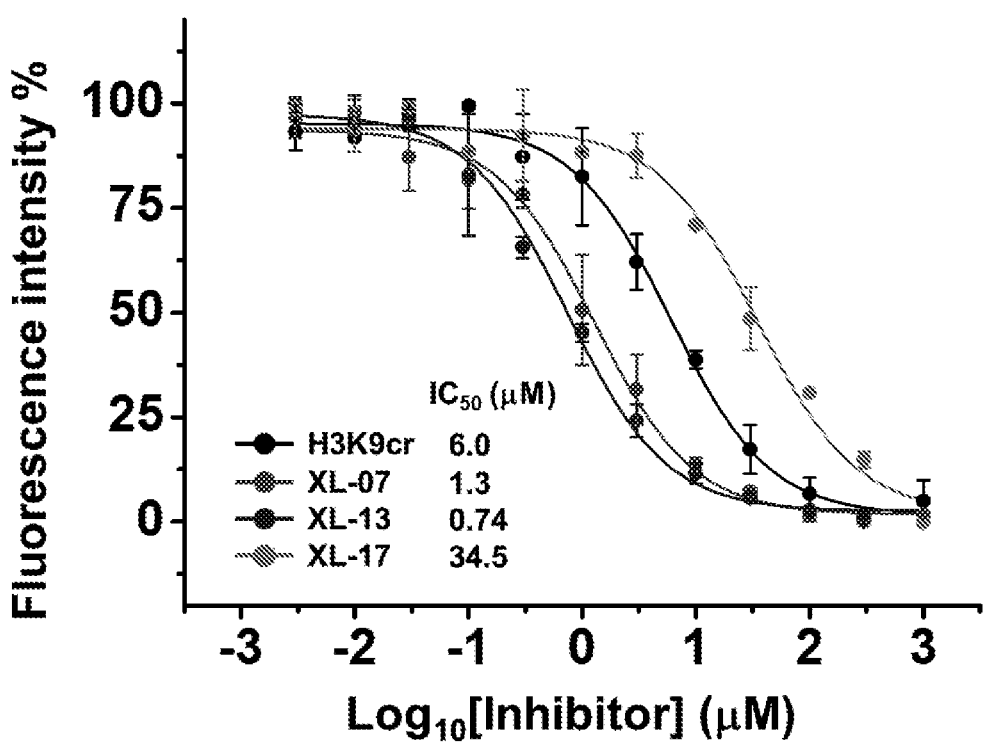
FIG. 26 is a graph showing the effects of concentrations of compounds on the actual fluorescence intensity of probe-labeled protein, leading to determination of $IC_{50}$. Values of compounds 7 (XL-07), 13 (XL-13), and 84 (XL-17) are shown in comparison to the H3K9cr positive control peptide.

Using each of the inhibitors as competitor, the inhibitory activities were tested (FIGS. 2-17, 24, and 25). To our surprise, 6 out of the 17 inhibitors showed higher affinities toward the AF9 YEATS domain than that of the H3K9cr peptide ($IC_{50}$=6.0 μM, FIGS. 24 and 26). Such a high positive rate demonstrates the feasibility of our strategy for inhibitor design by targeting π-π-π stacking. Two inhibitors carrying a 2-furancarbonyl side chain (XL-07 (alternative name: 4.7), Table 1) and a 5-oxazolecarbonyl side chain (XL-13 (alternative name: 4.13), Table 1) resulted in the strongest inhibitory activities with $IC_{50}$ values of 1.3 and 0.74 μM respectively (FIGS. 26, 7, and 13). As expected, the negative control compound XL-17, without a conjugated π-system, displayed the lowest activity among all the tested inhibitors ($IC_{50}$=34.5 μM, FIGS. 17 and 26).

The $IC_{50}$ values for competitors Cbz-4, A7-L, A7-W, T6-A and T6-S, were determined to be 0.226 μM, 0.338 μM, 0.315 μM, 0.715 μM and 0.778 μM, respectively. Compared to the peptide control (0.189 μM), no competitor demonstrated improvement of inhibitory activity. Among the selected competitors, competitor Cbz-4, with a 2-naphthaleneacetyl group in the N-terminus, showed best binding affinity to the AF9 YEATS domain.

The fluorescence intensities for the inhibitors tested are illustrated in FIGS. 1-22, 24-26, and 29-45. The $IC_{50}$ values for the inhibitors are listed in Table 2. The $IC_{50}$ for the native ligand, H3K9cr peptide, was estimated as 6.0 μM (FIG. 22). 22 out of the total 82 inhibitors exhibited small $IC_{50}$ values compared with the H3K9cr peptide (compound 83). These included compound 5, with a isonicotinoyl side chain ($IC_{50}$=2.1 μM (FIG. 5)), compound 6 with a 2-pyrimidinecarbonyl side chain ($IC_{50}$=3.7 μM (FIG. 6)), compound 7 with a 2-furancarbonyl side chain ($IC_{50}$=1.3 μM (FIG. 7)), compound 8 with a 3-furancarbonyl side chain ($IC_{50}$=1.7 μM (FIG. 8)), compound 13 with a 5-oxazolecarbonyl side chain ($IC_{50}$=0.74 μM (FIG. 13)), compound 14 with 4-oxazolecarbonyl side chain ($IC_{50}$=3.0 μM (FIG. 14)), compound 24 with a 2-furancarbonyl side chain ($IC_{50}$=4.5 μM), compound 25 with a 2-furancarbonyl side chain ($IC_{50}$=0.46 μM), compound 26 with a 2-furancarbonyl side chain ($IC_{50}$=0.26 μM), compound 27 with a 5-oxazolecarbonyl side chain ($IC_{50}$=0.24 μM), compound 39 with a 2-furancarbonyl side chain ($IC_{50}$=2.5 μM), compound 40 with a 2-furancarbonyl side chain ($IC_{50}$=1.7 μM), compound 47 with a 2-furancarbonyl side chain ($IC_{50}$=0.34 μM), compound 49 with a 2-furancarbonyl side chain ($IC_{50}$=0.32 μM), compound 53 with a 2-furancarbonyl side chain ($IC_{50}$=0.72 μM), compound 55 with a 2-furancarbonyl side chain ($IC_{50}$=0.78 μM), compound 74 with a 2-furancarbonyl side chain ($IC_{50}$=0.23 μM), compound 78 with a 2-furancarbonyl side chain ($IC_{50}$=2.2 μM), compound 79 with a 2-furancarbonyl side chain ($IC_{50}$=1.8 μM), compound 80 with a 5-oxazolecarbonyl side chain ($IC_{50}$=5.1 μM), compound 81 with a 5-oxazolecarbonyl side chain ($IC_{50}$=2.3 μM), and compound 82 with a 5-oxazolecarbonyl side chain ($IC_{50}$=2.8 μM). As expected, the negative control compound 84, without the π-system, exhibited the lowest activity among all the tested inhibitors ($IC_{50}$=34.5 μM (FIG. 17)).

Figure 20:
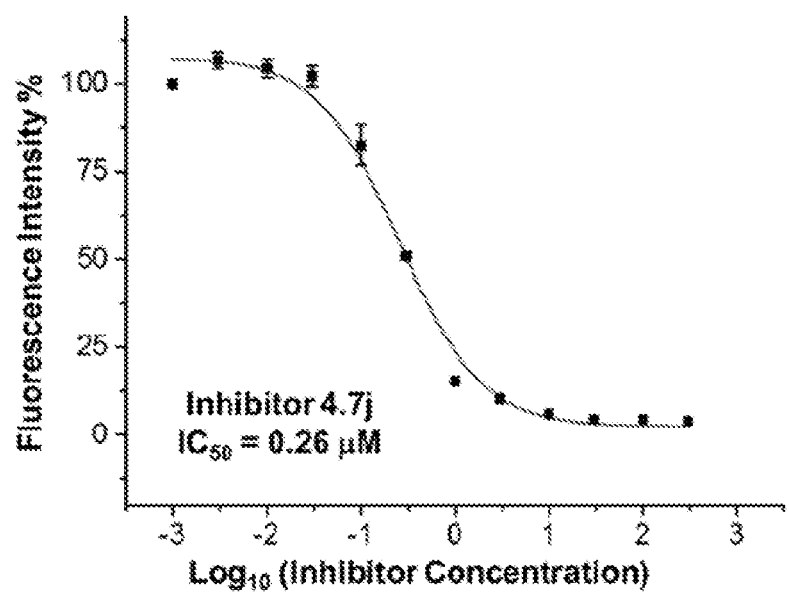
FIG. 20 is a graph showing the effects of compound 7j (26) inhibitor concentration on the actual fluorescence intensity of probe-labeled protein, leading to determination of $IC_{50}$.
Figure 21:
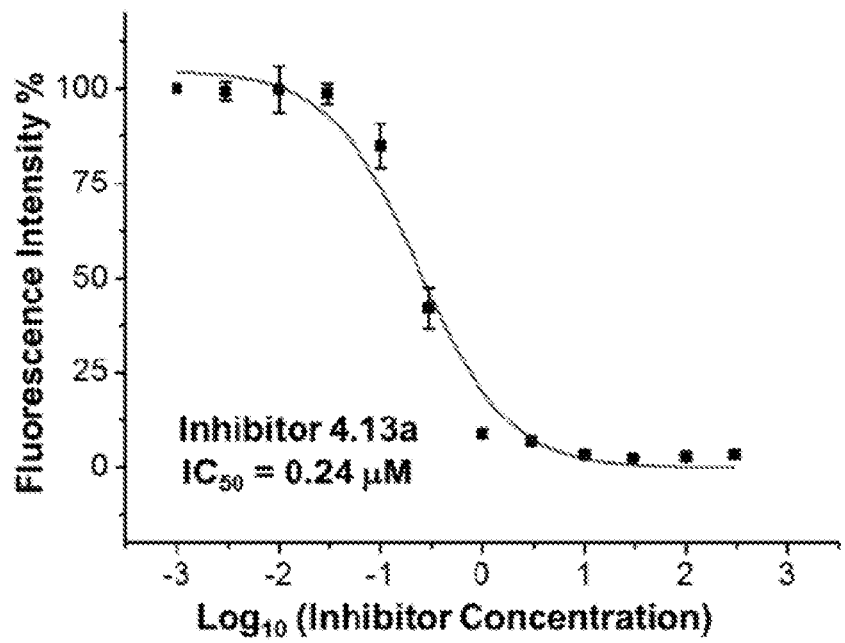
FIG. 21 is a graph showing the effects of compound 13a (27) inhibitor concentration on the actual fluorescence intensity of probe-labeled protein, leading to determination of $IC_{50}$.
Figure 22:
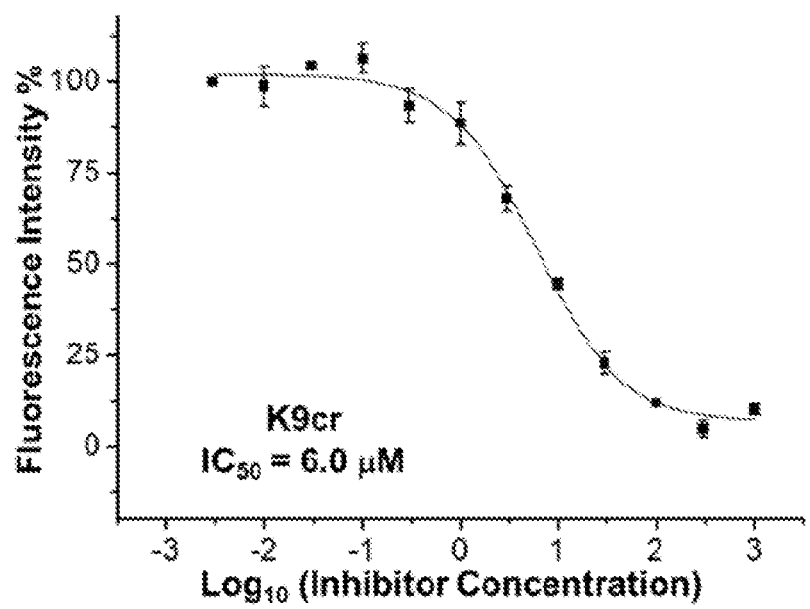
FIG. 22 is a graph showing the effects of compound 83 inhibitor concentration on the actual fluorescence intensity of probe-labeled protein, leading to determination of $IC_{50}$.

Further modifications on the sequence of the peptide inhibitors resulted in two potent Cbz-QTARK-CONH$_2$ (SEQ ID NO:4) pentapeptide inhibitors with furancarbonyl (compound 26 (7j), Kd 330 nM) and 5-oxazolecarbonyl (compound 27 (13a), Kd 131 nM) side chain on the lysine residue (FIGS. 20 and 21, respectively).

TABLE 2

| Compound No. | Alternative names | Structure | Activity ($IC_{50}$, μM) |
|---|---|---|---|
| 1 | 1, 4.1, XL-01 (SEQ ID NO: 23) | [Structure: O=C-CH=CH-CF$_3$ with HN-(CH$_2$)$_4$- linker; H$_2$N-Lys-Gln-Thr-Ala-Arg-Lys-Ser-Thr-Gly-Gly-CONH$_2$] | 27.9 on AF9 |
| 2 | 2, 4.2, XL-02 (SEQ ID NO: 24) | [Structure: O=C-phenyl with HN-(CH$_2$)$_4$- linker; H$_2$N-Lys-Gln-Thr-Ala-Arg-Lys-Ser-Thr-Gly-Gly-CONH$_2$] | 29.8 on AF9 |

TABLE 2-continued

| Compound No. | Alternative names | Structure | Activity (IC$_{50}$, μM) |
|---|---|---|---|
| 3 | 3, 4.3, XL-03 (SEQ ID NO: 25) | 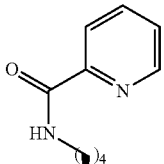<br>H$_2$N-Lys-Gln-Thr-Ala-Arg-Lys-Ser-Thr-Gly-Gly-CONH$_2$ | 22.1 on AF9 |
| 4 | 4, 4.4, XL-04 (SEQ ID NO: 25) | 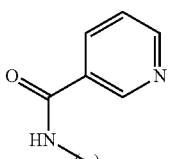<br>H$_2$N-Lys-Gln-Thr-Ala-Arg-Lys-Ser-Thr-Gly-Gly-CONH$_2$ | 22.2 on AF9 |
| 5 | 5, 4.5, XL-05 (SEQ ID NO: 25) | 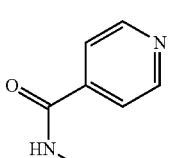<br>H$_2$N-Lys-Gln-Thr-Ala-Arg-Lys-Ser-Thr-Gly-Gly-CONH$_2$ | 2.1 on AF9 |
| 6 | 6, 4.6, XL-06 (SEQ ID NO: 26) | <br>H$_2$N-Lys-Gln-Thr-Ala-Arg-Lys-Ser-Thr-Gly-Gly-CONH$_2$ | 3.7 on AF9 |
| 7 | 7, 4.7, XL-07 (SEQ ID NO: 27) | 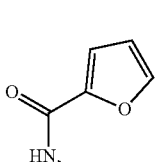<br>H$_2$N-Lys-Gln-Thr-Ala-Arg-Lys-Ser-Thr-Gly-Gly-CONH$_2$ | 1.3 on AF9 |
| 8 | 8, 4.8, XL-08 (SEQ ID NO: 27) | 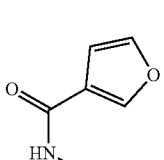<br>H$_2$N-Lys-Gln-Thr-Ala-Arg-Lys-Ser-Thr-Gly-Gly-CONH$_2$ | 1.7 on AF9 |

TABLE 2-continued

| Compound No. | Alternative names | Structure | Activity (IC$_{50}$, μM) |
|---|---|---|---|
| 9 | 9, 4.9, XL-09 (SEQ ID NO: 28) | thiophene-2-carboxamide linked via (CH$_2$)$_4$ to H$_2$N-Lys-Gln-Thr-Ala-Arg-Lys-Ser-Thr-Gly-Gly-CONH$_2$ | 6.5 on AF9 |
| 10 | 10, 4.10, XL-10 (SEQ ID NO: 28) | thiophene-3-carboxamide linked via (CH$_2$)$_4$ to H$_2$N-Lys-Gln-Thr-Ala-Arg-Lys-Ser-Thr-Gly-Gly-CONH$_2$ | 10.6 on AF9 |
| 11 | 11, 4.11, XL-11 (SEQ ID NO: 29) | pyrrole-1-carboxamide linked via (CH$_2$)$_4$ to H$_2$N-Lys-Gln-Thr-Ala-Arg-Lys-Ser-Thr-Gly-Gly-CONH$_2$ | 15.7 on AF9 |
| 12 | 12, 4.12, XL-12 (SEQ ID NO: 30) | isoxazole-5-carboxamide linked via (CH$_2$)$_4$ to H$_2$N-Lys-Gln-Thr-Ala-Arg-Lys-Ser-Thr-Gly-Gly-CONH$_2$ | 10.4 on AF9 |
| 13 | 13, 4.13, XL-13 (SEQ ID NO: 30) | oxazole-5-carboxamide linked via (CH$_2$)$_4$ to H$_2$N-Lys-Gln-Thr-Ala-Arg-Lys-Ser-Thr-Gly-Gly-CONH$_2$ | 0.74 on AF9 |
| 14 | 14, 4.14, XL-14 (SEQ ID NO: 30) | oxazole-4-carboxamide linked via (CH$_2$)$_4$ to H$_2$N-Lys-Gln-Thr-Ala-Arg-Lys-Ser-Thr-Gly-Gly-CONH$_2$ | 3.0 on AF9 |

TABLE 2-continued
| Compound No. | Alternative names | Structure | Activity (IC$_{50}$, μM) |
|---|---|---|---|
| 15 | 15, 4.15, XL-15 (SEQ ID NO: 31) | 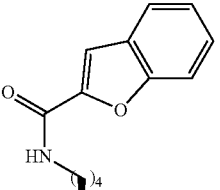<br>H$_2$N-Lys-Gln-Thr-Ala-Arg-Lys-Ser-Thr-Gly-Gly-CONH$_2$ | 24.5 on AF9 |
| 16 | 16, 4.16, XL-16 (SEQ ID NO: 31) | 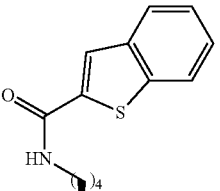<br>H$_2$N-Lys-Gln-Thr-Ala-Arg-Lys-Ser-Thr-Gly-Gly-CONH$_2$ | 12.6 on AF9 |
| 17 | 7a, 4.7a, XL-07a | 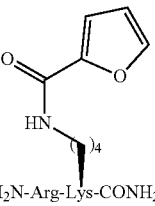<br>H$_2$N-Arg-Lys-CONH$_2$ | NT |
| 18 | 7b, 4.7b, XL-07b | 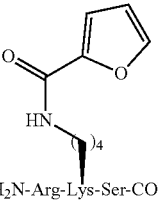<br>H$_2$N-Arg-Lys-Ser-CONH$_2$ | NT |
| 19 | 7c, 4.7c, XL-07c (SEQ ID NO: 32) | 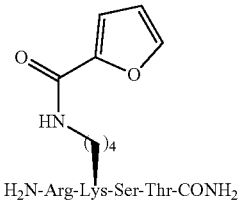<br>H$_2$N-Arg-Lys-Ser-Thr-CONH$_2$ | NT |
| 20 | 7d, 4.7d, XL-07d | 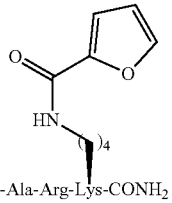<br>H$_2$N-Ala-Arg-Lys-CONH$_2$ | NT |

TABLE 2-continued

| Compound No. | Alternative names | Structure | Activity (IC$_{50}$, μM) |
|---|---|---|---|
| 21 | 7e, 4.7e, XL-07e (amino acids 1-4 of SEQ ID NO: 33) | H$_2$N-Ala-Arg-Lys-Ser-CONH$_2$ (with furan-2-carboxamide on Lys side chain, (CH$_2$)$_4$) | NT |
| 22 | 7f, 4.7f, XL-07f (SEQ ID NO: 33) | H$_2$N-Ala-Arg-Lys-Ser-Thr-CONH$_2$ (with furan-2-carboxamide on Lys side chain, (CH$_2$)$_4$) | NT |
| 23 | 7g, 4.7g, XL-07g (amino acids 3-6 of SEQ ID NO: 34) | H$_2$N-Thr-Ala-Arg-Lys-CONH$_2$ (with furan-2-carboxamide on Lys side chain, (CH$_2$)$_4$) | NT |
| 24 | 7h, 4.7h, XL-07h (amino acids 2-6 of SEQ ID NO: 34) | H$_2$N-Gln-Thr-Ala-Arg-Lys-CONH$_2$ (with furan-2-carboxamide on Lys side chain, (CH$_2$)$_4$) | 4.5 on AF9 |
| 25 | 7i, 4.7i, XL-07i (SEQ ID NO: 34) | H$_2$N-Lys-Gln-Thr-Ala-Arg-Lys-CONH$_2$ (with furan-2-carboxamide on Lys side chain, (CH$_2$)$_4$) | 0.46 on AF9 |
| 26 | 7j, 4.7j, XL-07j (SEQ ID NO: 35) | CbzHN-Gln-Thr-Ala-Arg-Lys-CONH$_2$ (with furan-2-carboxamide on Lys side chain, (CH$_2$)$_4$) | 0.26 on AF9<br>1.3 on ENL<br>42.4 on YEATS2<br>123.1 on Gas41 |
| 27 | 13a, 4.13a, XL-13a (SEQ ID NO: 36) | CbzHN-Gln-Thr-Ala-Arg-Lys-CONH$_2$ (with oxazole-5-carboxamide on Lys side chain, (CH$_2$)$_4$) | 0.24 on AF9<br>0.71 on ENL<br>98.7 on YEATS2<br>14.5 on Gas41 |

TABLE 2-continued

| Compound No. | Alternative names | Structure | Activity (IC$_{50}$, μM) |
|---|---|---|---|
| 28 | XL-13b (SEQ ID NO: 37) | 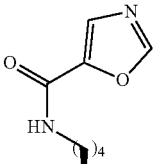 H$_2$N-Thr-Lys-Ala-Ala-Arg-Lys-Ser-Ala-Pro-Ala-Thr-CONH$_2$ | NT |
| 29 | XL-13c (amino acids 1-10 of SEQ ID NO: 37) | 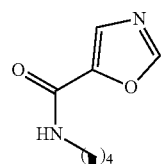 H$_2$N-Thr-Lys-Ala-Ala-Arg-Lys-Ser-Ala-Pro-Ala-CONH$_2$ | NT |
| 30 | XL-13d (amino acids 1-9 of SEQ ID NO: 37) | 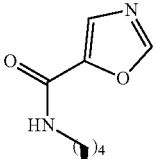 H$_2$N-Thr-Lys-Ala-Ala-Arg-Lys-Ser-Ala-Pro-CONH$_2$ | NT |
| 31 | XL-13e (amino acids 1-8 of SEQ ID NO: 37) | 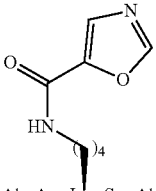 H$_2$N-Thr-Lys-Ala-Ala-Arg-Lys-Ser-Ala-CONH$_2$ | NT |
| 32 | XL-13f (amino acids 1-7 of SEQ ID NO: 37) | 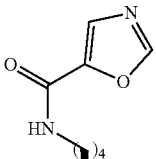 H$_2$N-Thr-Lys-Ala-Ala-Arg-Lys-Ser-CONH$_2$ | NT |
| 33 | XL-13g (amino acids 1-6 of SEQ ID NO: 37) | 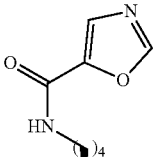 H$_2$N-Thr-Lys-Ala-Ala-Arg-Lys-CONH$_2$ | NT |
| 34 | XL-13h (amino acids 4-10 of SEQ ID NO: 38) | 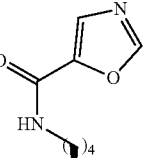 H$_2$N-Arg-Lys-Ser-Ala-Pro-Ala-Thr-CONH$_2$ | NT |

TABLE 2-continued

| Compound No. | Alternative names | Structure | Activity (IC$_{50}$, μM) |
|---|---|---|---|
| 35 | XL-13i (amino acids 3-10 of SEQ ID NO: 38) | 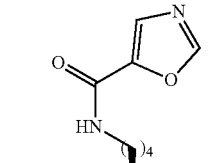 H$_2$N-Ala-Arg-Lys-Ser-Ala-Pro-Ala-Thr-CONH$_2$ | NT |
| 36 | XL-13j (amino acids 2-10 of SEQ ID NO: 38) | 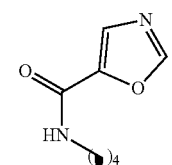 H$_2$N-Ala-Ala-Arg-Lys-Ser-Ala-Pro-Ala-Thr-CONH$_2$ | NT |
| 37 | XL-13k (SEQ ID NO: 38) | 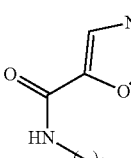 H$_2$N-Lys-Ala-Ala-Arg-Lys-Ser-Ala-Pro-Ala-Thr-CONH$_2$ | NT |
| 38 | XL-13l | 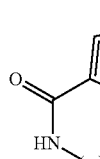 AcHN-Arg-Lys-CONH$_2$ | NT |
| 39 | XL-13m | 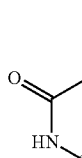 AcHN-Ala-Arg-Lys-CONH$_2$ | 2.5 on AF9 0.56 on ENL 212.9 on YEATS2 52.9 on Gas41 |
| 40 | XL-13n (amino acids 2-5 of SEQ ID NO: 39) | 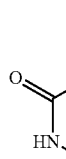 AcHN-Ala-Ala-Arg-Lys-CONH$_2$ | 1.7 on AF9 0.28 on ENL 239.2 on YEATS2 35.5 on Gas41 |

TABLE 2-continued
| Compound No. | Alternative names | Structure | Activity (IC$_{50}$, μM) |
|---|---|---|---|
| 41 | XL-13o (SEQ ID NO: 39) | 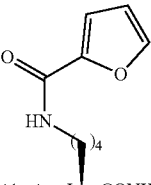 AcHN-Lys-Ala-Ala-Arg-Lys-CONH$_2$ | NT |
| 42 | 7j-OH (SEQ ID NO: 40) | 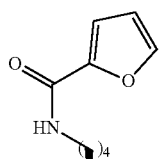 CbzHN-Gln-Thr-Ala-Arg-Lys-COOH | NT |
| 43 | R8-K (SEQ ID NO: 41) | 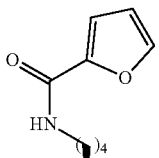 CbzHN-Gln-Thr-Ala-Lys-Lys-CONH$_2$ | NT |
| 44 | R8-Cit | 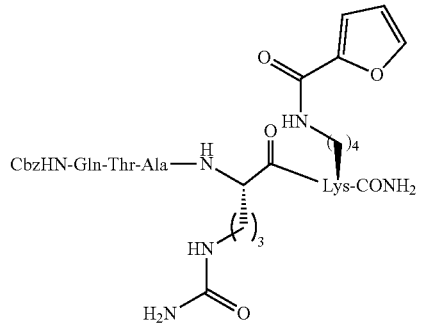 CbzHN-Gln-Thr-Ala—Lys-CONH$_2$ | NT |
| 45 | R8-Q (SEQ ID NO: 41) | 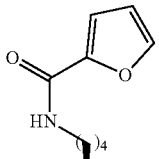 CbzHN-Gln-Thr-Ala-Gln-Lys-CONH$_2$ | NT |
| 46 | A7-G (SEQ ID NO: 42) | 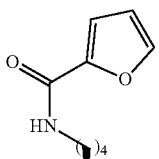 CbzHN-Gln-Thr-Gly-Arg-Lys-CONH$_2$ | NT |

TABLE 2-continued

| Compound No. | Alternative names | Structure | Activity (IC$_{50}$, μM) |
|---|---|---|---|
| 47 | A7-L (SEQ ID NO: 42) | 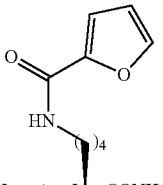<br>CbzHN-Gln-Thr-Leu-Arg-Lys-CONH$_2$ | 0.34 on AF9 |
| 48 | A7-F (SEQ ID NO: 42) | 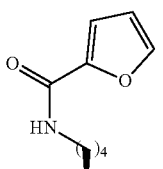<br>CbzHN-Gln-Thr-Phe-Arg-Lys-CONH$_2$ | NT |
| 49 | A7-W (SEQ ID NO: 42) | 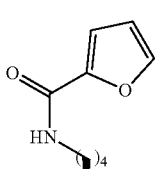<br>CbzHN-Gln-Thr-Trp-Arg-Lys-CONH$_2$ | 0.32 on AF9 |
| 50 | A7-βAla (SEQ ID NO: 42) | 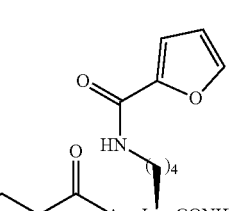<br>CbzHN-Gln-Thr—NH—...—Arg-Lys-CONH$_2$ | NT |
| 51 | A7-GABA (SEQ ID NO: 42) | 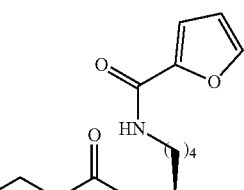<br>CbzHN-Gln-Thr—NH—...—Arg-Lys-CONH$_2$ | NT |
| 52 | T6-V (SEQ ID NO: 43) | 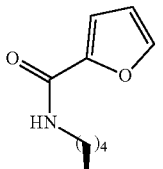<br>CbzHN-Gln-Val-Ala-Arg-Lys-CONH$_2$ | NT |
| 53 | T6-A (SEQ ID NO: 43) | 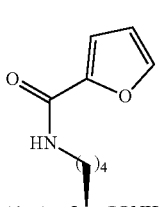<br>CbzHN-Gln-Ala-Ala-Arg-Lys-CONH$_2$ | 0.72 on AF9 |

TABLE 2-continued
| Compound No. | Alternative names | Structure | Activity (IC$_{50}$, μM) |
|---|---|---|---|
| 54 | T6-L (SEQ ID NO: 43) | 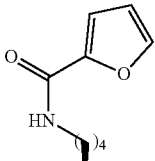 CbzHN-Gln-Leu-Ala-Arg-Lys-CONH$_2$ | NT |
| 55 | T6-S (SEQ ID NO: 43) | 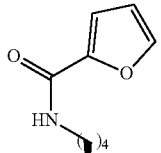 CbzHN-Gln-Ser-Ala-Arg-Lys-CONH$_2$ | 0.78 on AF9 |
| 56 | T6-HoF (SEQ ID NO: 43) | 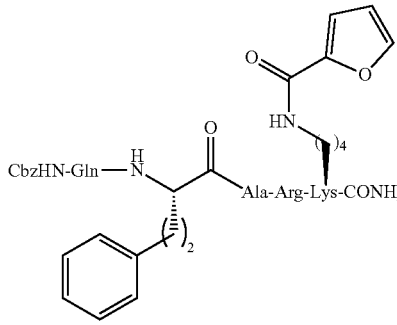 | NT |
| 57 | TA-GABA | 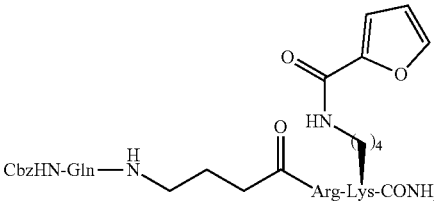 | NT |
| 58 | TA-AMC | 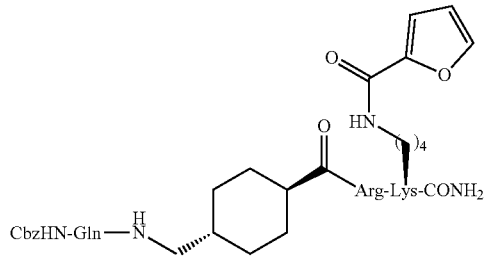 | NT |
| 59 | TA-Ava | 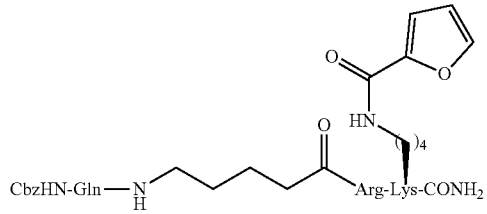 | NT |

TABLE 2-continued

| Compound No. | Alternative names | Structure | Activity (IC$_{50}$, μM) |
|---|---|---|---|
| 60 | TA-Ahx | 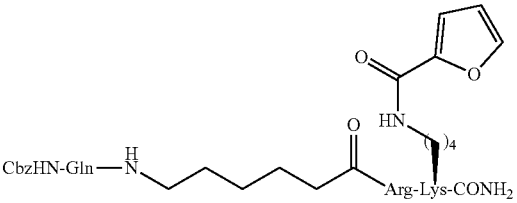 CbzHN-Gln-NH-(CH$_2$)$_5$-C(O)-[furan-2-carboxamide-(CH$_2$)$_4$]-Arg-Lys-CONH$_2$ | NT |
| 61 | TA-1 | 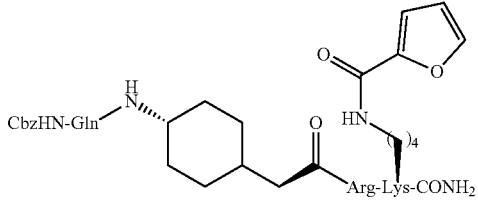 CbzHN-Gln-NH-cyclohexyl-CH$_2$-C(O)-[furan-2-carboxamide-(CH$_2$)$_4$]-Arg-Lys-CONH$_2$ | NT |
| 62 | TA-2 | 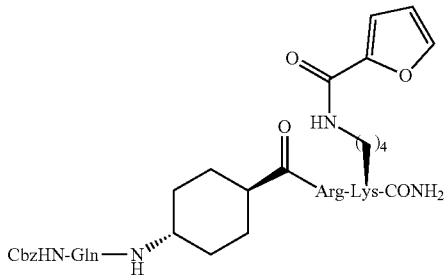 CbzHN-Gln-NH-cyclohexyl-C(O)-[furan-2-carboxamide-(CH$_2$)$_4$]-Arg-Lys-CONH$_2$ | NT |
| 63 | Q5-E (SEQ ID NO: 44) | 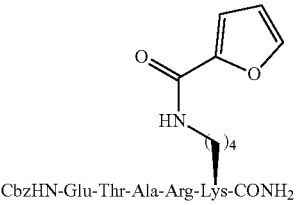 CbzHN-Glu-Thr-Ala-Arg-Lys-CONH$_2$ | NT |
| 64 | Q5-A (SEQ ID NO: 44) | 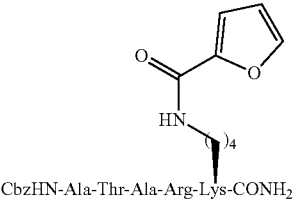 CbzHN-Ala-Thr-Ala-Arg-Lys-CONH$_2$ | NT |
| 65 | Q5-N (SEQ ID NO: 44) | 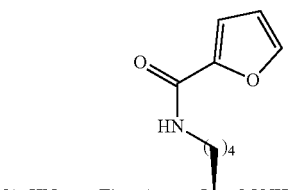 CbzHN-Asn-Thr-Ala-Arg-Lys-CONH$_2$ | NT |
| 66 | Q5-E(OCH$_2$Ph) (SEQ ID NO: 45) | 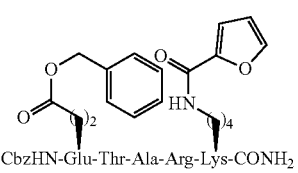 CbzHN-Glu-Thr-Ala-Arg-Lys-CONH$_2$ | NT |

TABLE 2-continued

| Compound No. | Alternative names | Structure | Activity (IC$_{50}$, μM) |
|---|---|---|---|
| 67 | Q5-D(OCH$_2$Ph) (SEQ ID NO: 45) | CbzHN-Glu-Thr-Ala-Arg-Lys-CONH$_2$ | NT |
| 68 | Q5-E(NHPh) (SEQ ID NO: 45) | CbzHN-Glu-Thr-Ala-Arg-Lys-CONH$_2$ | NT |
| 69 | Q5-D(NHPh) (SEQ ID NO: 45) | CbzHN-Glu-Thr-Ala-Arg-Lys-CONH$_2$ | NT |
| 70 | Q5-βQ (SEQ ID NO: 44) | CbzHN...Thr-Ala-Arg-Lys-CONH$_2$ | NT |
| 71 | Cbz-1 (SEQ ID NO: 46) | NH-Gln-Thr-Ala-Arg-Lys-CONH$_2$ | NT |
| 72 | Cbz-2 (SEQ ID NO: 46) | NH-Gln-Thr-Ala-Arg-Lys-CONH$_2$ | NT |
| 73 | Cbz-3 (SEQ ID NO: 46) | NH-Gln-Thr-Ala-Arg-Lys-CONH$_2$ | NT |

TABLE 2-continued
| Compound No. | Alternative names | Structure | Activity (IC$_{50}$, μM) |
|---|---|---|---|
| 74 | Cbz-4 (SEQ ID NO: 46) | 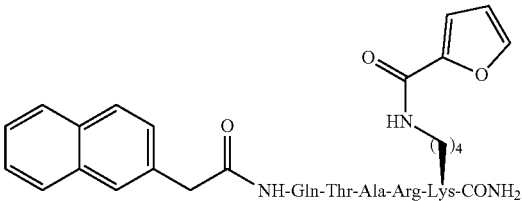 | 0.23 on AF9 |
| 75 | CbzQ-1 (SEQ ID NO: 47) | 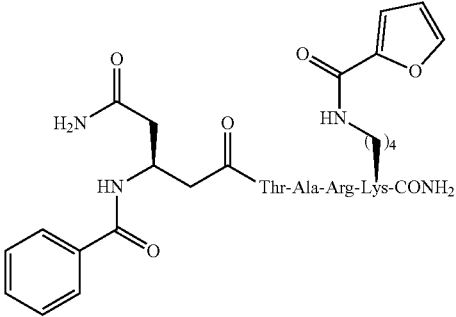 | NT |
| 76 | CbzQ-2 (SEQ ID NO: 47) | 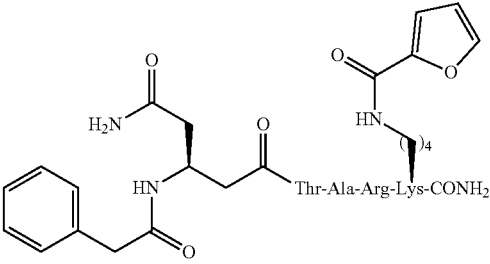 | NT |
| 77 | CbzQ-3 (SEQ ID NO: 47) | 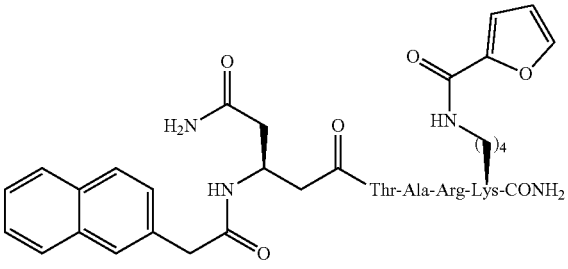 | NT |
| 78 | Cyclic 1 | 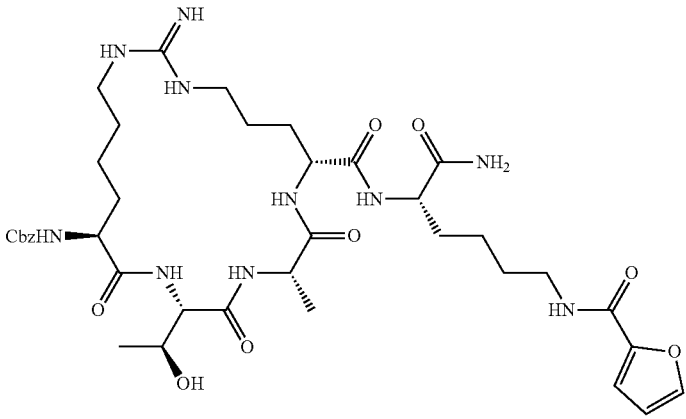 [SMILES: C[C@@H]1NC(=O)[C@H]([C@H](C)O)NC(=O)[C@@H](NC(=O)OCc2ccccc2)CCCCNC(=N)NCCC[C@H](C(=O)N[C@@H](CCCCNC(=O)c2ccco2)C(N)=O)NC1=O] | 1.8 on AF9 43.6 on ENL |

TABLE 2-continued
| Compound No. | Alternative names | Structure | Activity (IC$_{50}$, μM) |
|---|---|---|---|
| 79 | Cyclic 2 | 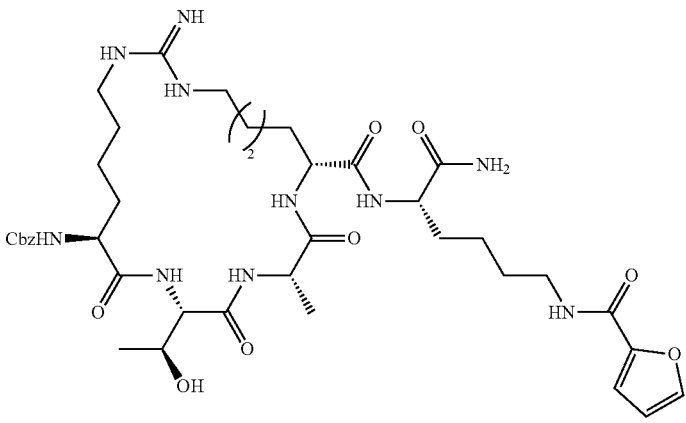 | 2.2 on AF9<br>14.5 on ENL |
| 80 | Cyclic 3 | 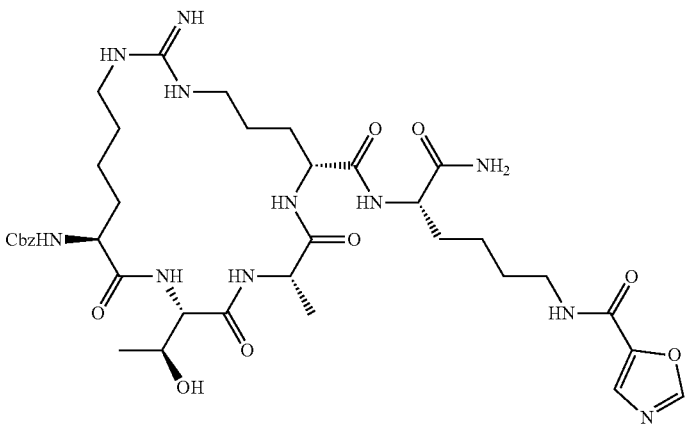 [SMILES: C[C@@H]1NC(=O)[C@H]([C@H](C)O)NC(=O)[C@@H](NC(=O)OCc2ccccc2)CCCCNC(=N)NCCC[C@H](C(=O)N[C@@H](CCCCNC(=O)c2cnco2)C(N)=O)NC1=O] | 0.41 on AF9<br>12.9 on ENL<br>22.7 on YEATS2<br>53.7 on GAS41 |
| 81 | Cyclic 4 | 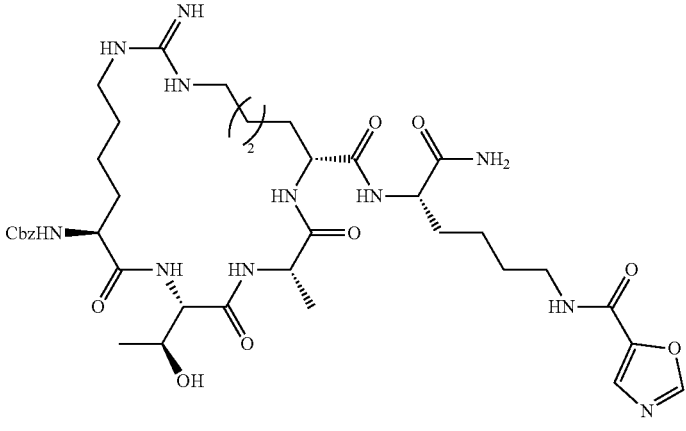 | 0.56 on AF9<br>9.0 on ENL<br>119.6 on YEATS2<br>36.7 on GAS41 |

TABLE 2-continued

| Compound No. | Alternative names | Structure | Activity (IC$_{50}$, μM) |
| --- | --- | --- | --- |
| 82 | Cyclic 5 | 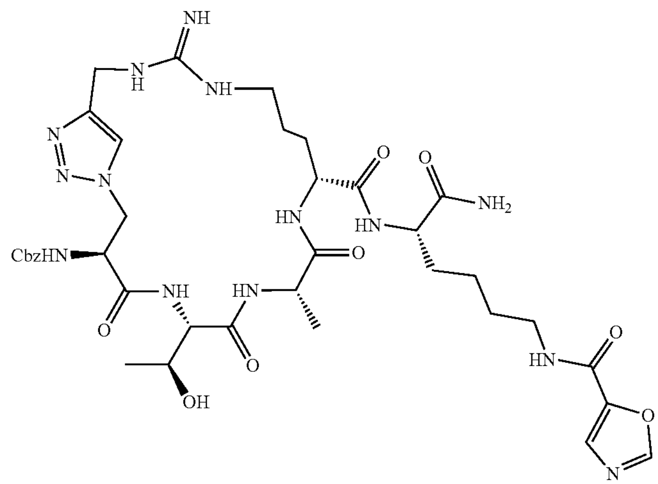 [SMILES: C[C@@H]1NC(=O)[C@H]([C@H](C)O)NC(=O)[C@@H](NC(=O)OCc2ccccc2)Cn2cc(nn2)CNC(=N)NCCC[C@H](C(=O)N[C@@H](CCCCNC(=O)c2cnco2)C(N)=O)NC1=O] | 5.1 on AF9<br>9.23 on ENL |
| 83 | Cyclic 6 | 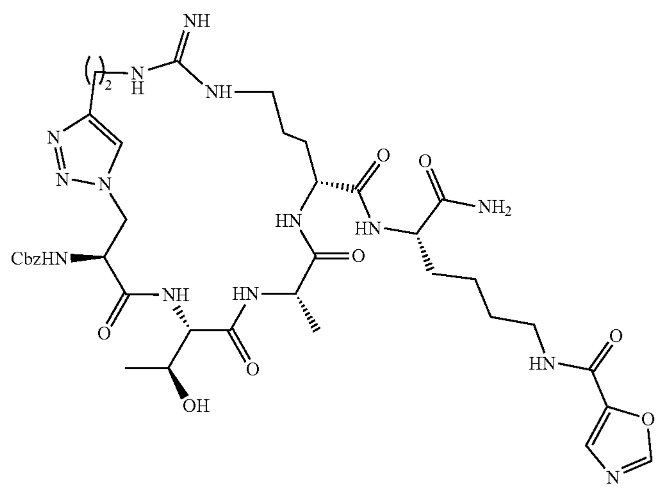 | 2.3 on AF9 |
| 84 | Cyclic 7 | 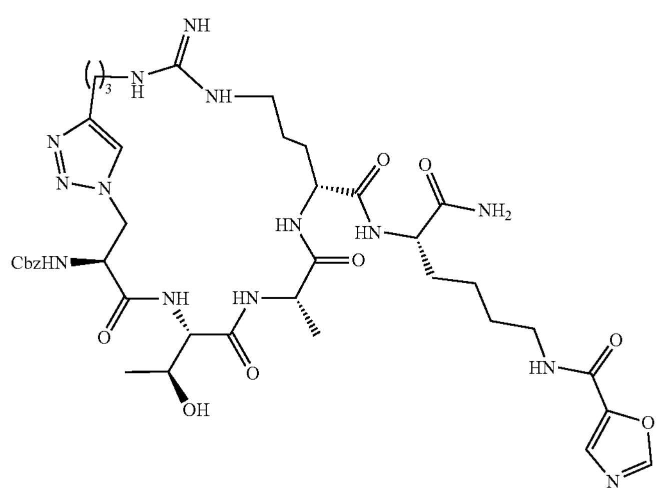 | 2.8 on AF9 |

TABLE 2-continued

| Compound No. | Alternative names | Structure | Activity ($IC_{50}$, μM) |
|---|---|---|---|
| 85 (positive control) | 0, H3K9cr, K9cr (SEQ ID NO: 48) | [structure with crotonyl group] H₂N-Lys-Gln-Thr-Ala-Arg-Lys-Ser-Thr-Gly-Gly-CONH₂ | 6.0 on AF9 52.7 on ENL |
| 86 (negative control) | 17, 4.17, XL-17 (SEQ ID NO: 49) | [structure with cyclopentane carbonyl] H₂N-Lys-Gln-Thr-Ala-Arg-Lys-Ser-Thr-Gly-Gly-CONH₂ | 34.5 on AF9 |

Example 4. Activity Estimation by Isothermal Titration Calorimetry (ITC)

Figure 27A:
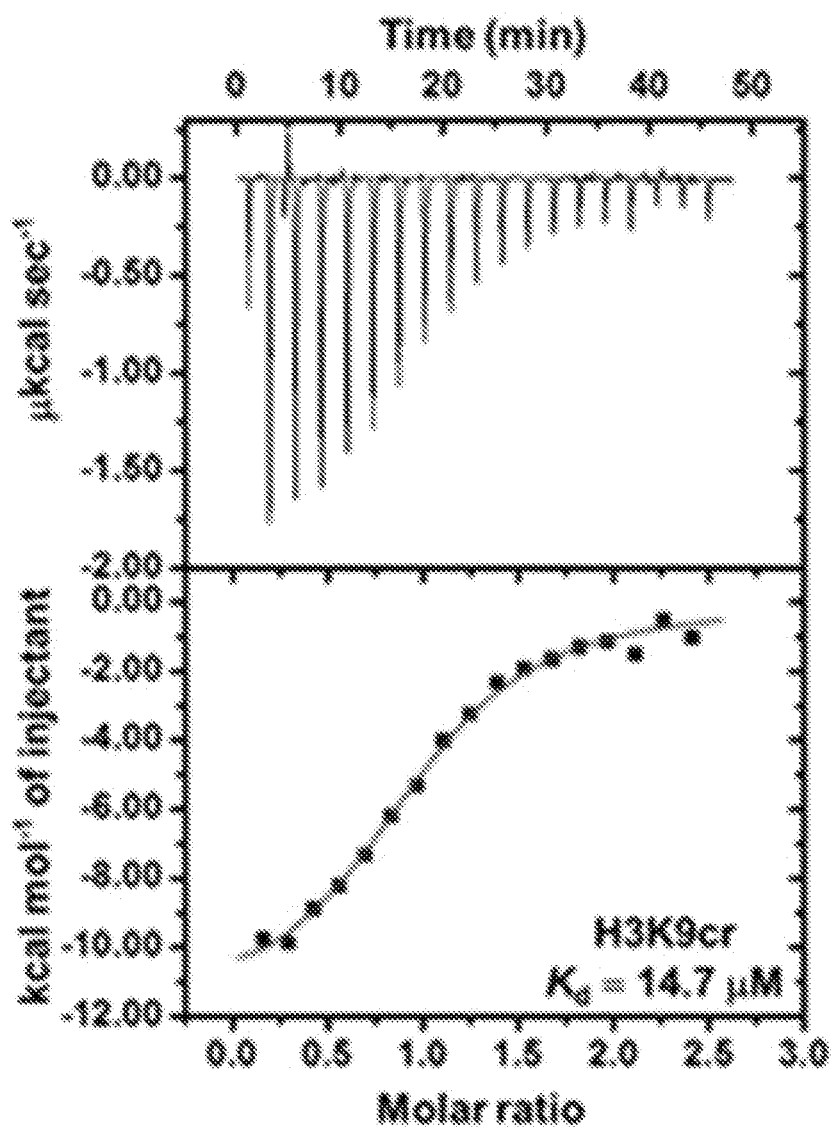
FIGS. 27A-27C are graphs showing the results of isothermal titration calorimetry (ITC) for (27A) the native crotonyl group; (27B) 2-furancarbonyl; and (27C) 5-oxazolecarbonyl.
Figure 27B:
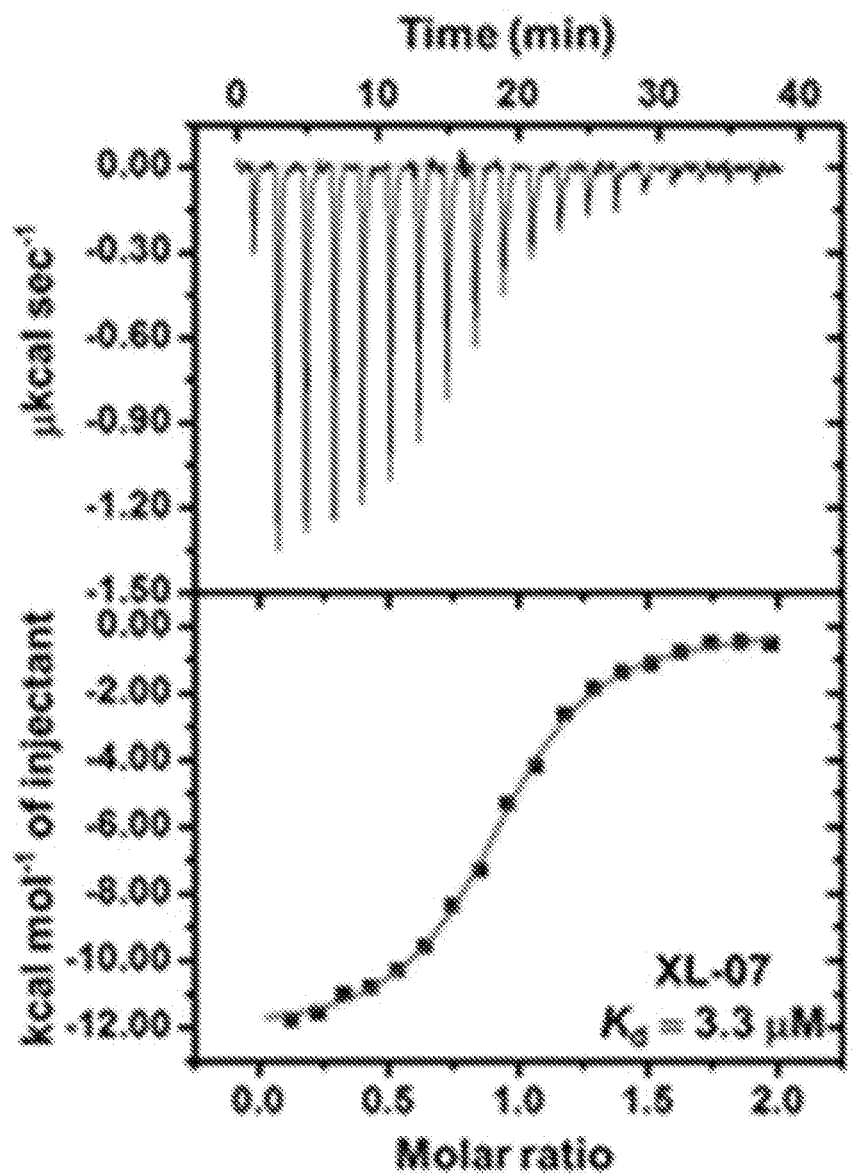
Figure 27C:
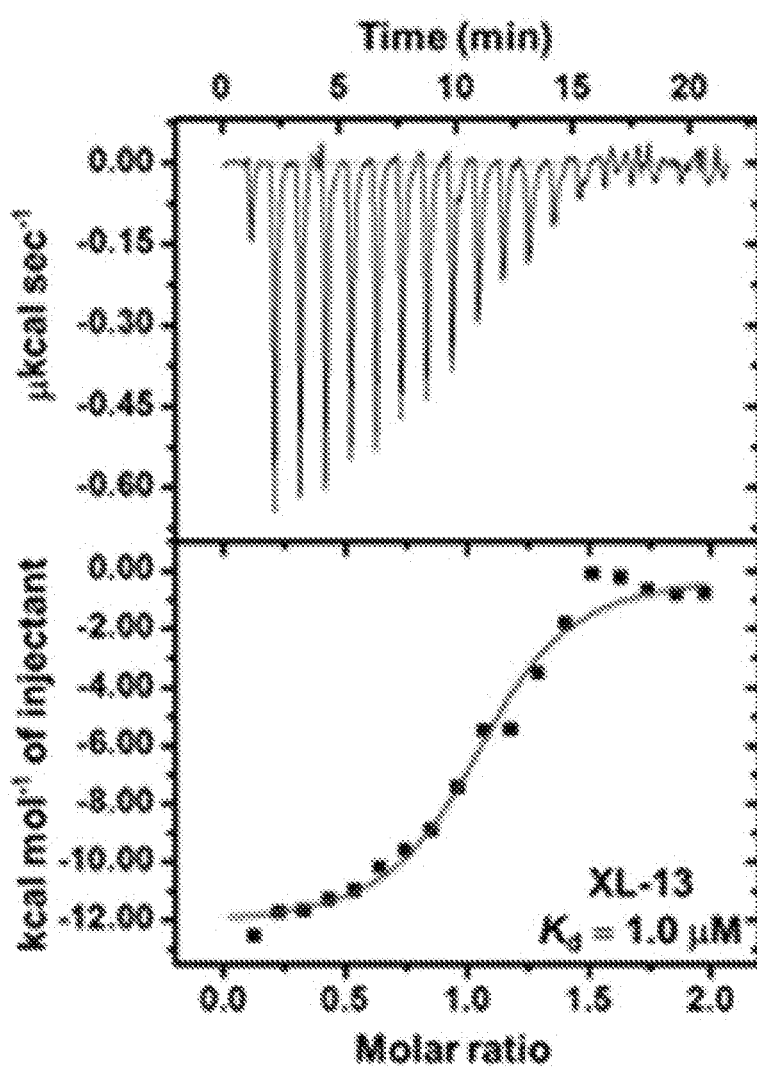

To further validate the reliability of the results obtained from the photo-cross-linking-based competition assay, we performed isothermal titration calorimetry (ITC) to determine the direct binding affinities of the inhibitors toward the AF9 YEATS domain. The acquired dissociation constants showed that the replacement of the native crotonyl group ($K_d$=14.8 μM) by 2-furancarbonyl (XL-07, $K_d$=3.3 μM) and 5-oxazolecarbonyl (XL-13, $K_d$=1.0 μM) led to 4.5- and 14.8-fold binding enhancement, respectively (FIGS. 27A-C and Table 3). The ITC measurements were in agreement with the $IC_{50}$ data, indicating the reliability of the results obtained from the photo-cross-linking-based competition assay.

TABLE 3

| Compound | $K_d$ (μM) | ΔH (cal/mol) | ΔS (cal/mol/deg) | N (sites) |
|---|---|---|---|---|
| H3K9cr | 14.7 | −11920 ± 423 | −17.8 | 0.96 ± 0.02 |
| XL-07 | 3.3 | −12230 ± 110 | −15.9 | 0.91 ± 0.01 |
| XL-13 | 1.0 | −12290 ± 376 | −13.8 | 1.04 ± 0.02 |

The compound Cyclic 3 was also tested with AF9 and ENL YEATS domains. Summary of the thermodynamic parameters of AF9 and ENL YEATS domains with compound Cyclic 3 is shown in Table 4.

TABLE 4

| Protein | Inhibitor | $K_d$ (μM) | ΔH (Kcal/mol) | ΔS (cal/mol/deg) | ΔG (Kcal/mol) |
|---|---|---|---|---|---|
| ENL | Cyclic 3 | 11.4 | −7.06 | −1.05 | −6.72 |
| AF9 | Cyclic 3 | 0.52 | −12.69 | −13.77 | −8.54 |

Example 5. Analysis of Competitors by Mass Spectrometry

LC-MS analysis of competitor control revealed a mass to charge ratio (m/z) of 830.43 (M+H⁺), calculated m/z 830.41 (M+H⁺). LC-MS analysis of competitor R8-K revealed a m/z 824.47 (M+Na⁺), calculated m/z 824.39 (M+Na⁺); m/z 802.40 (M+H⁺), calculated m/z 802.40 (M+H⁺); m/z 401.67 (M+2H⁺), calculated m/z 401.70 (M+2H⁺). LC-MS analysis of competitor R8-cit revealed a m/z 831.30 (M+H⁺), calculated m/z 831.39. LC-MS analysis of competitor R8-Q revealed a m/z 802.24 (M+H⁺), calculated m/z 802.37 (M+H⁺). LC-MS analysis of competitor A7-G revealed a m/z 816.47 (M+H⁺), calculated m/z 816.39 (M+H⁺); m/z 408.67 (M+2H⁺), calculated m/z 408.70 (M+2H⁺).

LC-MS analysis of competitor A7-L revealed a m/z 872.50 (M+H⁺), calculated m/z 872.45 (M+H⁺); m/z 436.80 (M+2H⁺), calculated m/z 437.23 (M+2H⁺). LC-MS analysis of competitor A7-F revealed a m/z 906.50 (M+H⁺), calculated m/z 906.44 (M+H⁺); m/z 453.77 (M+2H⁺), calculated m/z 453.72 (M+2H⁺). LC-MS analysis of competitor A7-W revealed a m/z 945.63 (M+H⁺), calculated m/z 945.45 (M+H⁺). LC-MS analysis of competitor A7-8 Ala revealed a m/z 830.50 (M+H⁺), calculated m/z 830.41 (M+H⁺). LC-MS analysis of competitor A7-GABA revealed a m/z 844.51 (M+H⁺), calculated m/z 844.44 (M+H⁺). LC-MS analysis of competitor T6-V revealed a m/z 828.48 (M+H⁺), calculated m/z 828.43 (M+H⁺); m/z 414.80 (M+2H⁺), calculated m/z 414.74 (M+2H⁺).

LC-MS analysis of competitor T6-A revealed a m/z 800.47 (M+H⁺), calculated m/z 800.40 (M+H⁺); m/z 400.67 (M+2H⁺), calculated m/z 400.70 (M+2H⁺). LC-MS analysis of competitor T6-L revealed a m/z 842.49 (M+H⁺), calculated m/z 842.44 (M+H⁺); m/z 421.79 (M+2H⁺), calculated m/z 421.90 (M+2H⁺). LC-MS analysis of competitor T6-S revealed a m/z 816.47 (M+H⁺), calculated m/z 816.39 (M+H⁺); m/z 408.67 (M+2H⁺), calculated m/z 408.70 (M+2H⁺). LC-MS analysis of competitor Q5-E revealed a m/z 831.47 (M+H⁺), calculated m/z 831.90 (M+H⁺); m/z 416.13 (M+2H⁺), calculated m/z 416.45 (M+2H⁺). LC-MS analysis of competitor Cbz-1 revealed a m/z 800.47 (M+H⁺), calculated m/z 800.40 (M+H⁺). LC-MS analysis of competitor Cbz-2 revealed a m/z 814.49 (M+H⁺), calculated m/z 814.41 (M+H⁺). LC-MS analysis of competitor Cbz-3 revealed a m/z 828.47 (M+H⁺), calculated m/z 828.43 (M+H⁺); m/z 414.67 (M+2H⁺), calculated m/z 414.72 (M+2H⁺).

LC-MS analysis of competitor Cbz-4 revealed a m/z 864.53 (M+H⁺), calculated m/z 864.43 (M+H⁺). LC-MS analysis of competitor Control-COOH revealed a m/z 831.41 (M+H⁺), calculated m/z 831.39 (M+H⁺). LC-MS analysis of competitor TA-GABA revealed a m/z 743.41 (M+H⁺), calculated m/z 743.38 (M+H⁺). LC-MS analysis of competitor TA-AMC revealed a m/z 797.48 (M+H⁺), calculated m/z 797.42 (M+H⁺). LC-MS analysis of competitor TA-Ava revealed a m/z 757.41 (M+H⁺), calculated m/z 757.39 (M+H⁺). LC-MS analysis of competitor TA-Ahx revealed a m/z 771.44 (M+H⁺), calculated m/z 771.41 (M+H⁺). LC-MS analysis of competitor Q5-A revealed a m/z 773.43 (M+H⁺), calculated m/z 773.39 (M+H⁺). LC-MS analysis of competitor Q5-N revealed a m/z 816.42 (M+H⁺), calculated m/z 816.39 (M+H⁺).

LC-MS analysis of competitor Q5-E(OCH2Ph) revealed a m/z 921.48 (M+H⁺), calculated m/z 921.44 (M+H⁺). LC-MS analysis of competitor Q5-D(OCH2Ph) revealed a m/z 907.46 (M+H⁺), calculated m/z 907.42 (M+H⁺). LC-MS analysis of competitor Q5-PQ revealed a m/z 830.45 (M+H⁺), calculated m/z 830.41 (M+H⁺). LC-MS analysis of competitor CbzQ-1 revealed a m/z 800.41 (M+H⁺), calculated m/z 800.40 (M+H⁺). LC-MS analysis of competitor CbzQ-2 revealed a m/z 814.44 (M+H⁺), calculated m/z 814.41 (M+H⁺). LC-MS analysis of competitor CbzQ-3 revealed a m/z 864.45 (M+H⁺), calculated m/z 864.43 (M+H⁺). LC-MS analysis of competitor TA-1 revealed a m/z 797.49 (M+H⁺), calculated m/z 797.42 (M+H⁺). LC-MS analysis of competitor TA-2 revealed a m/z 783.45 (M+H⁺), calculated m/z 783.90 (M+H⁺). LC-MS analysis of competitor T6-HoF revealed a m/z 890.52 (M+H⁺), calculated m/z 890.44 (M+H⁺). LC-MS analysis of competitor Q5-E (NHPh) revealed a m/z 906.51 (M+H⁺), calculated 5 m/z 906.44 (M+H⁺). LC-MS analysis of competitor Q5-D (NHPh) revealed a m/z 892.51 (M+H⁺), calculated m/z 892.42 (M+H⁺).

Example 6. Fine-Tuning the Inhibitor Activity

We next sought to find the optimal sequence for AF9 YEATS inhibition. In the AF9 YEATS-H3K9cr complex, the $R^8$ residue forms a charge-stabilized hydrogen bond with D103 of AF9, which provides another key contact in the recognition besides π-π-π stacking. To examine the contribution of the flanking residues to YEATS inhibition, we extracted the RK signature motif of inhibitor XL-07, and then added the other residues back one by one, generating another 9 inhibitors (XL-07a to XL-07i, see structures below and Table 5) with different lengths in their sequences from the original K4-G13 decamer.

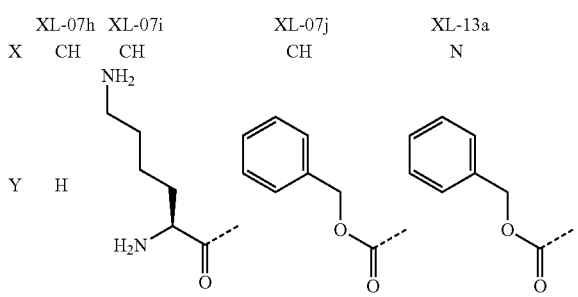

TABLE 5

| Compound | Structure |
| --- | --- |
| XL-07a | H₂N-Arg-Lys-CONH₂ |
| XL-07b | H₂N-Arg-Lys-Ser-CONH₂ |
| XL-07c (SEQ ID NO: 32) | H₂N-Arg-Lys-Ser-Thr-CONH₂ |
| XL-07d | H₂N-Ala-Arg-Lys-CONH₂ |
| XL-07e (amino acids 1-4 of SEQ ID NO: 33) | H₂N-Ala-Arg-Lys-Ser-CONH₂ |

TABLE 5-continued

| Compound | Structure |
|---|---|
| XL-07f (SEQ ID NO: 33) | H₂N-Ala-Arg-Lys-Ser-Thr-CONH₂ |
| XL-07g (amino acids 3-6 of SEQ ID NO: 34) | H₂N-Thr-Ala-Arg-Lys-CONH₂ |
| XL-07h (amino acids 2-6 of SEQ ID NO: 34) | H₂N-Gln-Thr-Ala-Arg-Lys-CONH₂ |
| XL-07i (SEQ ID NO: 34) | H₂N-Lys-Gln-Thr-Ala-Arg-Lys-CONH₂ |
| XL-07j (SEQ ID NO: 35) | CbzHN-Gln-Thr-Ala-Arg-Lys-CONH₂ |
| XL-13a (SEQ ID NO: 36) | CbzHN-Gln-Thr-Ala-Arg-Lys-CONH₂ |

A rough screening revealed that the residues at the C-terminal side of the RK motif were not necessary to the binding between the inhibitors and the AF9 YEATS domain. Instead, the presence of these residues negatively impacted the inhibitory activity. The accumulation of the residues at the N-terminal side of the RK motif gradually regained the activity. It was not until the addition of the residues reached a pentamer with QTARK in the sequence that the inhibitor XL-07h exhibited a comparable activity as XL-07 (IC$_{50}$=4.5 μM, FIGS. 18 and 29). The attachment of the N-terminal-most K residue (structure XL-07i above) significantly increased the binding affinity (IC$_{50}$=0.46 μM, FIGS. 19 and 29). As has been suggested by the AF9 YEATS-H3K9cr complex structure, the H3Q5 residue contributes to the interaction by fixing the conformation of the peptide through an intramolecular hydrogen bond with R$^8$. In addition, the methylene chain of the H3K4 residue forms intensive hydrophobic interactions with the residues in the L8 loop of AF9 YEATS. This could explain why the QTARK sequence turned out to be the minimal requirement for maintaining an effective AF9 YEATS inhibition; while the appending of another K residue largely improved the activity. Further structural optimization by substituting the N-terminal K with a hydrophobic carboxybenzyl (Cbz) group (structure XL-07j above), and introducing the 5-oxazolecarbonyl side chain (structure XL-13a above) even strengthened the inhibitory activity (IC$_{50}$ values as 0.26 μM and 0.24 μM, respectively, FIGS. 20 and 21).

Example 7. Adjusting the Inhibitor Selectivity for Other YEATS Domains

Figure 30:
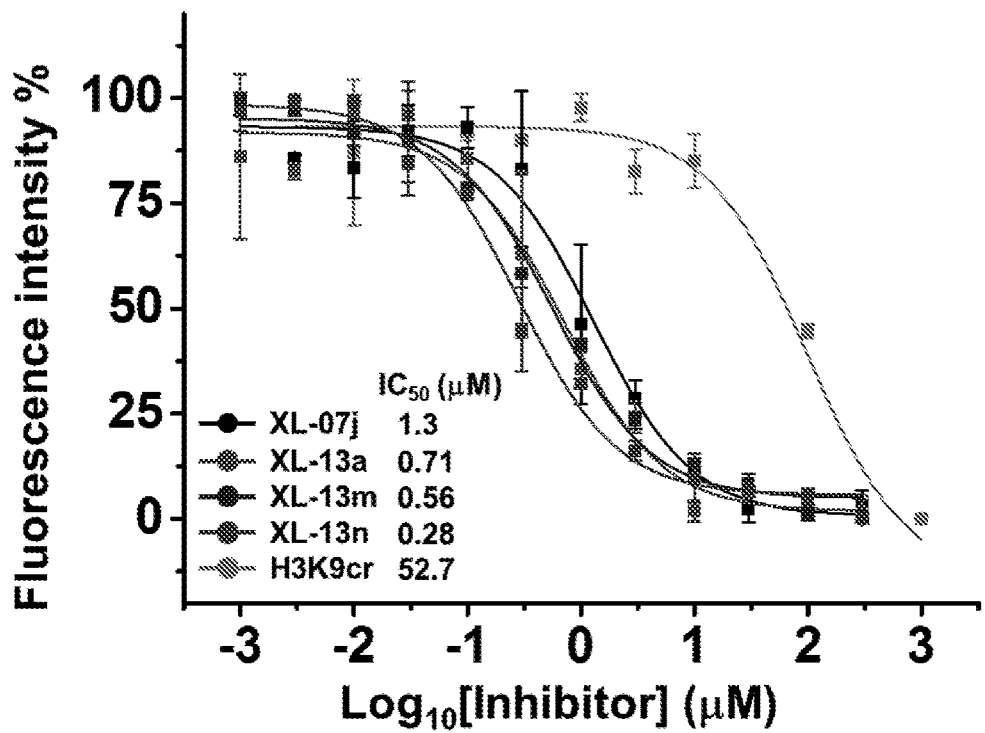
FIG. 30 is a graph showing the effects of concentrations of compounds on the relative fluorescence intensity of probe-labeled protein, leading to determination of $IC_{50}$. A comparison of $IC_{50}$ values of compounds 26 (XL-07j), 27 (XL-13a), 39 (XL-13m), and 40 (XL-13n) to the H3K9cr positive control peptide is shown, based on their interaction with the ENL YEATS domain.
Figure 31:
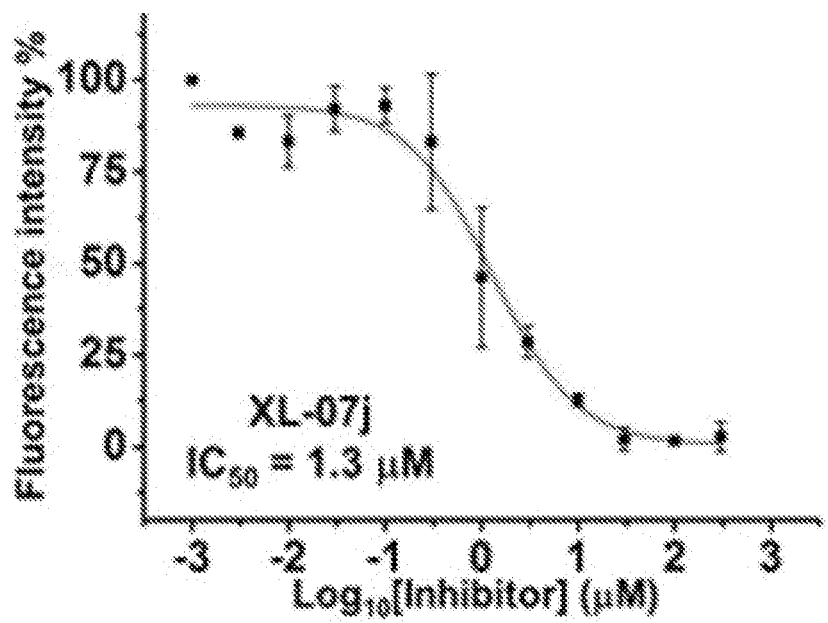
FIG. 31 is a graph showing the effects of compound 26 (XL-07j) inhibitor concentration on the relative fluorescence intensity of probe-labeled protein, leading to determination of $IC_{50}$. This value is based on its interaction with the ENL YEATS domain.
Figure 32:
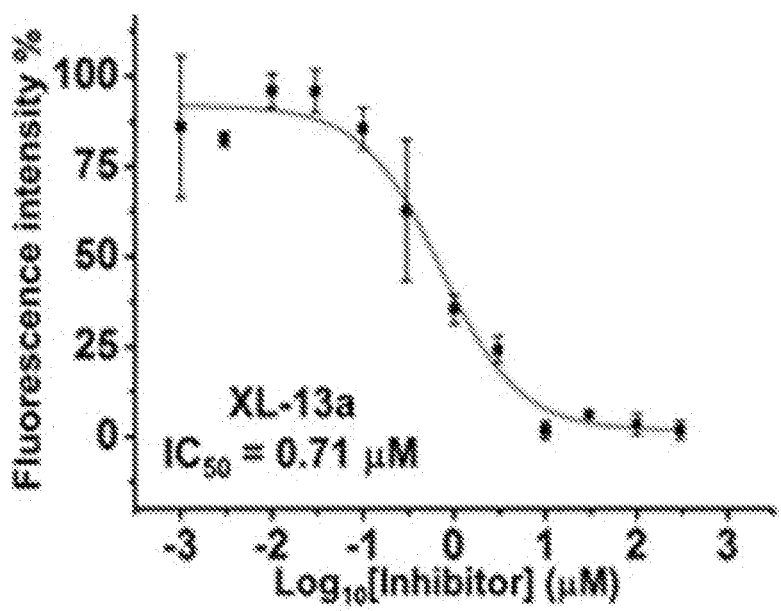
FIG. 32 is a graph showing the effects of compound 27 (XL-13a) inhibitor concentration on the relative fluorescence intensity of probe-labeled protein, leading to determination of $IC_{50}$. This value is based on its interaction with the ENL YEATS domain.
Figure 33:
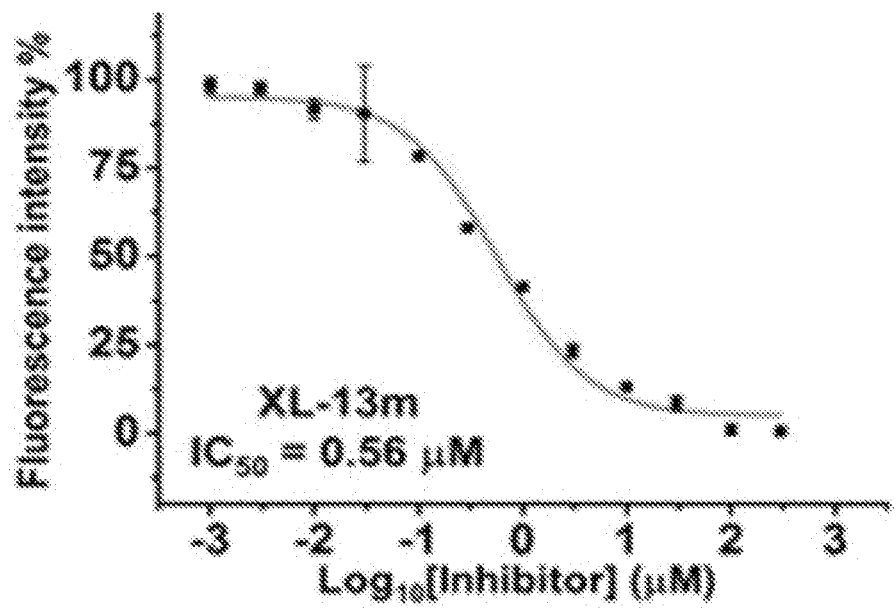
FIG. 33 is a graph showing the effects of compound 39 (XL-13m) inhibitor concentration on the relative fluorescence intensity of probe-labeled protein, leading to determination of $IC_{50}$. This value is based on its interaction with the ENL YEATS domain.
Figure 34:
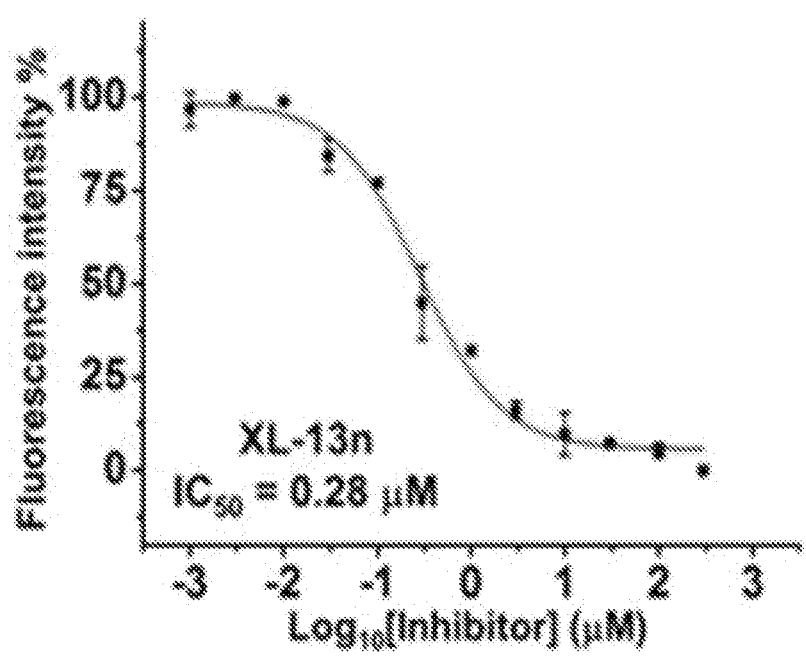
FIG. 34 is a graph showing the effects of compound 40 (XL-13n) inhibitor concentration on the relative fluorescence intensity of probe-labeled protein, leading to determination of $IC_{50}$. This value is based on its interaction with the ENL YEATS domain.
Figure 35:
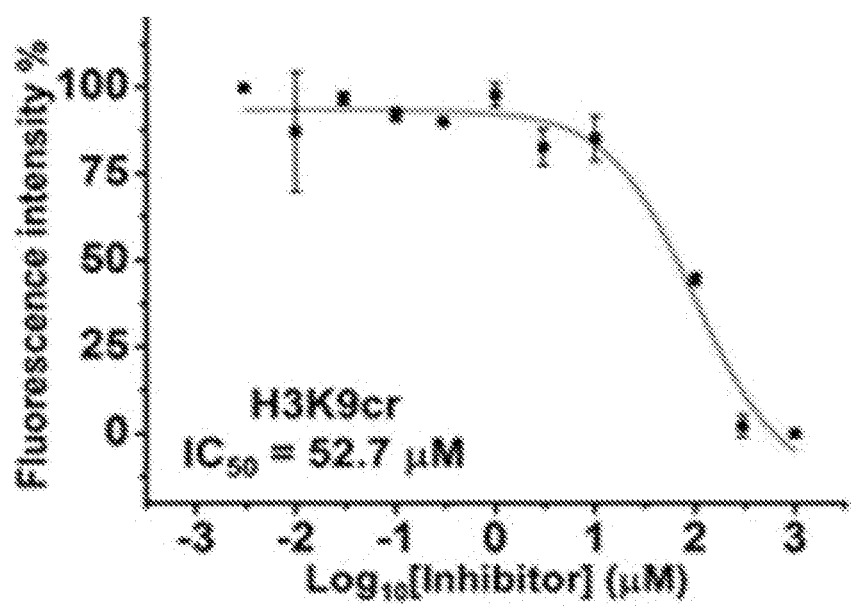
FIG. 35 is a graph showing the effects of H3K9cr peptide (positive control) concentration on the relative fluorescence intensity of probe-labeled protein, leading to determination of $IC_{50}$. This value is based on its interaction with the ENL YEATS domain.

We next asked if the inhibitors could target the other YEATS domains. Competition assays against the ENL YEATS domain showed that the two most potent compounds, XL-07j and XL-13a, inhibited ENL with IC$_{50}$ values of 1.3 μM and 0.71 μM, respectively (FIGS. 30-32). Given the high similarity between AF9 and ENL, it was predictable that the AF9-active inhibitors could intimately interact with ENL as well. However, it was also interesting to learn that, compared to AF9, XL-07j and XL-13a exhibited 5- and 2.9-fold activity drops on ENL, respectively. Since the aromatic 'sandwich' cages in AF9 and ENL YEATS domains are almost identical to each other, the activity changes of the inhibitors were therefore likely to come from the differences in the interactions contributed by other flanking residues. This observation inspired us to pursue the possibility that varied sequences could reverse the selectivity of inhibitors over the two YEATS domains. As has been reported, the ENL YEATS domain showed a slightly higher affinity toward acylations on H3K27 than on H3K9; we thus focused on the H3K27 sequence to search for the ENL-selective inhibitors. The 5-oxazolecarbonyl side chain was incorporated at the K27 position, and 14 inhibitors (XL-13b to XL-13o, see structure below and Table 6) were obtained by changing the flanking residues of the RK motif and roughly screening for their activities against ENL as described above.

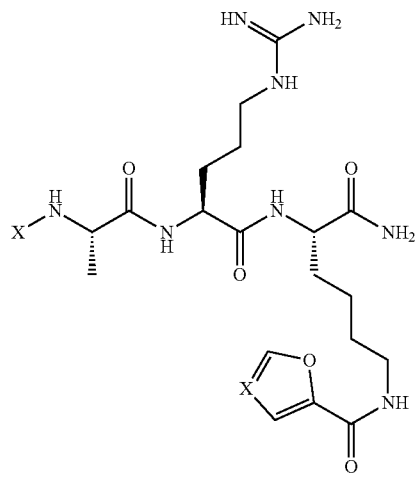

-continued

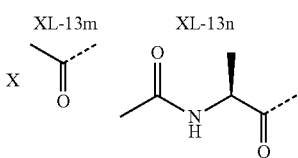

TABLE 6

| Compound | Structure |
|---|---|
| XL-13b (SEQ ID NO: 37) | H₂N-Thr-Lys-Ala-Ala-Arg-Lys-Ser-Ala-Pro-Ala-Thr-CONH₂ |
| XL-13c (amino acids 1-10 of SEQ ID NO: 37) | H₂N-Thr-Lys-Ala-Ala-Arg-Lys-Ser-Ala-Pro-Ala-CONH₂ |
| XL-13d (amino acids 1-9 of SEQ ID NO: 37) | H₂N-Thr-Lys-Ala-Ala-Arg-Lys-Ser-Ala-Pro-CONH₂ |
| XL-13e (amino acids 1-8 of SEQ ID NO: 37) | H₂N-Thr-Lys-Ala-Ala-Arg-Lys-Ser-Ala-CONH₂ |
| XL-13f (amino acids 1-7 of SEQ ID NO: 37) | H₂N-Thr-Lys-Ala-Ala-Arg-Lys-Ser-CONH₂ |
| XL-13g (amino acids 1-6 of SEQ ID NO: 37) | H₂N-Thr-Lys-Ala-Ala-Arg-Lys-CONH₂ |

TABLE 6-continued

| Compound | Structure |
|---|---|
| XL-13h (amino acids 4-10 of SEQ ID NO: 38) | H₂N-Arg-Lys-Ser-Ala-Pro-Ala-Thr-CONH₂ |
| XL-13i (amino acids 3-10 of SEQ ID NO: 38) | H₂N-Ala-Arg-Lys-Ser-Ala-Pro-Ala-Thr-CONH₂ |
| XL-13j (amino acids 2-10 of SEQ ID NO: 38) | H₂N-Ala-Ala-Arg-Lys-Ser-Ala-Pro-Ala-Thr-CONH₂ |
| XL-13k (SEQ ID NO: 38) | H₂N-Lys-Ala-Ala-Arg-Lys-Ser-Ala-Pro-Ala-Thr-CONH₂ |
| XL-13l | AcHN-Arg-Lys-CONH₂ |
| XL-13m | AcHN-Ala-Arg-Lys-CONH₂ |

TABLE 6-continued

| Compound | Structure |
|---|---|
| XL-13n (amino acids 2-5 of SEQ ID NO: 39) | AcHN-Ala-Ala-Arg-Lys-CONH$_2$ |
| XL-13o (SEQ ID NO: 39) | AcHN-Lys-Ala-Ala-Arg-Lys-CONH$_2$ |

Figure 36:
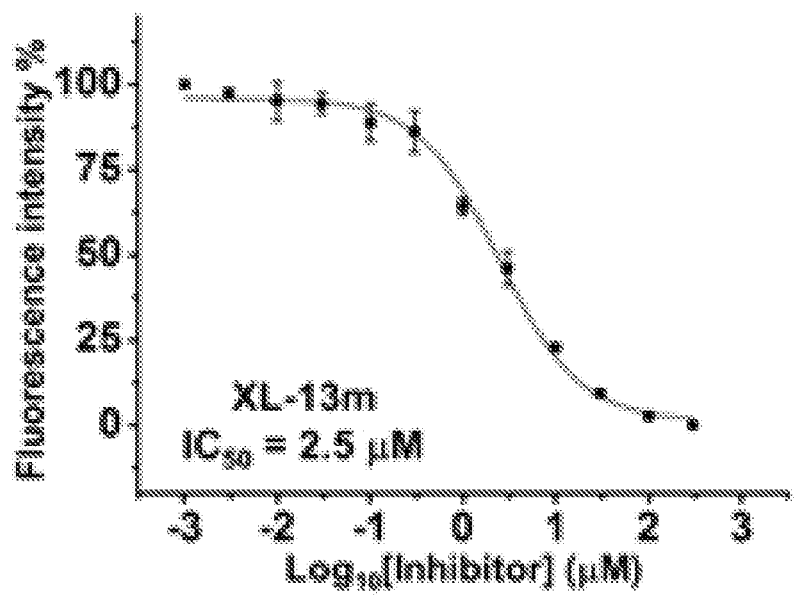
FIG. 36 is a graph showing the effects of compound 39 (XL-13m) concentration on the relative fluorescence intensity of probe-labeled protein, leading to determination of $IC_{50}$. This value is based on its interaction with the AF9 YEATS domain.
Figure 37:
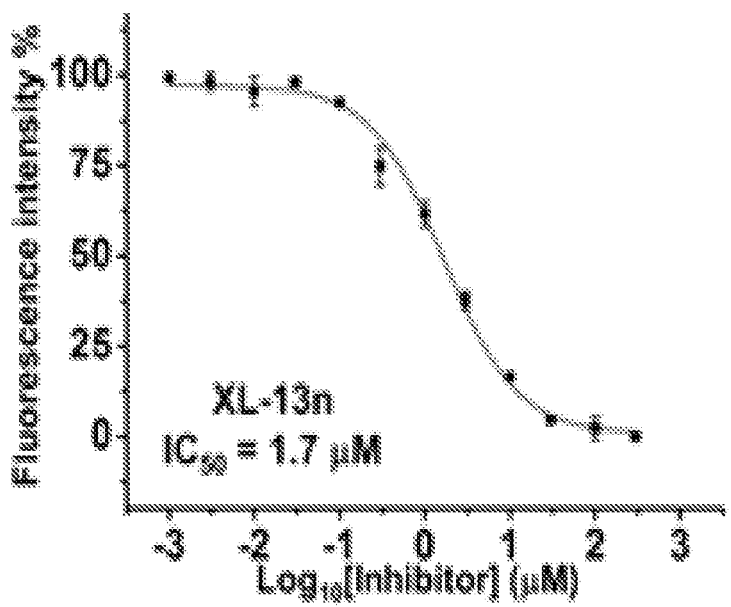
FIG. 37 is a graph showing the effects of compound 40 (XL-13n) concentration on the relative fluorescence intensity of probe-labeled protein, leading to determination of $IC_{50}$. This value is based on its interaction with the AF9 YEATS domain.
Figure 38:
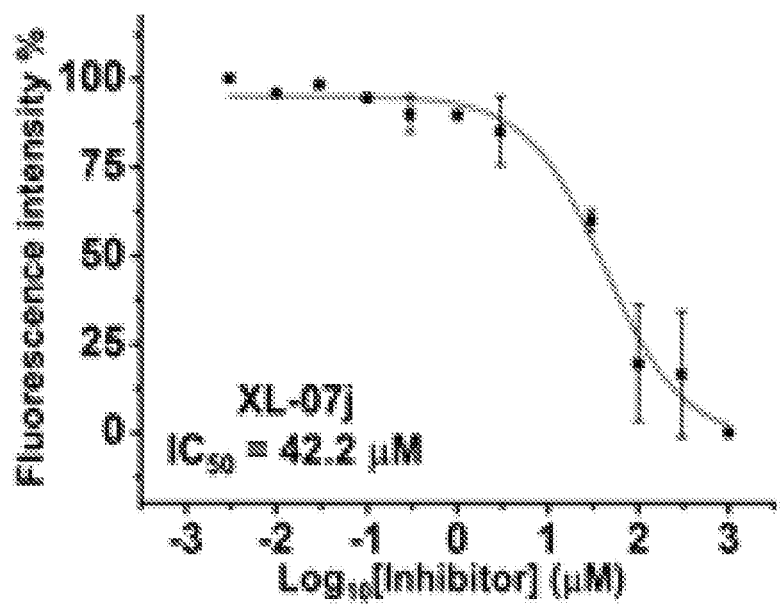
FIG. 38 is a graph showing the effects of compound 26 (XL-07j) concentration on the relative fluorescence intensity of probe-labeled protein, leading to determination of $IC_{50}$. This value is based on its interaction with the YEATS2 domain.
Figure 39:
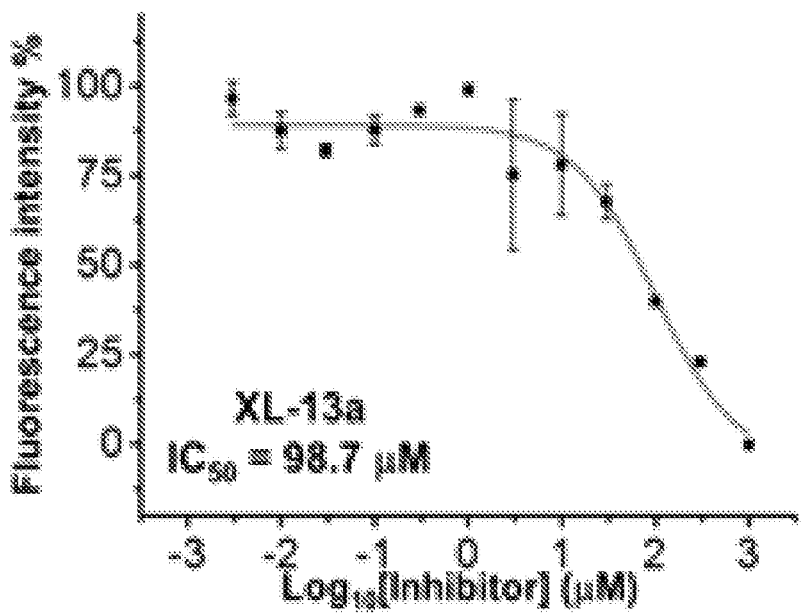
FIG. 39 is a graph showing the effects of compound 27 (XL-13a) concentration on the relative fluorescence intensity of probe-labeled protein, leading to determination of $IC_{50}$. This value is based on its interaction with the YEATS2 domain.
Figure 40:
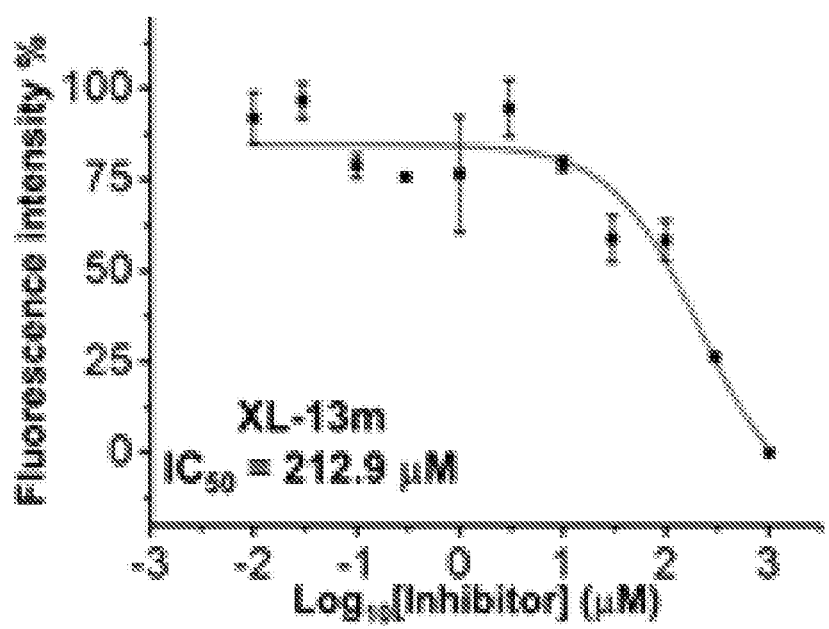
FIG. 40 is a graph showing the effects of compound 39 (XL-13m) concentration on the relative fluorescence intensity of probe-labeled protein, leading to determination of $IC_{50}$. This value is based on its interaction with the YEATS2 domain.
Figure 41:
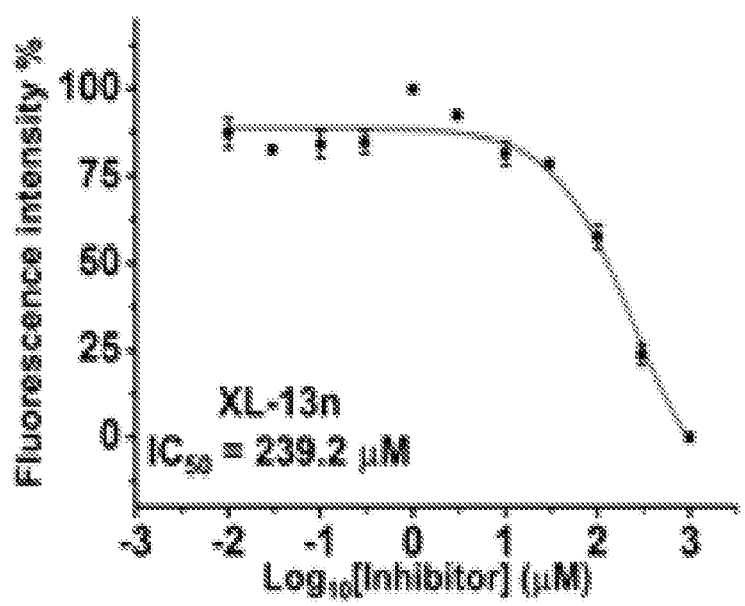
FIG. 41 is a graph showing the effects of compound 40 (XL-13n) concentration on the relative fluorescence intensity of probe-labeled protein, leading to determination of $IC_{50}$. This value is based on its interaction with the YEATS2 domain.
Figure 42:
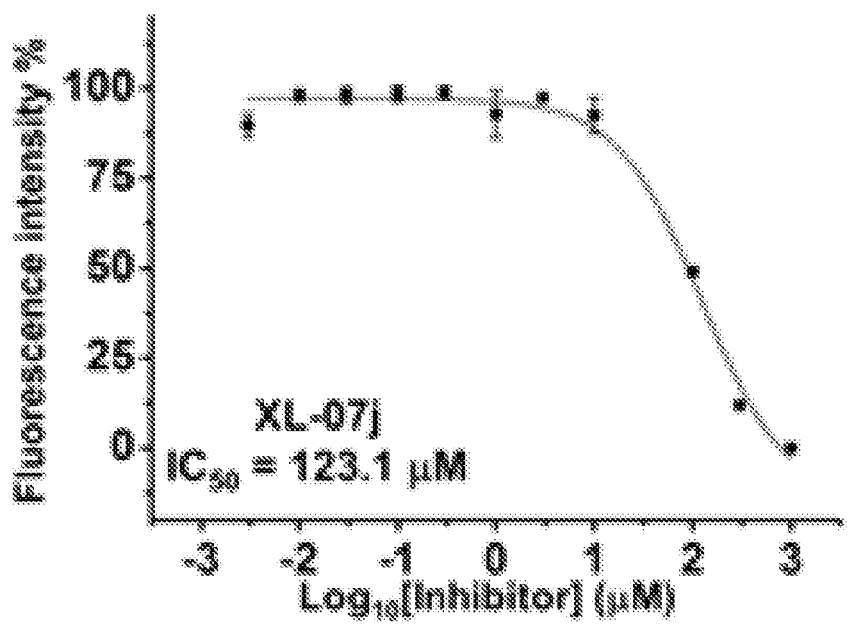
FIG. 42 is a graph showing the effects of compound 26 (XL-07j) concentration on the relative fluorescence intensity of probe-labeled protein, leading to determination of $IC_{50}$. This value is based on its interaction with the GAS41 YEATS domain.
Figure 43:
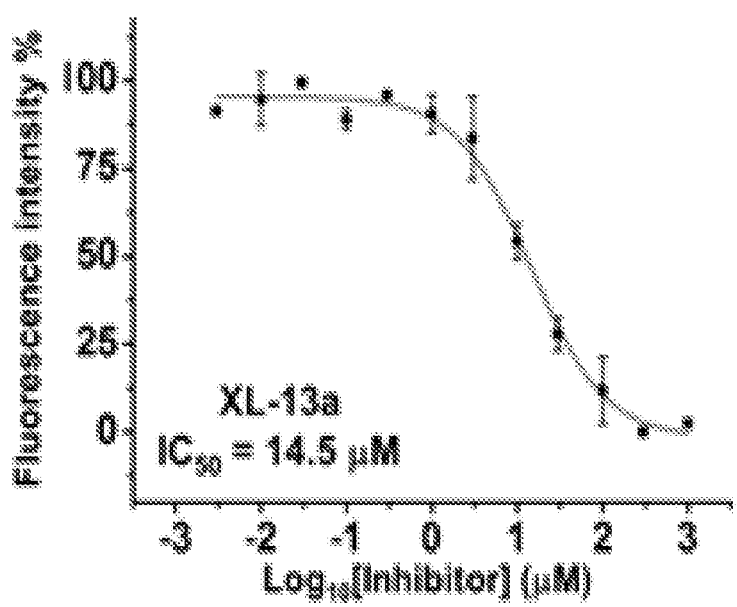
FIG. 43 is a graph showing the effects of compound 27 (XL-13a) concentration on the relative fluorescence intensity of probe-labeled protein, leading to determination of $IC_{50}$. This value is based on its interaction with the GAS41 YEATS domain.
Figure 44:
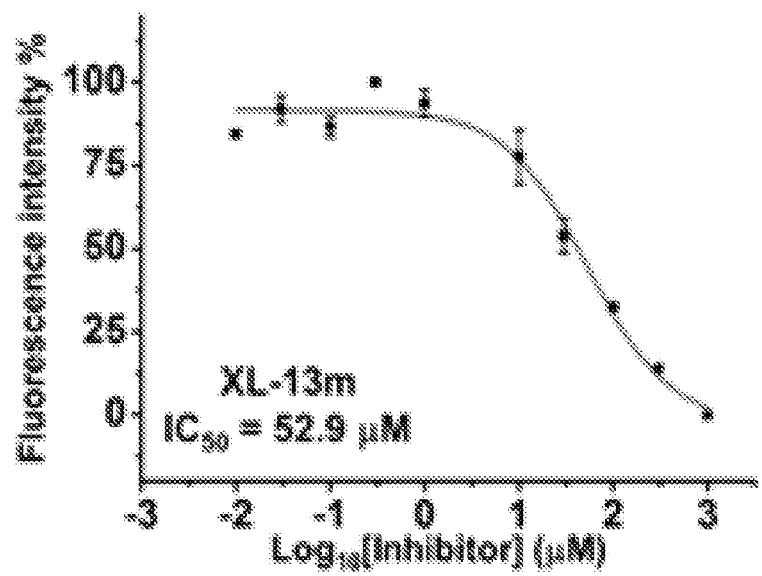
FIG. 44 is a graph showing the effects of compound 39 (XL-13m) concentration on the relative fluorescence intensity of probe-labeled protein, leading to determination of $IC_{50}$. This value is based on its interaction with the GAS41 YEATS domain.
Figure 45:
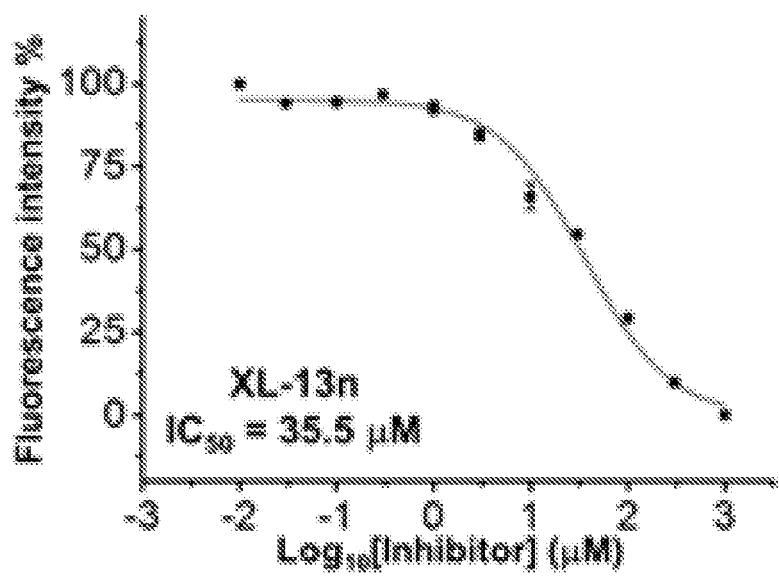
FIG. 45 is a graph showing the effects of compound 40 (XL-13n) concentration on the relative fluorescence intensity of probe-labeled protein, leading to determination of $IC_{50}$. This value is based on its interaction with the GAS41 YEATS domain.

Similarly, the residues at the C-terminal side of the RK motif were unwanted for ENL inhibition; whereas the addition and removal of the residues at the N-terminal side showed slight effects on the inhibitory activities. Photo-cross-linking-based competition showed that a trimer (structure XL-13m above) and a tetramer (structure XL-13n above) inhibited the ENL YEATS domain with IC$_{50}$ values of 0.56 μM, and 0.28 μM, respectively (FIGS. 30, 33, and 34); while their activities on AF9 were 4.5- and 6.1-fold weaker (for XL-13m, IC$_{50}$=2.5 μM; for XL-13n, IC$_{50}$=1.7 μM; FIGS. 36 and 37). The results indicated that the auxiliary roles played by the flanking residues (especially the N-terminal ones) to the RK motif were more important to AF9 YEATS inhibition, while ENL showed fewer requirements. Such differences helped us achieve selectivity between these two YEATS domains, providing the high conservation in their structure.

We further determined the activities of inhibitors XL-07j, XL-13a, XL-13m, and XL-13n on the YEATS domains of YEATS2 and Gas14, which resulted in much weaker activities (Table 7 and FIGS. 38-45). No obvious inhibitions were observed on Kac/Kcr eraser (Sirt3), Kac readers (BrDs of CBP, BAZ2B, and BRD4), and readers of lysine methylation marks (SPIN1 and ING2).

TABLE 7

IC$_{50}$ of YEATS inhibitors on different YEATS domains.

|  | AF9 | ENL | YEATS2 | GAS41 |
|---|---|---|---|---|
| XL-07j | 0.26 μM | 1.3 μM | 42.4 μM | 123.1 μM |
| XL-13a | 0.24 μM | 0.71 μM | 98.7 μM | 14.5 μM |
| XL-13m | 2.5 μM | 0.56 μM | 212.9 μM | 52.9 μM |
| XL-13n | 1.7 μM | 0.28 μM | 239.2 μM | 35.5 μM |

Example 8. Analysis of Compound XL-13m in MOLM13 Cells

We next applied the cellular thermal shift assay (CETSA) to examine if XL-13m was cell permeable and could target ENL in living cells. MOLM-13 (FLAG-ENL) were treated with XL-13m for 12 hours and then heated at different temperature to denature and precipitate proteins. ENL interacted with inhibitors will have better thermal stability and thus be precipitated at higher temperature. Soluble proteins were extracted by freeze-thaw cycle and subjected to western blotting analysis. Using antibody against FLAG-tag and ENL, we detected higher abundancy of soluble ENL proteins in XL-13m treated MOLM-13 cells at higher temperature (55° C., 57° C., 59° C.). We also incubated the inhibitor with another leukemia cell line MV4-11 and obtained the same results, demonstrating that XL-13m could enter cells and target endogenous ENL.

Figure 48:
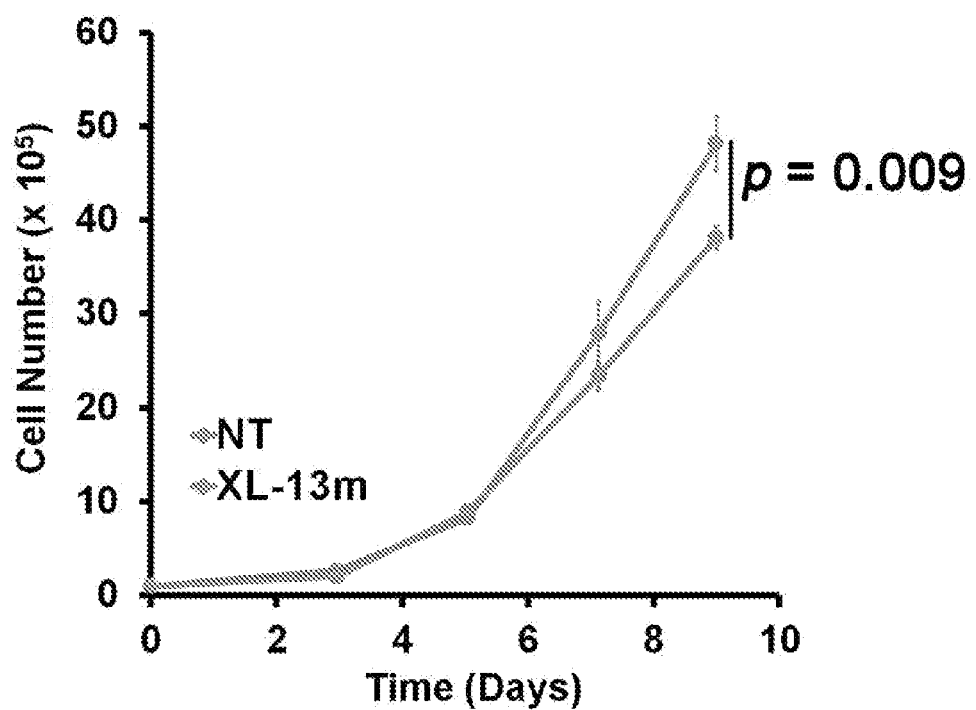
FIG. 48 is a graph showing the effect of compound 39 on cell proliferation. P value by student's t-test. Mean±s.d., three biological replicates.
Figure 49A:
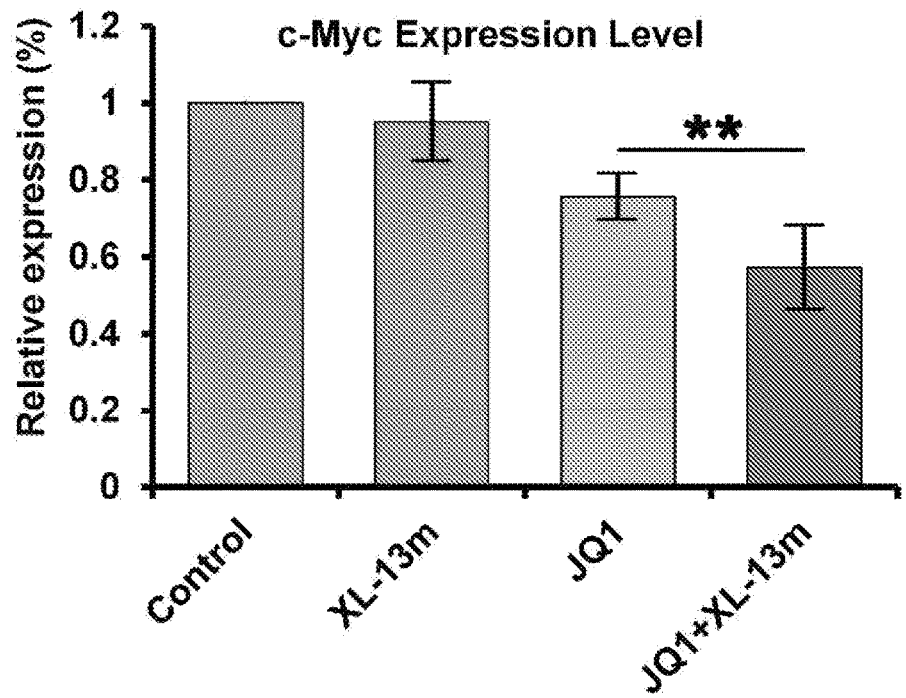
FIG. 49A is a graph showing the effect of treatment of MOLM13 cells with compound 39 (XL-13m) on the sensitivity of JQ1-induced decrease in c-Myc expression. Expression of c-Myc was quantified by qPCR. P value by student's t-test. Mean±s.d., three biological replicates.

MOLM13 (FLAG-ENL) cells were cultured with or without 50 μM compound XL-13m. Every 2-3 days, live cells were counted by trypan blue exclusion assay and re-plated. As shown in FIG. 48, compound XL-13m affected cell proliferation. MOLM13 (FLAG-ENL) cells were cultured with or without 50 μM compound XL-13m for 24 hours, and the cells were treated with 50 μM for another 24 hours. Treatment of cells with XL-13m increased the sensitivity of JQ1-induced decrease of c-Myc expression (FIG. 49A). Expression of c-Myc was quantified by qPCR.

Figure 49B:
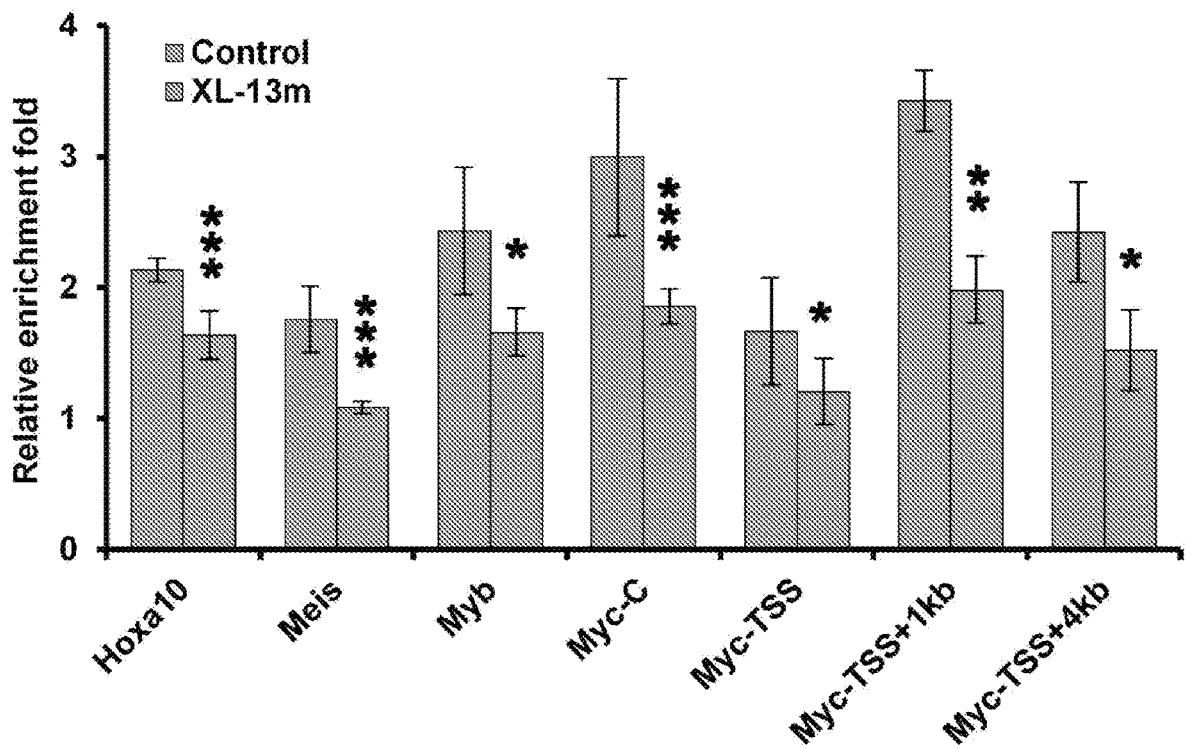
FIG. 49B is a graph showing the effect of treatment of MOLM13 cells with compound 39 (XL-13m) on enrichment of ENL on indicated genes. Percentage of input sample was quantified by qPCR, and the enrichment fold was normalized by the % input of Hoxa-intergenic region which does not have ENL enrichment. P value by student's t-test. Mean±s.d., triplicate PCR analysis.
Figure 50:
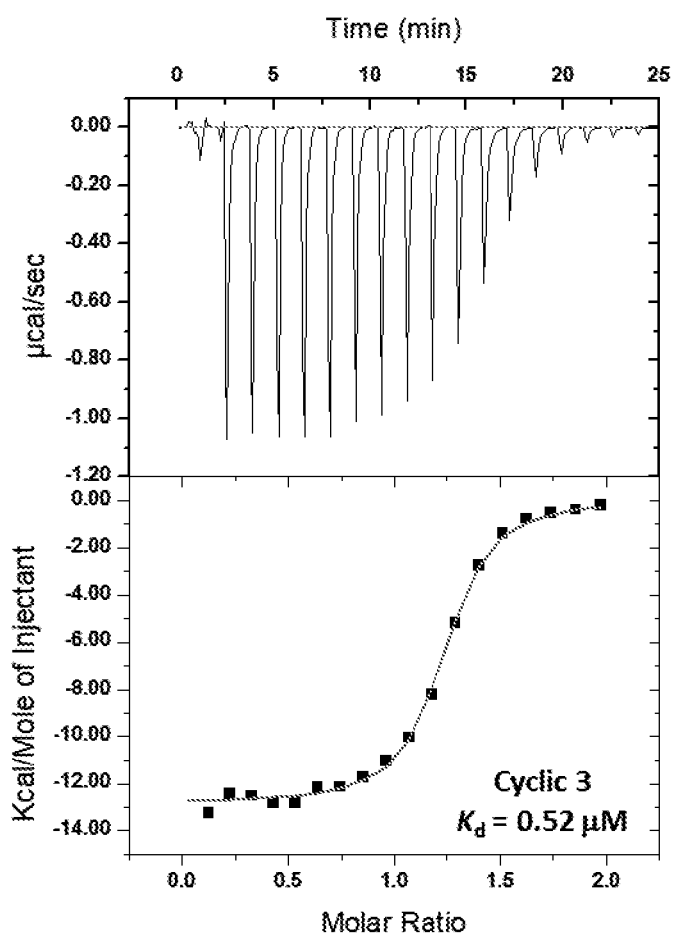
FIG. 50 is a graph showing ITC measurement for the dissociation constant between compound Cyclic 3 and AF9 YEATS domain, $K_d$=0.52 µM.
Figure 51:
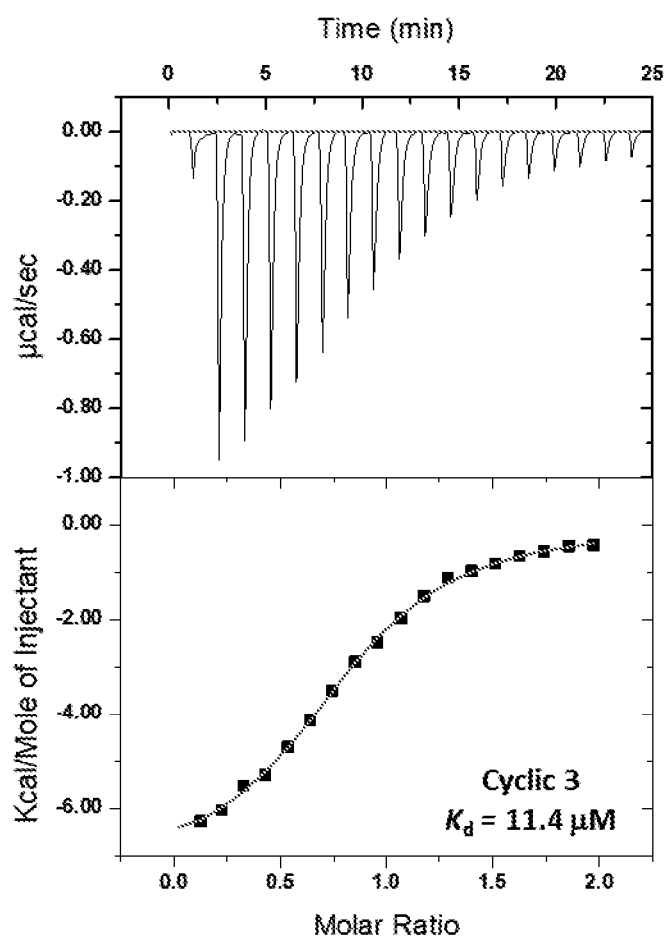
FIG. 51 is a graph showing ITC measurement for the dissociation constant between compound Cyclic 3 and ENL YEATS domain, $K_d$=11.4 µM.
Figure 52:
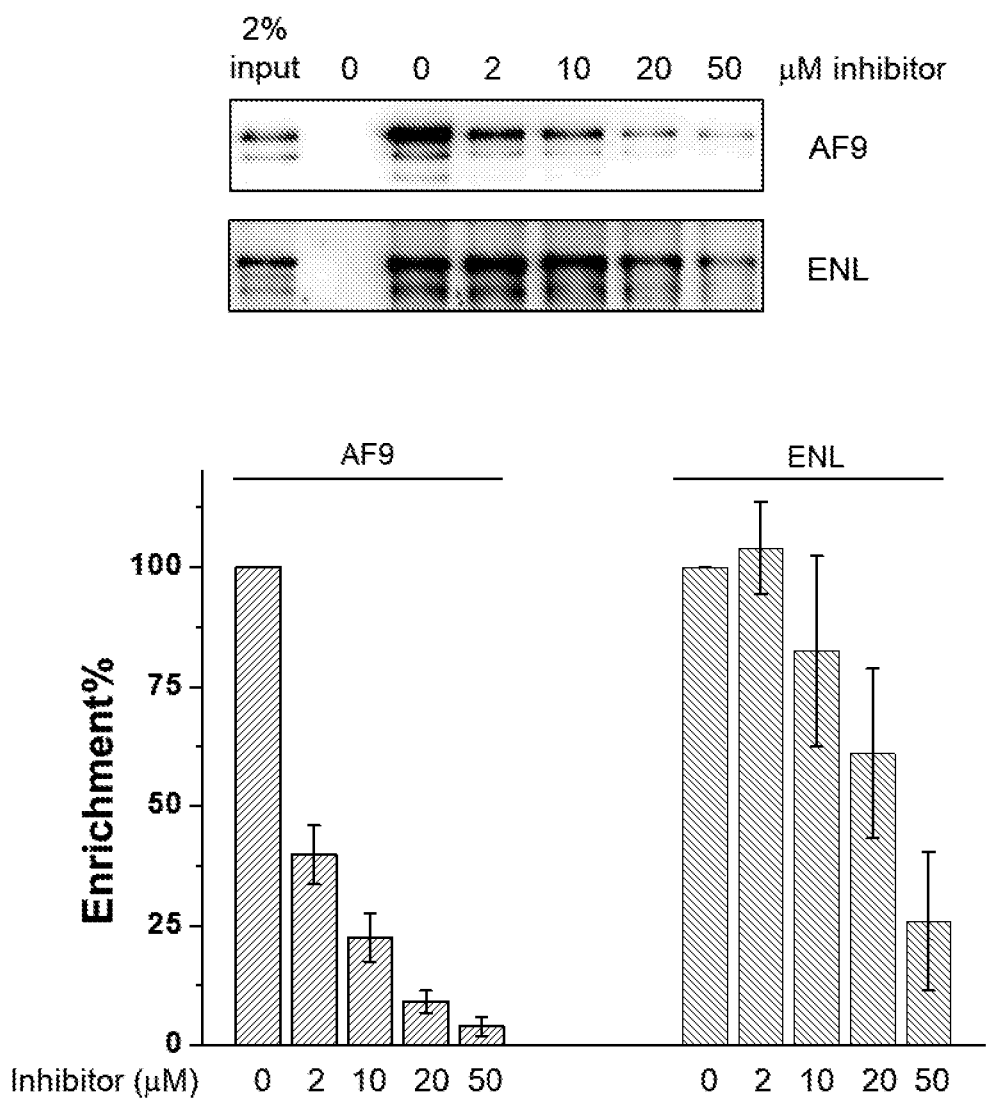
FIG. 52 is a graph showing in-vitro photo-cross-linking pulldown in nuclear extracts (1 mg/mL) with increasing concentrations of inhibitor Cyclic 3. The eluted protein mixtures were analyzed by immunoblotting against indicated antibodies. The blotting is representative of three independent experiments (upper panel). Quantification of the inhibitory effects of inhibitor Cyclic 3 on the enrichment of ENL and AF9 (mean±s.d., n=3) (bottom panel).
Figure 53:
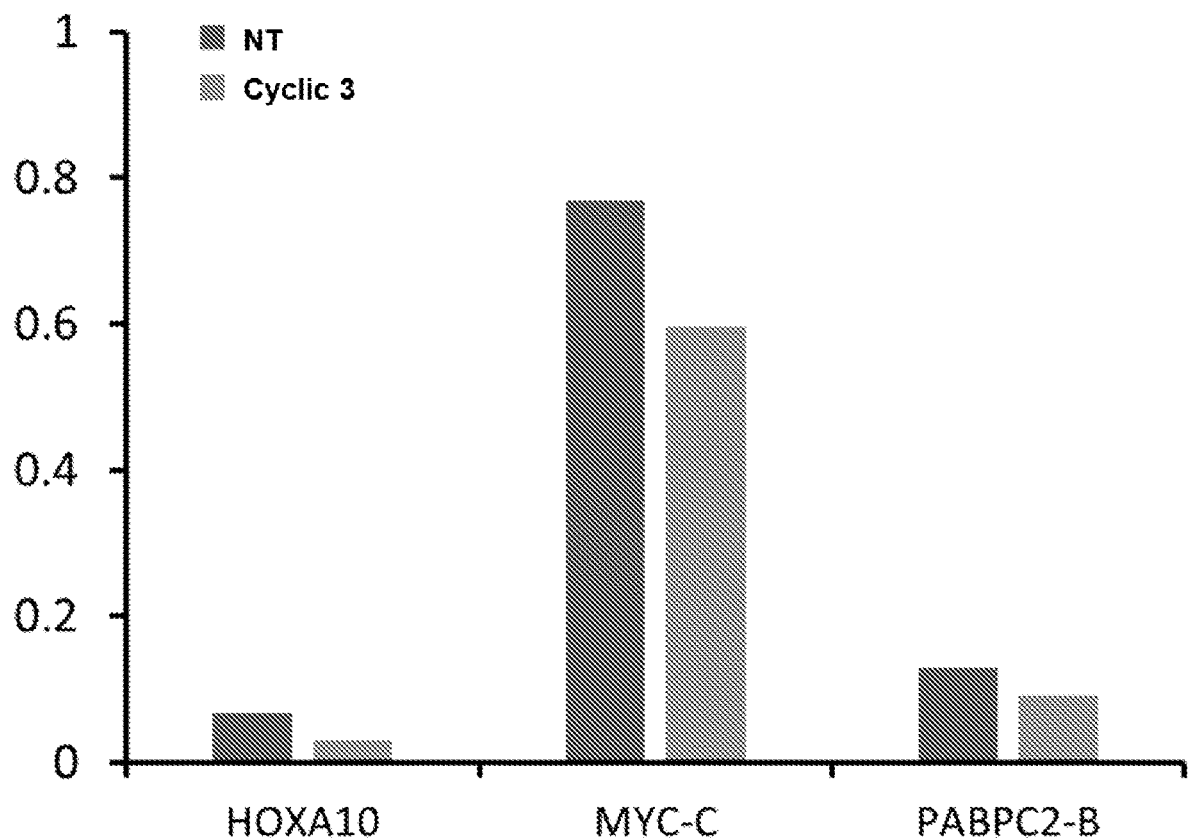
FIG. 53 is a graph showing chromatin immunoprecipitation and quantitative polymerase chain reaction (ChIP-qPCR) analysis of AF9 target genes in HeLa cells treated with or without inhibitor cyclic 3 (50 µM). The result showed that the abundance of AF9 at HOXA10, MYC, and PABPC2 was decreased in the HeLa cells treated with inhibitor cyclic 3, suggesting that engagement of the inhibitor with AF9 YEATS domain could indeed prevent the enrichment of AF9 on its targeted genes.
Figure 54:
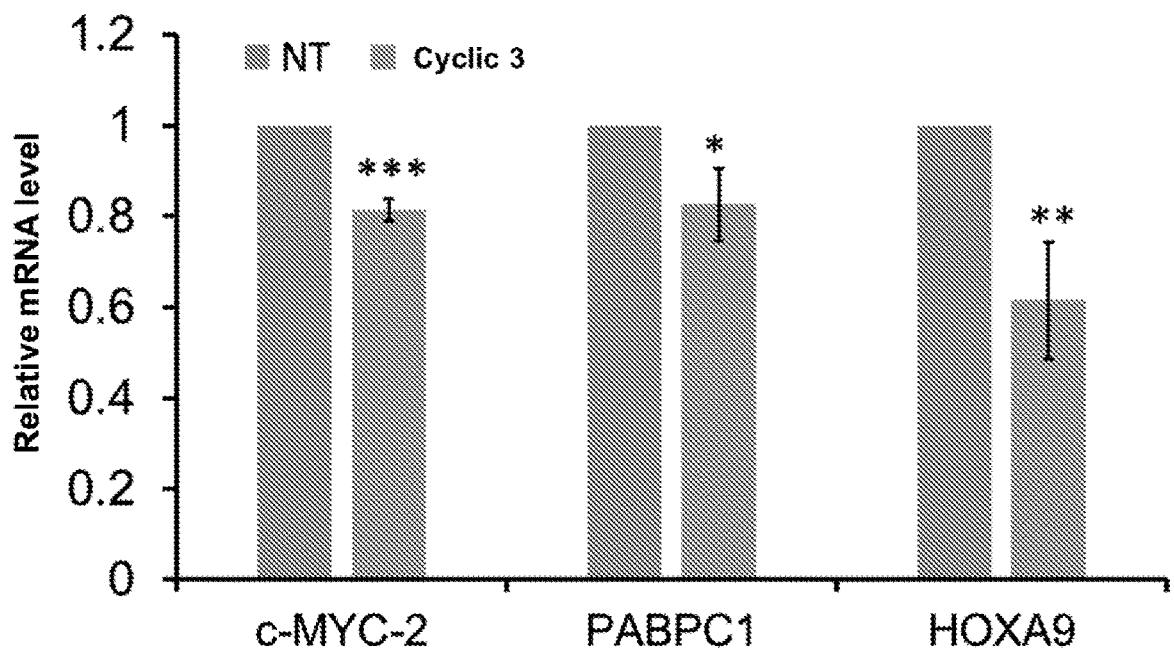
FIG. 54 is a graph showing real time-quantitative polymerase chain reaction (RT-qPCR) analysis shows mRNA levels of AF9 target genes in HeLa cells treated with or without inhibitor cyclic 3 (50 µM). The result indicated that inhibitor cyclic 3 led to the loss in the transcription levels of three AF9 target genes, MYC, PABPC1, and HOXA9. Data are presented as mean±s.e.m. from n=3. The P values are based on the two-tailed Student's test. *P<0.05, P<0.01, *P<0.001.

MOLM13 (FLAG-ENL) cells were cultured with or without 50 μM compound XL-13m for 72 hours. Percentage of input sample was quantified by qPCR, and the enrichment fold was normalized by the % input of Hoxa-intergenic region which does not have ENL enrichment. As shown in FIG. 49B, ChIP-qPCR revealed the decrease of the enrichment of ENL on indicated gene after treatment with XL-13m. MOLM13 (FLAG-ENL) cells were incubated with or without 50 μM compound for 16 hours and then were collected for cellular thermal shift assay (CETSA) as previously reported. Anti-FLAG antibody was used to detect ENL proteins and γ-actin blotting served as negative control. Thermal shift assay revealed the target of ENL protein by compounds XL-13l, XL-13m, and XL-13n in living cells.

CONCLUSIONS

Thirty-six AF9 YEATS domain inhibitors were designed and synthesized. A robust strategy combining photo-cross-linking and 'click chemistry' was employed to quantitatively measure the inhibitory activities of competitors. Preliminary screening of all inhibitors was performed to eliminate competitors with weak binding affinity to the AF9 YEATS domain. Half maximal inhibitory concentration (IC$_{50}$) of inhibitors with comparable activities were eventually determined. Yet, no inhibitors demonstrated improved inhibitory activity. Competitor Cbz-4, with an extended aromatic system at the N-terminus, demonstrated greatest activity among the other designed competitors. The IC$_{50}$ of competitor Cbz-4 was determined to be 0.226 μM, which is slightly greater than that of the competitor control (0.189 μM).

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

We claim:

1. A compound or a pharmaceutically acceptable salt thereof comprising a base oligomer and a side chain, wherein the compound is defined according to Formula (I):

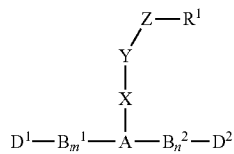

Formula (I)

wherein A is $CR^2$ or N;

wherein each instance of $B^1$ is independently an α-amino acid connected by amide linkage in a head-to-tail manner, —NH—, —O—, —S—, or —$(CH_2)_p$—, wherein p is an integer from 1 to 6;

wherein each instance of $B^2$ is independently an α-amino acid connected by amide linkage in a head-to-tail manner, —C(=O)—, —C(=NH)—, —C(=S)—, —S(=O)$_2$—, or -(a terminal bond);

wherein $D^1$ is H or unsubstituted or substituted hydrocarbyl, carbocyclyl or heterocyclyl;

wherein $D^2$ is H, $NH_2$, $NHR^{15}$, $NR^{16}R^{17}$, OH, $OR^{18}$, or unsubstituted or substituted hydrocarbyl, carbocyclyl or heterocyclyl;

wherein X is unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl;

wherein Y is $NR^3$, O, or S;

wherein Z is —CO—, —CS—, —$CNR^4$—, —SO—, or —$SO_2$—;

wherein $R^2$, $R^3$, and $R^4$ are independently H or $C_{1-10}$ hydrocarbyl, $C_{1-10}$ carbocyclyl, or $C_{1-10}$ heterocyclyl;

wherein $R^1$ is a conjugated/delocalized group;

wherein $R^{15}$, $R^{16}$, $R^{17}$, and $R^{18}$ are independently H, alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic;

wherein m and n are each independently integers from 0 to 10, wherein at least one of m or n is not 0, and wherein at least one $B^1$ or $B^2$ is an α-amino acid, and wherein the base oligomer is linear or monocyclic.

2. The compound of claim 1, wherein the compound is defined according to Formula (II):

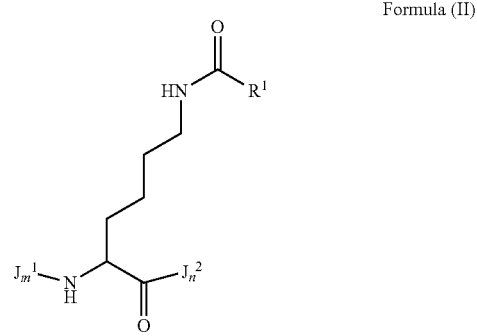

Formula (II)

wherein each instance of $J^1$ and $J^2$ is independently any α-amino acid;

wherein $R^1$ is a conjugated/delocalized group; and wherein m and n are each independently integers from 0 to 10, wherein at least one of m or n is not 0.

3. The compound of claim 1, wherein the compound is defined according to Formula (III):

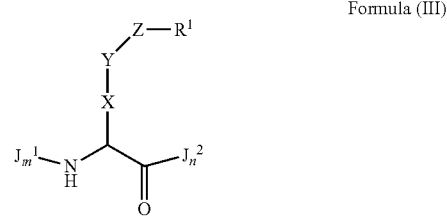

Formula (III)

wherein each instance of $J^1$ and $J^2$ is independently any α-amino acid;

wherein X is an unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl;

wherein Y is $NR^3$, O, or S;

wherein Z is —CO—, —CS—, —$CNR^4$—, —SO—, and —$SO_2$—;

wherein $R^3$ and $R^4$ are independently H or $C_{1-10}$ hydrocarbyl, $C_{1-10}$ carbocyclyl or $C_{1-10}$ heterocyclyl;

wherein $R^1$ is a conjugated/delocalized group; and wherein m and n are each independently integers from 0 to 10, wherein at least one of m or n is not 0.

4. The compound of claim 1, wherein the compound is defined according to Formula (IV):

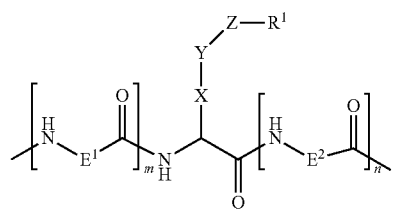

Formula (IV)

wherein each instance of $E^1$ and $E^2$ is independently an unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl, or O, S, or $NR^5$;

wherein X is an unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl;

wherein Y is $NR^3$, O, or S;

wherein Z is —CO—, —CS—, —CNR$^4$—, —SO—, or —SO$_2$—;

wherein $R^3$, $R^4$, and $R^5$ are independently a H, $C_{1-10}$ hydrocarbyl, $C_{1-10}$ carbocyclyl or $C_{1-10}$ heterocyclyl;

wherein $R^1$ is a conjugated/delocalized group; and wherein m and n are each independently integers from 0 to 10, wherein at least one of m or n is not 0.

5. The compound of claim 1, wherein at least two of the instances of $B^1$ linking units comprise side chains, wherein two of the side chains of the $B^1$ linking units are covalently coupled to each other forming a circular oligomer.

6. The compound of claim 1, wherein at least two of the instances of $B^2$ linking units comprise side chains, wherein two of the side chains of the $B^2$ linking units are covalently coupled to each other forming a circular oligomer.

7. The compound of claim 1, wherein the compound inhibits π-π-π stacking interactions.

8. The compound of claim 1, wherein the compound selectively targets the YEATS protein domain.

9. The compound of claim 1, wherein $R^1$ is selected from the group consisting of

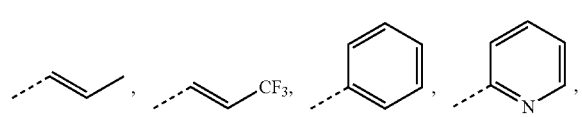

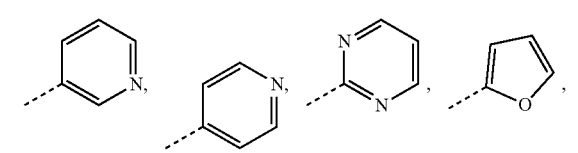

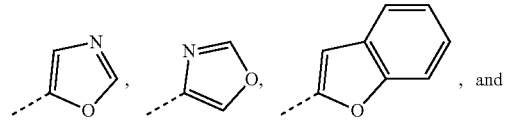

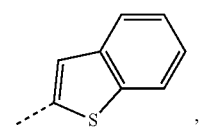

, and wherein the dashed lines denote the linkage point of each group.

10. The compound of claim 1, wherein in each instance of $B^1$ and/or $B^2$ being an α-amino acid, the α-amino acid is independently selected from the group consisting of Lys, Gln, Thr, Ala, Arg, Ser, Leu, Trp, and Gly.

11. The compound of claim 1, wherein the base oligomer comprises H$_2$N-Lys-Gln-Thr-Ala-Arg-Lys-Ser-Thr-Gly-Gly-CONH$_2$ (SEQ ID NO:1); H$_2$N-Gln-Thr-Ala-Arg-Lys-CONH$_2$ (SEQ ID NO:2); H$_2$N-Lys-Gln-Thr-Ala-Arg-Lys-CONH$_2$ (SEQ ID NO:3); CbzHN-Gln-Thr-Ala-Arg-Lys-CONH$_2$ (SEQ ID NO:4); KQTARK (SEQ ID NO:5); KQTARKSTGG (SEQ ID NO:6); KQ(T/A/S)ARK (SEQ ID NO:7); KQ(T/A/S)ARKSTGG (SEQ ID NO:8); KQT(A/L/W)RK (SEQ ID NO:9); KQT(A/L/W)RKSTGG (SEQ ID NO: 10); KQ(T/A/S)(A/L/W)RK (SEQ ID NO: 11); KQ(T/A/S)(A/L/W)RKSTGG (SEQ ID NO:12); KQAARK (SEQ ID NO: 13); KQAARKSTGG (SEQ ID NO:14); KQSARK (SEQ ID NO: 15); KQSARKSTGG (SEQ ID NO:16); KQTWRK (SEQ ID NO: 17); KQTWRKSTGG (SEQ ID NO: 18); KQTLRK (SEQ ID NO:19); or KQTLRKSTGG (SEQ ID NO:20); or a fragment thereof.

12. A pharmaceutical composition comprising an effective amount of the compound of claim 1.

13. The composition of claim 12, further comprising one or more pharmaceutically acceptable carriers or excipients.

14. The composition of claim 12, wherein the compound selectively inhibits π-π-π stacking interactions.

15. The composition of claim 12, wherein the compound selectively targets the YEATS protein domain.

16. The composition of claim 12, wherein the compound is effective for treating cancer.

17. The composition of claim 16, wherein the cancer is acute leukemia.

18. A method for treating cancer, the method comprising administering the composition of claim 12 to a subject in need thereof.

19. The method of claim 18, wherein the subject has acute leukemia.

20. A compound or a pharmaceutically acceptable salt thereof comprising a base oligomer and a side chain, wherein the compound is defined according to Formula (V):

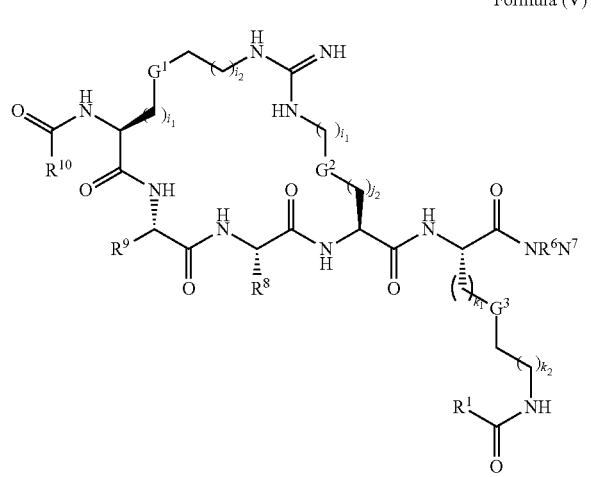

Formula (V)

wherein $R^1$ is a conjugated/delocalized group, comprising unsubstituted or substituted aromatic rings, or unsubstituted or substituted alkenyl or alkynyl;

wherein $R^6$, $R^7$, $R^8$, $R^9$, and $R^{10}$ are independently H or $C_{1-10}$ hydrocarbyl, $C_{1-10}$ carbocyclyl or $C_{1-10}$ heterocyclyl;

wherein each of $G^1$, $G^2$, and $G^3$ is an unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl, or 5 to 9-membered heteroaryl; and wherein $i_1$, $i_2$, $j_1$, $j_2$, $k_1$, $k_2$ are each independently integers from 0 to 10.

21. A compound or a pharmaceutically acceptable salt thereof comprising a base oligomer and a side chain, wherein the compound is defined according to Formula (I):

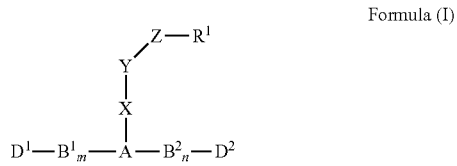

Formula (I)

wherein A is $CR^2$ or N;

wherein each instance of $B^1$ is independently an α-amino acid connected by amide linkage in a head-to-tail manner, —NH—, —O—, —S—, or —$(CH_2)_p$—, wherein p is an integer from 1 to 6;

wherein each instance of $B^2$ is independently an α-amino acid connected by amide linkage in a head-to-tail manner, —C(=O)—, —C(=NH)—, —C(=S)—, —S(=O)$_2$—, or -(a terminal bond);

wherein $D^1$ is H or unsubstituted or substituted hydrocarbyl, carbocyclyl or heterocyclyl;

wherein $D^2$ is H, $NH_2$, $NHR^{15}$, $NR^{16}R^{17}$, OH, $OR^{18}$, or unsubstituted or substituted hydrocarbyl, carbocyclyl or heterocyclyl;

wherein X is unsubstituted or substituted $C_{1-10}$ alkyl, $C_{1-10}$ alkenyl, $C_{1-10}$ alkynyl, $C_{1-10}$ carbocyclyl, $C_{1-10}$ heteroalkyl, $C_{1-10}$ heteroalkenyl, $C_{1-10}$ heteroalkynyl, or $C_{1-10}$ heterocyclyl;

wherein Y is $NR^3$, O, or S;

wherein Z is —CO—, —CS—, —$CNR^4$—, —SO—, or —$SO_2$—;

wherein $R^2$, $R^3$, and $R^4$ are independently H or $C_{1-10}$ hydrocarbyl, $C_{1-10}$ carbocyclyl, or $C_{1-10}$ heterocyclyl;

wherein $R^1$ is a conjugated/delocalized group;

wherein $R^{15}$, $R^{16}$, $R^{17}$, and $R^{18}$ are independently H, alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic;

wherein m and n are each independently integers from 0 to 10, wherein at least one of m or n is not 0, wherein at least one $B^1$ or $B^2$ is an α-amino acid, and wherein the base oligomer comprises SEQ ID NO: 13; SEQ ID NO:14; SEQ ID NO: 15; SEQ ID NO: 17; SEQ ID NO: 18; SEQ ID NO:19; or SEQ ID NO:20.

* * * * *